(12) United States Patent
Murakami et al.

(10) Patent No.: US 11,103,410 B2
(45) Date of Patent: Aug. 31, 2021

(54) ASSISTANCE APPARATUS, ASSISTANCE METHOD, AND RECORDING MEDIUM

(71) Applicant: Panasonic Intellectual Property Management Co., Ltd., Osaka (JP)

(72) Inventors: Kenta Murakami, Osaka (JP); Stephen William John, Nara (JP); Hiroki Takeuchi, Osaka (JP); Shinobu Adachi, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 337 days.

(21) Appl. No.: 16/158,350

(22) Filed: Oct. 12, 2018

(65) Prior Publication Data
US 2019/0125610 A1 May 2, 2019

(30) Foreign Application Priority Data
Oct. 31, 2017 (JP) .............................. JP2017-211384

(51) Int. Cl.
*A61H 1/00* (2006.01)
*A61B 5/00* (2006.01)
(Continued)

(52) U.S. Cl.
CPC ............ *A61H 1/0262* (2013.01); *A61B 5/112* (2013.01); *A61B 5/6831* (2013.01); *A61H 3/008* (2013.01);
(Continued)

(58) Field of Classification Search
CPC ...... A61H 3/00; A61H 1/0266; A61H 1/0237; A61H 1/024; A61H 1/0244;
(Continued)

(56) References Cited

U.S. PATENT DOCUMENTS

| | | | |
|---|---|---|---|
| 2014/0296761 A1* | 10/2014 | Yamamoto | A61H 3/00 602/23 |
| 2015/0173993 A1* | 6/2015 | Walsh | B25J 9/0006 414/4 |

(Continued)

FOREIGN PATENT DOCUMENTS

| | | |
|---|---|---|
| JP | 2009-213538 | 9/2009 |
| JP | 2016-528940 | 9/2016 |

*Primary Examiner* — Quang D Thanh
(74) *Attorney, Agent, or Firm* — Wenderoth, Lind & Ponack, L.L.P.

(57) ABSTRACT

An assistance apparatus includes a first wire and a second wire that couple an upper-body belt and a left knee belt to each other on or above a front part and back part of the body of a user, respectively, a third wire and a fourth wire that couple the upper-body belt and a right knee belt to each other on or above the front part and back part of the body of the user, respectively, a motor, a left sensor on the left hand of the user, and a right sensor on the right hand of the user. When a force is applied to the left sensor and no force is applied to the right sensor, the motor makes the tension of the second wire and the third wire greater than the tension of the first wire and the fourth wire. When a force is applied to the right sensor and no force is applied to the left sensor, the motor makes the tension of the first wire and the fourth wire greater than the tension of the second wire and the third wire.

18 Claims, 30 Drawing Sheets

(51) Int. Cl.
 *A61H 1/02* (2006.01)
 *A61B 5/11* (2006.01)
 *A61H 3/00* (2006.01)
 *A61F 5/01* (2006.01)

(52) U.S. Cl.
 CPC ............... *A61F 2005/0155* (2013.01); *A61F 2005/0188* (2013.01); *A61H 1/0255* (2013.01); *A61H 2003/007* (2013.01); *A61H 2201/1207* (2013.01); *A61H 2201/14* (2013.01); *A61H 2201/16* (2013.01); *A61H 2201/1642* (2013.01); *A61H 2201/1652* (2013.01); *A61H 2201/5025* (2013.01); *A61H 2201/5061* (2013.01); *A61H 2201/5079* (2013.01); *A61H 2201/5084* (2013.01); *A61H 2230/60* (2013.01); *A63B 2225/50* (2013.01)

(58) Field of Classification Search
 CPC .... A61H 2201/5061; A61H 2201/5025; A61H 2201/5035; A61H 2201/165; A61H 2201/5046; A61H 2201/5079; A61H 2201/5023; A61H 2201/5071; A61H 2201/0192; A61H 2201/1238; A61H 2201/5069; A61H 2201/5028; A61H 2205/10; A61H 2201/14; A61H 2201/50; A61H 2003/007; A61H 2201/1215; A61H 2201/149; A61H 2201/5097; A61H 2201/1642; A61H 2201/1652; A61H 2201/5007; A61H 2201/5012; A61H 2201/5084; A61H 2201/163; A61B 5/1125; A61B 5/1038; A61B 5/112; A61B 2562/0219; A61B 2562/0257; A61B 2505/09

See application file for complete search history.

(56) References Cited

U.S. PATENT DOCUMENTS

| | | | |
|---|---|---|---|
| 2016/0107309 A1* | 4/2016 | Walsh | A61H 3/00 248/550 |
| 2017/0202724 A1 | 7/2017 | De Rossi et al. | |
| 2019/0125615 A1* | 5/2019 | Murakami | A61B 5/112 |
| 2019/0125616 A1* | 5/2019 | John | A61B 5/4851 |

\* cited by examiner

LEFT LEG FLEXION
110a1 → HIGH TENSION

RIGHT LEG FLEXION
110a3 → HIGH TENSION

LEFT LEG EXTENSION
110a2 → HIGH TENSION

RIGHT LEG EXTENSION
110a4 → HIGH TENSION

LEFT LEG EXTENSION
110a2 → HIGH TENSION
110a6 → HIGH TENSION

RIGHT LEG EXTENSION
110a4 → HIGH TENSION
110a8 → HIGH TENSION

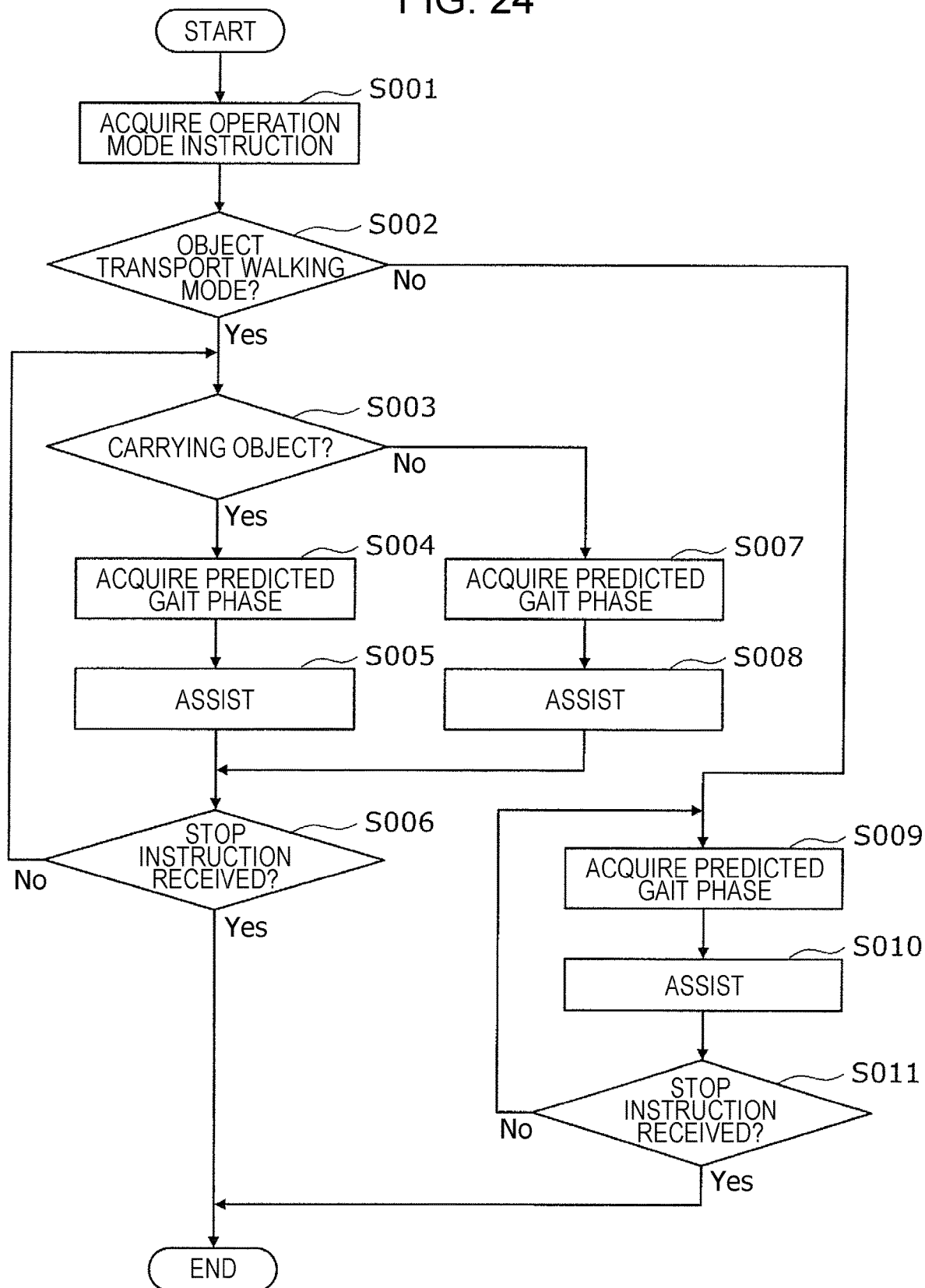

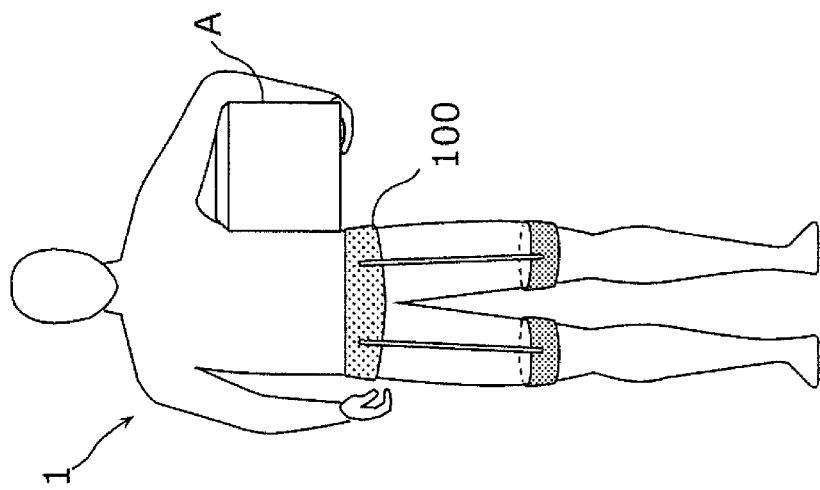
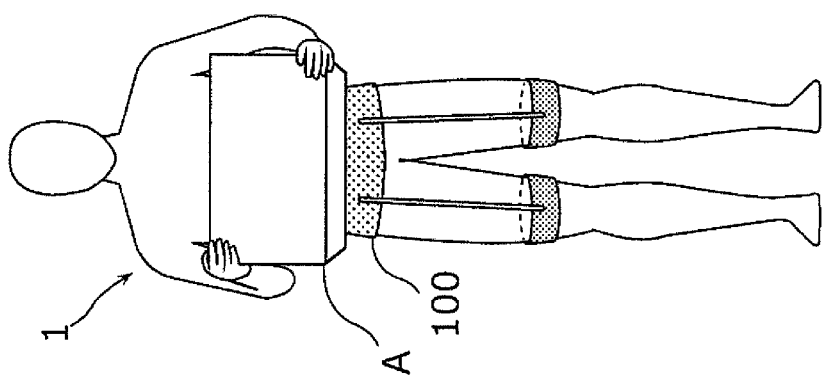
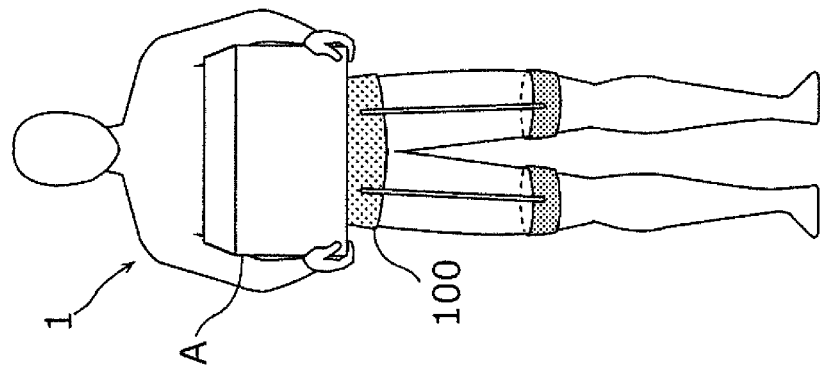

ASSISTANCE APPARATUS, ASSISTANCE METHOD, AND RECORDING MEDIUM

BACKGROUND

1. Technical Field

The present disclosure relates to an assistance apparatus, an assistance method, and a recording medium for assisting a wearer in walking.

2. Description of the Related Art

For example, Japanese Unexamined Patent Application Publication No. 2009-213538 discloses an assistant outfit for assisting movements of joints of a user. The disclosed assistant outfit includes a thigh link to be attached to a thigh, a thigh restraint band that restrains movement of the thigh link, a lower-leg link to be attached to a lower leg, a lower-leg restraint band that restrains movement of the lower-leg link, and a knee assistant motor that changes the angle between the thigh link and the lower-leg link. Japanese Unexamined Patent Application Publication (Translation of PCT Application) No. 2016-528940 discloses a soft exosuit equipped with an actuator including an operating member. In the soft exosuit, activation of the actuator generates a moment around a joint of a user wearing the soft exosuit to assist the movement of the user.

SUMMARY

A need exists to provide assistance for movements of a user in different ways in accordance with the state of the user, such as whether the user is carrying an object such as luggage. A specific method for addressing this issue is not described in Japanese Unexamined Patent Application Publication No. 2009-213538 or Japanese Unexamined Patent Application Publication (Translation of PCT Application) No. 2016-528940.

One non-limiting and exemplary embodiment provides an assistance apparatus, an assistance method, and a recording medium that provide assistance in accordance with the state of a user.

In one general aspect, the techniques disclosed here feature an assistance apparatus including an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, at least one motor, a left sensor attachable to a left hand of the user, a right sensor attachable to a right hand of the user, and a control circuit. When the assistance apparatus assists the user in walking while carrying an object, the at least one motor generates (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, and (iv) a tension greater than or equal to the first threshold value in the fourth wire during a fourth period, the fourth period being a period of 0% or more and 25% or less and 65% or more and less than 100% of the gait phase of the right leg. The control circuit acquires a left sensor value from the left sensor and a right sensor value from the right sensor. The control circuit detects a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value. When the first condition is detected, the at least one motor makes the tension of the second wire in the second period and the tension of the third wire in the third period greater than the tension of the first wire in the first period and the tension of the fourth wire in the fourth period. When the second condition is detected, the at least one motor makes the tension of the first wire in the first period and the tension of the fourth wire in the fourth period greater than the tension of the second wire in the second period and the tension of the third wire in the third period.

It should be noted that general or specific embodiments may be implemented as a system, an apparatus, a method, an integrated circuit, a computer program, a computer-readable recording medium such as a recording disk, or any selective combination thereof. The computer-readable recording medium includes a non-volatile recording medium such as a compact disc-read only memory (CD-ROM).

An assistance apparatus and so on according to aspects of the present disclosure can provide assistance in accordance with the state of a user. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 24 is a flowchart illustrating an example overall flow of an operation of the assistance apparatus according to the embodiment for assisting a user;

FIG. 26A is a diagram illustrating an example of how a user carries an object;

FIG. 26B is a diagram illustrating another example of how a user carries an object;

FIG. 26C is a diagram illustrating still another example of how a user carries an object;

DETAILED DESCRIPTION

Figure 1:
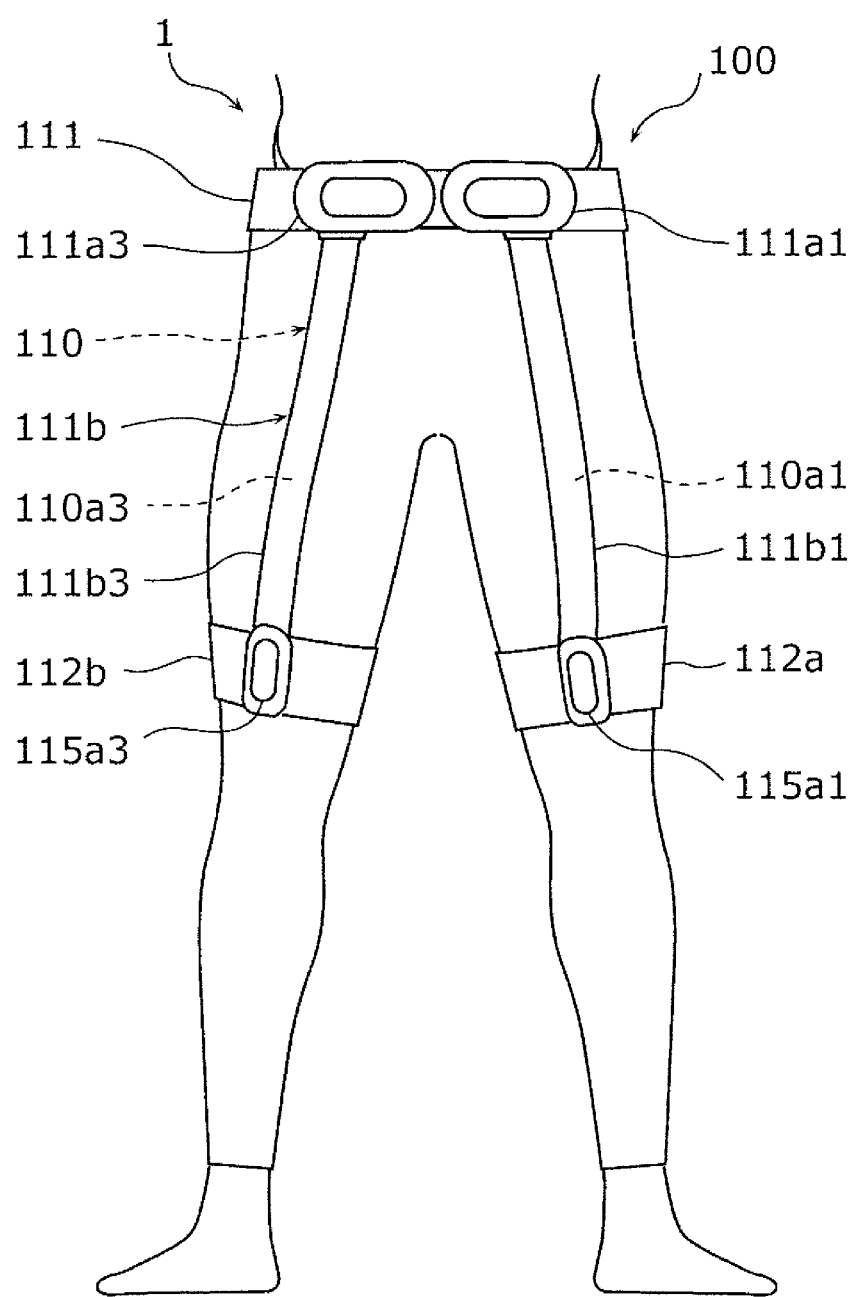
FIG. 1 is a front view of a user wearing an assistance apparatus according to an embodiment, as viewed from the front.

Underlying Knowledge Forming Basis of the Present Disclosure

The inventors of the present disclosure, or the present inventors, have studied the techniques described in Japanese Unexamined Patent Application Publication No. 2009-213538 (hereinafter referred to as "Patent Literature 1") and Japanese Unexamined Patent Application Publication (Translation of PCT Application) No. 2016-528940 (hereinafter referred to as "Patent Literature 2") mentioned in the "BACKGROUND" section and have examined techniques for supporting, or assisting, a user in walking. The present inventors have focused on changing states of a user, who is a wearer of an assistance apparatus. For example, it is necessary that an assistance method for a user who is carrying an object such as luggage be different from an assistance method for a user who is carrying no object.

First, the present inventors have examined an assistance apparatus that assists a user in walking by applying forces generated by motors to the user through wires. To enable various kinds of assistance on the legs of a user, the present inventors have developed an assistance apparatus including wires, each of which is to be placed so as to extend across one of the front of the hip joint of the left leg of the user, the back of the hip joint of the left leg of the user, the front of the hip joint of the right leg of the user, and the back of the hip joint of the right leg of the user. The present inventors have further developed a configuration in which the wires are each coupled to an upper-body belt and a left knee belt or a right knee belt, which are to be attached to the body of the user, and are accordingly attached to the body of the user. Thus, the present inventors have devised an assistance apparatus having a simple configuration.

For example, Patent Literature 1 discloses an assistant outfit including a rod-shaped thigh link that is attached to a side portion of a thigh, and a rod-shaped lower-leg link that is attached to a side portion of a lower leg. The thigh link and the lower-leg link are coupled to a knee assistant motor. The knee assistant motor is driven to change the angle defined by the thigh link and the lower-leg link, and accordingly the assistant outfit assists flexion and extension of the knee of the user. The thigh link, the lower-leg link, and the knee assistant motor are attached to each of the side portion of the right leg of the user and the side portion of the left leg of the user, resulting in the assistant outfit disclosed in Patent Literature 1 having a structure that is large-scale and complicated for the user. Thus, the assistant outfit places a heavy burden on the user.

In Patent Literature 2, tension is applied to connection elements of the soft exosuit, which is worn on a part of the body of the user from the waist to a thigh and a lower leg, through a cable placed at the front part of the thigh of the user, thereby assisting flexion and extension of the knee of the user. In the soft exosuit disclosed in Patent Literature 2, the connection elements and so on, which are attached to the body of the user, are large-scale and complicated for the user. Thus, the soft exosuit places a heavy burden on the user.

In addition, none of Patent Literatures 1 and 2 discloses the details of a method for providing assistance in accordance with the state of a user. Accordingly, the present inventors have devised the following technique for providing assistance in accordance with the state of a user by using the assistance apparatus having a simple configuration described above.

An assistance apparatus according to a first aspect of the present disclosure includes an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, at least one motor, a left sensor attachable to a left hand of the user, a right sensor attachable to a right hand of the user, and a control circuit. When the assistance apparatus assists the user in walking while carrying an object, the at least one motor generates (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, and (iv) a tension greater than or equal to the first threshold value in the fourth wire during a fourth period, the fourth period being a period of 0% or more and 25% or less and 65% or more and less than 100% of the gait phase of the right leg. The control circuit acquires a left sensor value from the left sensor and a right sensor value from the right sensor. The control circuit detects a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value. When the first condition is detected, the at least one motor makes the tension of the second wire in the second period and the tension of the third wire in the third period greater than the tension of the first wire in the first period and the tension of the fourth wire in the fourth period. When the second condition is detected, the at least one motor makes the tension of the first wire in the first period and the tension of the fourth wire in the fourth period greater than the tension of the second wire in the second period and the tension of the third wire in the third period.

In the configuration described above, the tension generated in the first wire can apply an assistance force for flexion to the left leg of the user, and the tension generated in the third wire can apply an assistance force for flexion to the right leg of the user. The tension generated in the second wire can apply an assistance force for extension to the left leg of the user, and the tension generated in the fourth wire can apply an assistance force for extension to the right leg of the user. The assistance apparatus generates a tension greater than or equal to the first threshold value in the first wire during the first period in the gait phase of the left leg to assist flexion of the left leg, and generates a tension greater than or equal to the first threshold value in the third wire during the third period in the gait phase of the right leg to assist flexion of the right leg, thereby assisting the user in walking. Further, the assistance apparatus generates a tension greater than or equal to the first threshold value in the second wire during the second period in the gait phase of the left leg to assist extension of the left leg, and generates a tension greater than or equal to the first threshold value in the fourth wire during the fourth period in the gait phase of the right leg to assist extension of the right leg, thereby assisting the user in walking. The first threshold value may be a tension value that allows the user to recognize that the movement of a leg is promoted by a tension generated in a wire, and may be 40 newtons (N), for example.

Further, in the first condition, a force is applied to the left sensor, whereas no force is applied to the right sensor. Thus, it is probable that the user carries an object only in the left hand and that the load imposed on the left leg is larger than that on the right leg. In this case, the assistance apparatus makes the tensions of the wires different from each other to make the assistance force for extension of the left leg and the assistance force for flexion of the right leg larger than the assistance force for flexion of the left leg and the assistance force for extension of the right leg. In the second condition, a force is applied to the right sensor, whereas no force is applied to the left sensor. Thus, it is probable that the user carries an object only in the right hand and that the load imposed on the right leg is larger than that on the left leg. In this case, the assistance apparatus makes the tensions of the wires different from each other to make the assistance force for flexion of the left leg and the assistance force for extension of the right leg larger than the assistance force for extension of the left leg and the assistance force for flexion of the right leg. In either condition, the assistance force for extension of a leg bearing a larger load is larger than the assistance force for extension of a leg bearing a smaller load. The assistance force for extension supports a leg bearing a gravitationally downward load and reduces the burden on the leg. Accordingly, the assistance apparatus can provide balanced assistance with the burdens on the left and right legs being made uniform and reduced. In this case, the user can walk by moving the left and right legs in a well-balanced manner while feeling uniform loads being imposed on the left and right legs. In either condition, furthermore, the assistance force for flexion of a leg bearing a smaller load is larger than the assistance force for flexion of a leg bearing a larger load. Accordingly, the assistance apparatus can assist the user to facilitate walking on a leg bearing a smaller load and can induce the progress of the user's walking. In addition, the assistance apparatus increases an assistance force for each of the left and right legs, thus enabling well-balanced assistance for the left and right legs. Thus, the assistance apparatus can provide assistance to the user in accordance with the state of the user.

An assistance apparatus according to a second aspect of the present disclosure includes an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, at least one motor, and a control circuit. When the assistance apparatus assists the user in walking while carrying an object, the at least one motor generates (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, and (iv) a tension greater than or equal to the first threshold value in the fourth wire during a fourth period, the fourth period being a period of 0% or more and 25% or less and 65% or more and less than 100% of the gait phase of the right leg. The control circuit acquires information specifying a hand that carries the object. When the information indicates a left hand of the user, the at least one motor makes the tension of the second wire in the second period and the tension of the third wire in the third period greater than the tension of the first wire in the first period and the tension of the fourth wire in the fourth period. When the information indicates a right hand of the user, the at least one motor makes the tension of the first wire in the first period and the tension of the fourth wire in the fourth period greater than the tension of the second wire in the second period and the tension of the third wire in the third period.

In the configuration described above, when the left hand is designated as a hand carrying the object, the assistance apparatus makes the tensions of the wires different from each other to make the assistance force for extension of the left leg and the assistance force for flexion of the right leg larger than the assistance force for flexion of the left leg and the assistance force for extension of the right leg. When the right hand is designated as a hand carrying the object, the assistance apparatus makes the tensions of the wires different from each other to make the assistance force for flexion of the left leg and the assistance force for extension of the right leg larger than the assistance force for extension of the left leg and the assistance force for flexion of the right leg. The load imposed on the leg on the same side as the hand carrying the object is larger than the load imposed on the leg on the same side as the hand not carrying the object. In either case, the assistance force for extension of a leg bearing a larger load is larger than the assistance force for extension of a leg bearing a smaller load. Thus, the assistance apparatus can provide balanced assistance with the burdens on the left and right legs being made uniform and reduced. Furthermore, the assistance force for flexion of a leg bearing a smaller load is larger than the assistance force for flexion of a leg bearing a larger load. Thus, the assistance apparatus can assist the user to facilitate walking on a leg bearing a smaller load. In addition, the assistance apparatus increases an assistance force for each of the left and right legs, thus enabling well-balanced assistance for the left and right legs. Thus, the assistance apparatus can provide assistance to the user in accordance with the state of the user.

The assistance apparatus according to the second aspect of the present disclosure may further include an interface device. The control circuit may receive the information via the interface device.

In the configuration described above, in response to receipt of input from a user wearing the assistance apparatus, the assistance apparatus can determine a hand carrying an object in accordance with the designation by the user.

In the assistance apparatuses according to the first and second aspects of the present disclosure, the left leg may shift from a stance phase to a swing phase during the first period, the left leg may shift from the swing phase to the stance phase during the second period, the right leg may shift from the stance phase to the swing phase during the third period, and the right leg may shift from the swing phase to the stance phase during the fourth period.

In the configuration described above, the assistance apparatus assists flexion during the first period in which the left leg shifts from the stance phase to the swing phase, and assists flexion during the third period in which the right leg shifts from the stance phase to the swing phase. Thus, the assistance apparatus can effectively assist the user in walking. Further, the assistance apparatus assists extension during the second period in which the left leg shifts from the swing phase to the stance phase, and assists extension during the fourth period in which the right leg shifts from the swing phase to the stance phase. Thus, the assistance apparatus can effectively assist the user in walking.

In the assistance apparatuses according to the first and second aspects of the present disclosure, the at least one motor may include a first motor, a second motor, a third motor, and a fourth motor. The first wire may have a first end fixed to the left knee belt, and the first wire may have a second end fixed to the first motor. The second wire may have a first end fixed to the left knee belt, and the second wire may have a second end fixed to the second motor. The third wire may have a first end fixed to the right knee belt, and the third wire may have a second end fixed to the third motor. The fourth wire may have a first end fixed to the right knee belt, and the fourth wire may have a second end fixed to the fourth motor.

In the configuration described above, the assistance apparatus can separately control the tension of the first wire, the tension of the second wire, the tension of the third wire, and the tension of the fourth wire. Thus, the assistance apparatus can provide fine assistance.

The assistance apparatuses according to the first and second aspects of the present disclosure may further include a fifth wire that couples the upper-body belt and the left knee belt to each other and that extends on or above the front part of the body of the user in a direction crossing a direction in which the first wire extends, a sixth wire that couples the upper-body belt and the left knee belt to each other and that extends on or above the back part of the body of the user in a direction crossing a direction in which the second wire extends, a seventh wire that couples the upper-body belt and the right knee belt to each other and that extends on or above the front part of the body of the user in a direction crossing a direction in which the third wire extends, and an eighth wire that couples the upper-body belt and the right knee belt to each other and that extends on or above the back part of the body of the user in a direction crossing a direction in which the fourth wire extends. When the assistance apparatus assists the user in walking while carrying the object, the at least one motor may generate (i) a tension greater than or equal to the first threshold value in the first wire and the fifth wire during the first period, (ii) a tension greater than or equal to the first threshold value in the second wire and the sixth wire during the second period, (iii) a tension greater than or equal to the first threshold value in the third wire and the seventh wire during the third period, and (iv) a tension greater than or equal to the first threshold value in the fourth wire and the eighth wire during the fourth period.

In the configuration described above, the tension generated in the first wire and the tension generated in the fifth wire can apply an assistance force for flexion to the left leg of the user. The tension generated in the second wire and the tension generated in the sixth wire can apply an assistance force for extension to the left leg of the user. The tension generated in the third wire and the tension generated in the seventh wire can apply an assistance force for flexion to the right leg of the user. The tension generated in the fourth wire and the tension generated in the eighth wire can apply an assistance force for extension to the right leg of the user. Thus, the assistance apparatus including the first to eighth wires can provide assistance similar to that of the assistance apparatus including the first to fourth wires. In addition, the assistance apparatus including the first to eighth wires separately controls the tensions of the first to eighth wires, thereby providing more types of assistance. For example, the tension generated in the first wire and the tension generated in the fifth wire may be the same or different, and a different type of assistance can be provided in each case.

In the assistance apparatuses according to the first and second aspects of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance apparatuses according to the first and second aspects of the present disclosure may further include a memory. The memory may store a program for controlling the at least one motor. The control circuit may control the at least one motor in accordance with the program.

The assistance apparatuses according to the first and second aspects of the present disclosure may further include a gait sensor that detects a gait cycle of the user. The control circuit may calculate the gait phase of the left leg and the gait phase of the right leg based on a sensor value of the gait sensor.

In the configuration described above, the assistance apparatus can assist the user in walking on the basis of a gait phase corresponding to a gait cycle of the user. Thus, the assistance apparatus can provide assistance based on actual user walking.

An assistance method according to the first aspect of the present disclosure is an assistance method for assisting a movement of a user by using wires attached to a body of the user. The assistance method includes coupling, using a first wire among the wires, an upper-body belt and a left knee belt to each other on or above a front part of the body of the user, the upper-body belt being a belt to be worn on an upper half of the body of the user, the left knee belt being a belt to be worn on a left knee of the user; coupling, using a second wire among the wires, the upper-body belt and the left knee belt to each other on or above a back part of the body of the user; coupling, using a third wire among the wires, the upper-body belt and a right knee belt to each other on or above the front part of the body of the user, the right knee belt being a belt to be worn on a right knee of the user; coupling, using a fourth wire among the wires, the upper-body belt and the right knee belt to each other on or above the back part of the body of the user; when assisting the user in walking while carrying an object, generating a tension greater than or equal to a first threshold value in the first wire during a first period, the first period being a period of 35% or more and 90% or less of a gait phase of a left leg of the user; generating a tension greater than or equal to the first threshold value in the second wire during a second period, the second period being a period of 0% or more and 25% or less and 65% or more and less than 100% of the gait phase of the left leg; generating a tension greater than or equal to the first threshold value in the third wire during a third period, the third period being a period of 35% or more and 90% or less of a gait phase of a right leg of the user; generating a tension greater than or equal to the first threshold value in the fourth wire during a fourth period, the fourth period being a period of 0% or more and 25% or less and 65% or more and less than 100% of the gait phase of the right leg; acquiring a left sensor value from a left sensor attached to a left hand of the user; acquiring a right sensor value from a right sensor attached to a right hand of the user; detecting a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value; when the first condition is detected, making the tension of the second wire in the second period and the tension of the third wire in the third period greater than the tension of the first wire in the first period and the tension of the fourth wire in the fourth period; and when the second condition is detected, making the tension of the first wire in the first period and the tension of the fourth wire in the fourth period greater than the tension of the second wire in the second period and the tension of the third wire in the third period. The tension of the first wire, the tension of the second wire, the tension of the third wire, and the tension of the fourth wire are adjusted by a motor that is controlled by at least one control circuit. The assistance method according to the first aspect described above can achieve advantages similar to those of the assistance apparatus according to the first aspect of the present disclosure.

An assistance method according to the second aspect of the present disclosure is an assistance method for assisting a movement of a user by using wires attached to a body of the user. The assistance method includes coupling, using a first wire among the wires, an upper-body belt and a left knee belt to each other on or above a front part of the body of the user, the upper-body belt being a belt to be worn on an upper half of the body of the user, the left knee belt being a belt to be worn on a left knee of the user; coupling, using a second wire among the wires, the upper-body belt and the left knee belt to each other on or above a back part of the body of the user; coupling, using a third wire among the wires, the upper-body belt and a right knee belt to each other on or above the front part of the body of the user, the right knee belt being a belt to be worn on a right knee of the user; coupling, using a fourth wire among the wires, the upper-body belt and the right knee belt to each other on or above the back part of the body of the user; when assisting the user in walking while carrying an object, generating a tension greater than or equal to a first threshold value in the first wire during a first period, the first period being a period of 35% or more and 90% or less of a gait phase of a left leg of the user; generating a tension greater than or equal to the first threshold value in the second wire during a second period, the second period being a period of 0% or more and 25% or less and 65% or more and less than 100% of the gait phase of the left leg; generating a tension greater than or equal to the first threshold value in the third wire during a third period, the third period being a period of 35% or more and 90% or less of a gait phase of a right leg of the user; generating a tension greater than or equal to the first threshold value in the fourth wire during a fourth period, the fourth period being a period of 0% or more and 25% or less and 65% or more and less than 100% of the gait phase of the right leg; acquiring information specifying a hand that carries the object; when the information indicates a left hand of the user, making the tension of the second wire in the second period and the tension of the third wire in the third period greater than the tension of the first wire in the first period and the tension of the fourth wire in the fourth period; and when the information indicates a right hand of the user, making the tension of the first wire in the first period and the tension of the fourth wire in the fourth period greater than the tension of the second wire in the second period and the tension of the third wire in the third period. The tension of the first wire, the tension of the second wire, the tension of the third wire, and the tension of the fourth wire are adjusted by a motor that is controlled by at least one control circuit. The assistance method according to the second aspect described above can achieve advantages similar to those of the assistance apparatus according to the second aspect of the present disclosure.

The assistance method according to the second aspect of the present disclosure may further include acquiring the information via an interface device.

In the assistance methods according to the first and second aspects of the present disclosure, the left leg may shift from a stance phase to a swing phase during the first period, the left leg may shift from the swing phase to the stance phase during the second period, the right leg may shift from the stance phase to the swing phase during the third period, and the right leg may shift from the swing phase to the stance phase during the fourth period.

In the assistance methods according to the first and second aspects of the present disclosure, a first end of the first wire may be fixed to the left knee belt, and a second end of the first wire may be fixed to a first motor among the at least one motor. A first end of the second wire may be fixed to the left knee belt, and a second end of the second wire may be fixed to a second motor among the at least one motor. A first end of the third wire may be fixed to the right knee belt, and a second end of the third wire may be fixed to a third motor among the at least one motor. A first end of the fourth wire may be fixed to the right knee belt, and a second end of the fourth wire may be fixed to a fourth motor among the at least one motor.

The assistance methods according to the first and second aspects of the present disclosure may further include coupling, using a fifth wire among the wires, the upper-body belt and the left knee belt to each other, the fifth wire extending on or above the front part of the body of the user in a direction crossing a direction in which the first wire extends; coupling, using a sixth wire among the wires, the upper-body belt and the left knee belt to each other, the sixth wire extending on or above the back part of the body of the user in a direction crossing a direction in which the second wire extends; coupling, using a seventh wire among the wires, the upper-body belt and the right knee belt to each other, the seventh wire extending on or above the front part of the body of the user in a direction crossing a direction in which the third wire extends; coupling, using an eighth wire among the wires, the upper-body belt and the right knee belt to each other, the eighth wire extending on or above the back part of the body of the user in a direction crossing a direction in which the fourth wire extends; when assisting the user in walking while carrying the object, generating a tension greater than or equal to the first threshold value in the first wire and the fifth wire during the first period; generating a tension greater than or equal to the first threshold value in the second wire and the sixth wire during the second period; generating a tension greater than or equal to the first threshold value in the third wire and the seventh wire during the third period; and generating a tension greater than or equal to the first threshold value in the fourth wire and the eighth wire during the fourth period.

In the assistance methods according to the first and second aspects of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance methods according to the first and second aspects of the present disclosure may further include acquiring a sensor value of a gait sensor that detects a gait cycle of the user; and calculating the gait phase of the left leg and the gait phase of the right leg based on the sensor value.

A recording medium according to the first aspect of the present disclosure is a recording medium storing a control program for causing a device including a processor to execute a process. The recording medium is a non-volatile, computer-readable medium. A first wire couples an upper-body belt and a left knee belt to each other on or above a front part of a body of a user, the upper-body belt being a belt to be worn on an upper half of the body of the user, the left knee belt being a belt to be worn on a left knee of the user. A second wire couples the upper-body belt and the left knee belt to each other on or above a back part of the body of the user. A third wire couples the upper-body belt and a right knee belt to each other on or above the front part of the body of the user, the right knee belt being a belt to be worn on a right knee of the user. A fourth wire couples the upper-body belt and the right knee belt to each other on or above the back part of the body of the user. The process includes, when assisting the user in walking while carrying an object, causing at least one motor to generate a tension greater than or equal to a first threshold value in the first wire during a first period, the first period being a period of 35% or more and 90% or less of a gait phase of a left leg of the user; causing the at least one motor to generate a tension greater than or equal to the first threshold value in the second wire during a second period, the second period being a period of 0% or more and 25% or less and 65% or more and less than 100% of the gait phase of the left leg; causing the at least one motor to generate a tension greater than or equal to the first threshold value in the third wire during a third period, the third period being a period of 35% or more and 90% or less of a gait phase of a right leg of the user; causing the at least one motor to generate a tension greater than or equal to the first threshold value in the fourth wire during a fourth period, the fourth period being a period of 0% or more and 25% or less and 65% or more and less than 100% of the gait phase of the right leg; acquiring a left sensor value from a left sensor attached to a left hand of the user; acquiring a right sensor value from a right sensor attached to a right hand of the user; detecting a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value; when the first condition is detected, making the tension of the second wire in the second period and the tension of the third wire in the third period greater than the tension of the first wire in the first period and the tension of the fourth wire in the fourth period; and when the second condition is detected, making the tension of the first wire in the first period and the tension of the fourth wire in the fourth period greater than the tension of the second wire in the second period and the tension of the third wire in the third period. The recording medium according to the first aspect described above can achieve advantages similar to those of the assistance apparatus according to the first aspect of the present disclosure.

A recording medium according to the second aspect of the present disclosure is a recording medium storing a control program for causing a device including a processor to execute a process. The recording medium is a non-volatile, computer-readable medium. A first wire couples an upper-body belt and a left knee belt to each other on or above a front part of a body of a user, the upper-body belt being a belt to be worn on an upper half of the body of the user, the left knee belt being a belt to be worn on a left knee of the user. A second wire couples the upper-body belt and the left knee belt to each other on or above a back part of the body of the user. A third wire couples the upper-body belt and a right knee belt to each other on or above the front part of the body of the user, the right knee belt being a belt to be worn on a right knee of the user. A fourth wire couples the upper-body belt and the right knee belt to each other on or above the back part of the body of the user. The process includes, when assisting the user in walking while carrying an object, causing at least one motor to generate a tension greater than or equal to a first threshold value in the first wire during a first period, the first period being a period of 35% or more and 90% or less of a gait phase of a left leg of the user; causing the at least one motor to generate a tension greater than or equal to the first threshold value in the second wire during a second period, the second period being a period of 0% or more and 25% or less and 65% or more and less than 100% of the gait phase of the left leg; causing the at least one motor to generate a tension greater than or equal to the first threshold value in the third wire during a third period, the third period being a period of 35% or more and 90% or less of a gait phase of a right leg of the user; causing the at least one motor to generate a tension greater than or equal to the first threshold value in the fourth wire during a fourth period, the fourth period being a period of 0% or more and 25% or less and 65% or more and less than 100% of the gait phase of the right leg; acquiring information specifying a hand that carries the object; when the information indicates a left hand of the user, making the tension of the second wire in the second period and the tension of the third wire in the third period greater than the tension of the first wire in the first period and the tension of the fourth wire in the fourth period; and when the information indicates a right hand of the user, making the tension of the first wire in the first period and the tension of the fourth wire in the fourth period greater than the tension of the second wire in the second period and the tension of the third wire in the third period. The recording medium according to the second aspect described above can achieve advantages similar to those of the assistance apparatus according to the second aspect of the present disclosure.

It should be noted that the general or specific aspects described above may be implemented as a system, an apparatus, a method, an integrated circuit, a computer program, or a computer-readable recording medium such as a recording disc, or any selective combination thereof. Examples of the computer-readable recording medium include a non-volatile recording medium such as a CD-ROM.

Embodiment

The following specifically describes an assistance apparatus and so on according to an embodiment of the present disclosure with reference to the drawings. The following embodiment describes general or specific examples. Numerical values, shapes, constituent elements, arrangement positions and connection forms of the constituent elements, steps, the order of the steps, and so on in the following embodiment are merely examples and are not intended to limit the present disclosure. The constituent elements mentioned in the following embodiment are described as optional constituent elements unless they are specified in independent claims that define the present disclosure in its broadest concept. The following description of the embodiment may include expressions with the term "approximately", such as approximately parallel or approximately perpendicular. For example, the expression "approximately parallel" is used to mean not only the state of being exactly parallel but also the state of being substantially parallel, that is, the state of being parallel with an error of several percent, for example. This also applies to other expressions with "approximately". In addition, the drawings are illustrative and are not to scale. In the drawings, substantially the same constituent elements are given the same numerals and will not be repeatedly described or will be described in brief.

In this embodiment, an assistance apparatus 100 will be described as an assistance apparatus that assists a user wearing the assistance apparatus 100 in walking. Specifically, the assistance apparatus 100 according to the embodiment will be described as an assistance apparatus that actively supports flexion and extension of the hip joints of the user to allow the user to walk. In this embodiment, the term "actively supporting" may refer not only to supporting flexion and extension forces, which are required for the hip joints, during flexion and extension of the hip joints of the user to walk in the direction of travel but also to applying a force for causing flexion and extension of the hip joints and to physically controlling the amount of flexion and extension of the hip joints to the desired amount of flexion and extension, that is, physically controlling movements of the hip joints of the user. As used herein, the term "assisting the user" by the assistance apparatus 100 is used to include both actively supporting the movement of the user and supporting the movement of the user in an auxiliary manner.

1. Configuration of Assistance Apparatus According to Embodiment

Figure 2:
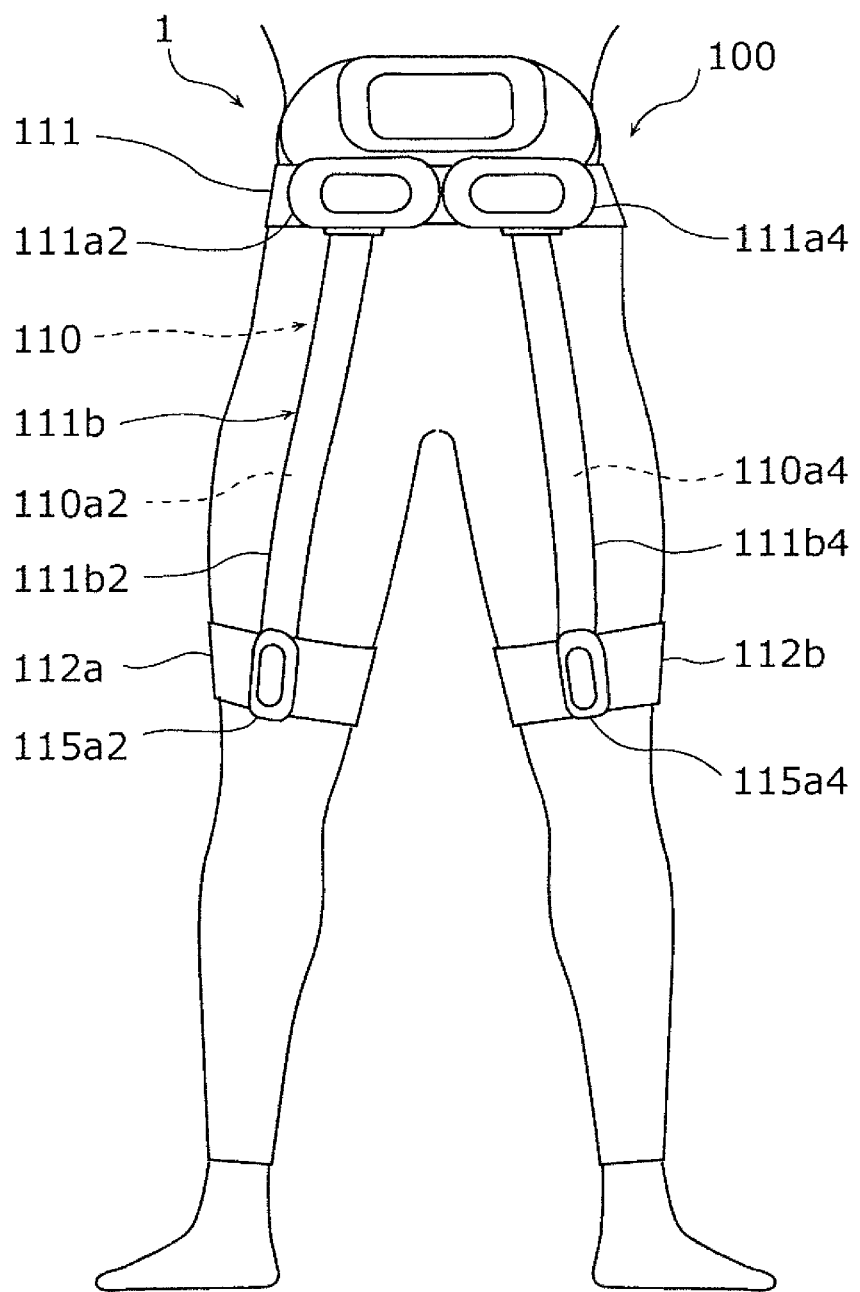
FIG. 2 is a back view of the user wearing the assistance apparatus illustrated in FIG. 1.
Figure 3:
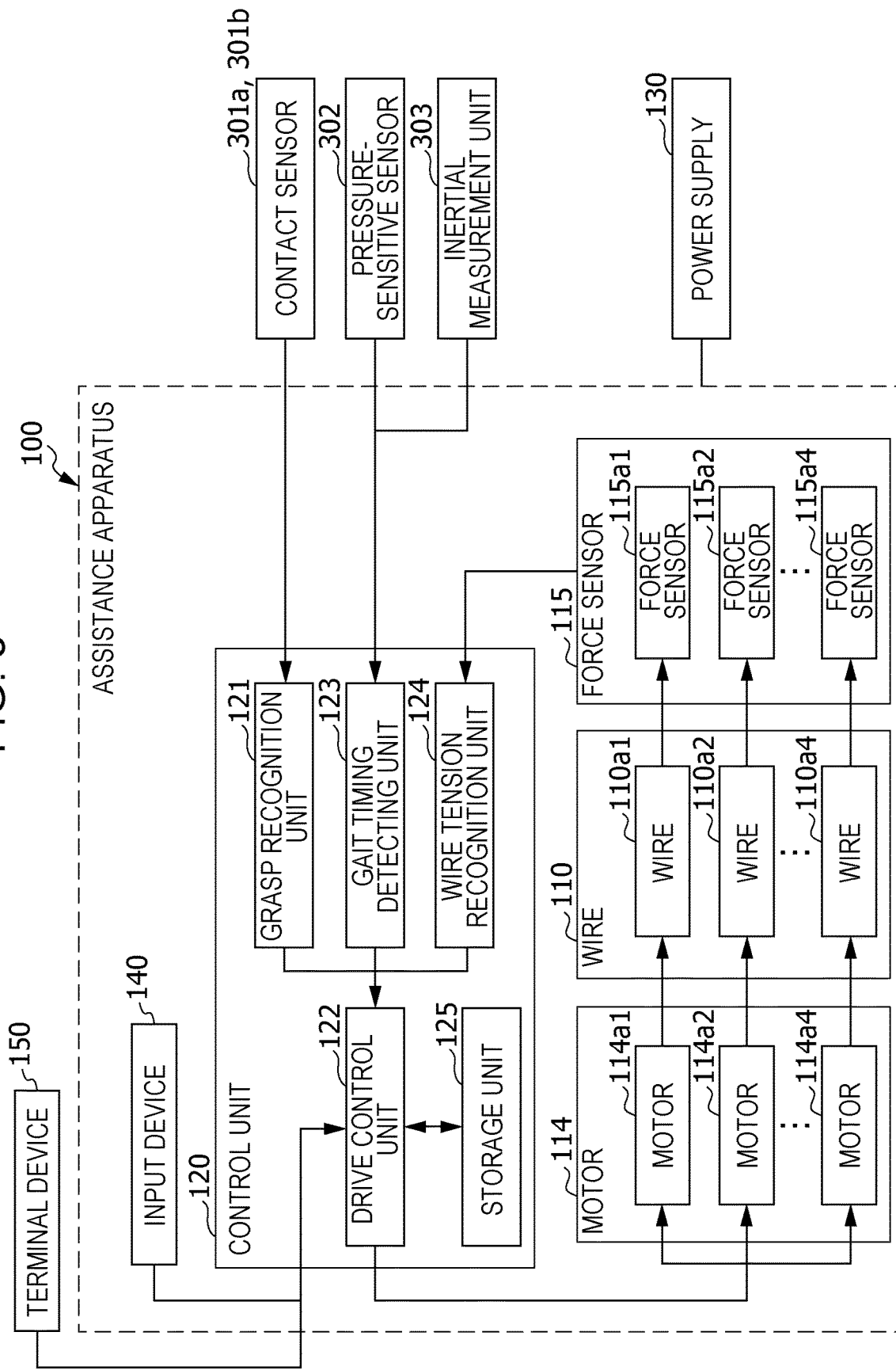
FIG. 3 is a block diagram illustrating a functional configuration of the assistance apparatus according to the embodiment.

The assistance apparatus 100 according to the embodiment will be described with reference to FIG. 1 to FIG. 3. FIG. 1 is a front view of a user 1 wearing the assistance apparatus 100 according to the embodiment, as viewed from the front. FIG. 2 is a back view of the user 1 wearing the assistance apparatus 100 illustrated in FIG. 1. FIG. 3 is a block diagram illustrating a functional configuration of the assistance apparatus 100 according to the embodiment.

As illustrated in FIG. 1 to FIG. 3, the assistance apparatus 100 includes an upper-body belt 111, a left knee belt 112a, a right knee belt 112b, and wires 110. The assistance apparatus 100 further includes motors 114, force sensors 115, and a control unit 120 that controls the operation of the motors 114. The assistance apparatus 100 may include a power supply 130 for supplying electric power to the motors 114 and so on. The power supply 130 may be, for example, a primary battery, a secondary battery, or the like.

The wires 110 include wires 110a1 to 110a4. Each of the wires 110 is coupled to the upper-body belt 111 and the left knee belt 112a or coupled to the upper-body belt 111 and the right knee belt 112b.

The motors 114 include motors 114a1 to 114a4. The wire 110a1 is coupled to the motor 114a1. The wire 110a2 is coupled to the motor 114a2. The wire 110a3 is coupled to the motor 114a3. The wire 110a4 is coupled to the motor 114a4.

The force sensors 115 include force sensors 115a1 to 115a4. The force sensor 115a1 is disposed on the wire 110a1. The force sensor 115a2 is disposed on the wire 110a2. The force sensor 115a3 is disposed on the wire 110a3. The force sensor 115a4 is disposed on the wire 110a4.

The upper-body belt 111 is worn on the upper half of the body of the user 1. The upper-body belt 111 has a band shape, for example. The upper-body belt 111 includes, near an end portion thereof, a fixing member. Examples of the fixing member include a hook-and-loop fastener such as a Velcro (registered trademark) tape, a fastener such as a hook or a buckle, and a tape. For example, the upper-body belt 111 is wrapped around the waist of the user 1 and is kept wrapped around the waist of the user 1 by using the fixing member. Thus, the upper-body belt 111 is worn on the waist of the user 1. The fixing position of the fixing member is adjusted to change the inner diameter of the wrapped upper-body belt 111. Since the length of the upper-body belt 111 can be adjusted, various users 1 with different waist circumferences can wear the upper-body belt 111. The upper-body belt 111 is made of a non-extensible material, for example. Thus, the upper-body belt 111 is less deformable when pulled by the wires 110. The term "upper half of the body", as used herein, is used to include a portion of the body of the user from the shoulder to the waist. The upper-body belt 111 illustrated in FIG. 1 and FIG. 2 has a configuration of a waist belt to be worn on the waist of the user 1. The upper-body belt 111 may be worn on, for example, the waist of the user 1 and/or the shoulder of the user 1 and/or the chest of the user 1.

The upper-body belt 111 may have a tubular shape. In this case, the tubular-shaped upper-body belt 111 may have a larger circumference than the waist circumference of the user 1. The upper-body belt 111 has an adjustment mechanism for adjusting the length of the upper-body belt 111 so that the upper-body belt 111 fits the waist of the user 1. The adjustment mechanism is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the upper-body belt 111 folds back at the portion of the hook-and-loop fastener, and the inner diameter of the tube formed by the upper-body belt 111 changes in accordance with the amount of fold-back.

The left knee belt 112a is worn on the left leg of the user 1 in the vicinity of the left knee, and the right knee belt 112b is worn on the right leg of the user 1 in the vicinity of the right knee. The left knee belt 112a may be worn on any portion of the left leg in a region extending from below the knee to the thigh. The right knee belt 112b may be worn on any portion of the right leg in a region extending from below the knee to the thigh. That is, the term "knee", as used herein, may be used to include a region extending from below the knee to the thigh.

Each of the knee belts 112a and 112b has a band shape, for example, and includes, near an end portion thereof, a fixing member. The knee belts 112a and 112b are the knee left belt 112a and the right knee belt 112b. Examples of the fixing member include a hook-and-loop fastener such as a Velcro (registered trademark) tape, a fastener such as a hook or a buckle, and a tape. Each of the knee belts 112a and 112b is worn on a corresponding one of the thighs of the user 1 or above a corresponding one of the knees of the user 1. For example, each of the knee belts 112a and 112b is wrapped around the corresponding one of the thighs or the like of the user 1 and is kept wrapped around the corresponding one of the thighs or the like of the user 1 by using the fixing member. Thus, the knee belts 112a and 112b are worn on the thighs or the like of the user 1. The fixing positions of the fixing members are adjusted to change the respective inner diameters of the wrapped knee belts 112a and 112b. Since the lengths of the knee belts 112a and 112b can be adjusted, various users 1 having different leg circumferences can wear the knee belts 112a and 112b. The knee belts 112a and 112b may not necessarily be worn over the knee joints. The human thigh has a feature in that the diameter of the thigh becomes larger gradually from the knee toward the hip. Thus, the knee belts 112a and 112b, which are worn on the thighs, namely, above the knees, slip just a little even under tensile forces of the wires 110 when the knee belts 112a and 112b are tightly fastened. In addition, the knee belts 112a and 112b are made of a non-extensible material, for example. Thus, the knee belts 112a and 112b are less deformable when pulled by the wires 110.

Each of the knee belts 112a and 112b may have a tubular shape. In this case, the tubular-shaped knee belts 112a and 112b may have larger circumferences than the thighs of the user 1. The knee belts 112a and 112b have each an adjustment mechanism for adjusting the length of the corresponding one of the knee belts 112a and 112b so that the knee belts 112a and 112b fit the thighs or the like of the user 1. Each of the adjustment mechanisms is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the knee belts 112*a* and 112*b* each fold back at the portion of the hook-and-loop fastener, and the inner diameter of the tube formed by each of the knee belts 112*a* and 112*b* changes in accordance with the amount of fold-back.

The motors 114 are arranged on the upper-body belt 111 in a fixed manner. In this embodiment, the motors 114 include four motors 114*a*1 to 114*a*4. For example, the motors 114*a*1 to 114*a*4 may be accommodated in hollow containers 111*a*1 to 111*a*4 included in the upper-body belt 111, respectively. The containers 111*a*1 to 111*a*4 may be integrated with the upper-body belt 111 or may be removably attached to the upper-body belt 111. The containers 111*a*1 to 111*a*4 may be disposed in the manner illustrated in FIG. 1 and FIG. 2. In the example illustrated in FIG. 1 and FIG. 2, the containers 111*a*1, 111*a*2, 111*a*3, and 111*a*4 are located on the left side of the front part, the left side of the back part, the right side of the front part, and the right side of the back part of the body of the user 1, respectively. The motors 114*a*1, 114*a*2, 114*a*3, and 114*a*4 are accommodated in the containers 111*a*1, 111*a*2, 111*a*3, and 111*a*4, respectively. The motor 114*a*1 changes the length of the wire 110*a*1 between the upper-body belt 111 and the left knee belt 112*a* to adjust the tension of the wire 110*a*1. The motor 114*a*2 changes the length of the wire 110*a*2 between the upper-body belt 111 and the left knee belt 112*a* to adjust the tension of the wire 110*a*2. The motor 114*a*3 changes the length of the wire 110*a*3 between the upper-body belt 111 and the right knee belt 112*b* to adjust the tension of the wire 110*a*3. The motor 114*a*4 changes the length of the wire 110*a*4 between the upper-body belt 111 and the right knee belt 112*b* to adjust the tension of the wire 110*a*4.

In this embodiment, each of the motors 114*a*1 to 114*a*4 includes a pulley, a drive shaft for rotating the pulley, and an electric motor for driving the drive shaft to rotate. The pulley of each of the motors 114*a*1 to 114*a*4 has a corresponding wire among the wires 110*a*1 to 110*a*4 wound therearound. The motors 114*a*1 to 114*a*4 and the wires 110*a*1 to 110*a*4 have a one-to-one correspondence. The respective pulleys, drive shafts, and electric motors of the motors 114*a*1 to 114*a*4 are accommodated in the containers 111*a*1 to 111*a*4, respectively. Each of the motors 114*a*1 to 114*a*4 may include an electric motor, but may include no pulley or drive shaft. Alternatively, the upper-body belt 111 may include pulleys and drive shafts, each pulley and drive shaft being associated with one of the motors 114*a*1 to 114*a*4. In this case, a rotating shaft of the electric motor is coupled to the drive shaft for the pulley in such a manner that a rotational driving force can be transmitted to the drive shaft. Instead of the motors 114*a*1 to 114*a*4, for example, a device capable of adjusting the lengths of the wires 110*a*1 and 110*a*2 between the upper-body belt 111 and the left knee belts 112*a* and the lengths of the wires 110*a*3 and 110*a*4 between the upper-body belt 111 and the right knee belt 112*b*, such as a linear actuator or a pneumatic or hydraulic piston, may be used. In the assistance apparatus 100 having the configuration described above, the wound portions of the wires 110*a*1 to 110*a*4 and the motors 114*a*1 to 114*a*4 are located on the upper-body belt 111, and the wires 110*a*1 to 110*a*4 and the knee belts 112*a* and 112*b* are located below the upper-body belt 111. Accordingly, the assistance apparatus 100 achieves a simple and compact configuration.

In this embodiment, the wires 110 include four wires 110*a*1 to 110*a*4. The motor 114*a*1 is coupled to the wire 110*a*1, the motor 114*a*2 is coupled to the wire 110*a*2, the motor 114*a*3 is coupled to the wire 110*a*3, and the motor 114*a*4 is coupled to the wire 110*a*4 so as to individually adjust the lengths of the wires 110*a*1 to 110*a*4.

Each of the wires 110*a*1 and 110*a*2 has one end fixed to the left knee belt 112*a*. The wire 110*a*1 has another end coupled to the motor 114*a*1, and the wire 110*a*2 has another end coupled to the motor 114*a*2. That is, the other end of the wire 110*a*1 and the other end of the wire 110*a*2 are fixed. The wire 110*a*1 couples the left knee belt 112*a* and the motor 114*a*1 to each other, and the wire 110*a*2 couples the left knee belt 112*a* and the motor 114*a*2 to each other.

Each of the wires 110*a*3 and 110*a*4 has one end fixed to the right knee belt 112*b*. The wire 110*a*3 has another end coupled to the motor 114*a*3, and the wire 110*a*4 has another end coupled to the motor 114*a*4. That is, the other end of the wire 110*a*3 and the other end of the wire 110*a*4 are fixed. The wire 110*a*3 couples the right knee belt 112*b* and the motor 114*a*3 to each other, and the wire 110*a*4 couples the right knee belt 112*b* and the motor 114*a*4 to each other.

In this embodiment, each of the motors 114*a*1 to 114*a*4 rotates the pulley in the forward or reverse direction to wind or unwind the corresponding wire among the wires 110*a*1 to the 110*a*4 around the pulley. The wires 110*a*1 to 110*a*4 described above are fixed to the waist of the user 1 by the upper-body belt 111 and are fixed to the left and right thighs or the like of the user 1 by the knee belts 112*a* and 112*b*.

As described above, each of the wires 110*a*1 to 110*a*4 couples the upper-body belt 111 to the left knee belt 112*a* or the right knee belt 112*b*. The wires 110*a*1 to 110*a*4 may be coupled to the upper-body belt 111 directly or indirectly. Each of the wires 110*a*1 to 110*a*4 may be coupled to the left knee belt 112*a* or the right knee belt 112*b* directly or indirectly. In the example described above, the one end of each of the wires 110*a*1 to 110*a*4 is fixed to, or is directly coupled to, the left knee belt 112*a* or the right knee belt 112*b*, and the other end of each of the wires 110*a*1 to 110*a*4 is fixed to, or is indirectly coupled to, the upper-body belt 111 via the corresponding one of the motors 114. However, each of the wires 110 may be coupled to the upper-body belt 111 and each of the wires 110 may be coupled to the left knee belt 112*a* or the right knee belt 112*b* by using the following configuration, for example.

Specifically, the one end of each of the wires 110 may be indirectly coupled to the left knee belt 112*a* or the right knee belt 112*b* via the corresponding one of the motors 114, and the other end of each of the wires 110 may be directly coupled to the upper-body belt 111. Alternatively, both ends of each of the wires 110 may be directly coupled to the upper-body belt 111 and to the left knee belt 112*a* or the right knee belt 112*b*, and a motor, a linear actuator, or a pneumatic or hydraulic piston may be disposed in the middle of each of the wires 110 to adjust the length of the wire 110.

Alternatively, the one end of each of the wires 110 may be directly coupled to the left knee belt 112*a* or the right knee belt 112*b*, and the other end of each of the wires 110 may be indirectly coupled to the left knee belt 112*a* or the right knee belt 112*b* via the corresponding one of the motors 114 in such a manner that each of the wires 110 is arranged to reciprocate between the left knee belt 112*a* or the right knee belt 112*b* and the upper-body belt 111. Alternatively, the one end of each of the wires 110 may be directly coupled to the upper-body belt 111, and the other end of each of the wires 110 may be indirectly coupled to the upper-body belt 111 via the corresponding one of the motors 114 in such a manner that each of the wires 110 is arranged to reciprocate between the upper-body belt 111 and the left knee belt 112a or the right knee belt 112b.

Alternatively, both ends of each of the wires 110 may be coupled to the corresponding one of the motors 114 and may be arranged to form a ring through the motor 114. In this case, each of the wires 110 is arranged to reciprocate between the upper-body belt 111 and the left knee belt 112a or the right knee belt 112b, and each of the motors 114 changes the length of the circumference of the ring of the corresponding one of the wires 110.

In any of the configurations described above, each of the wires 110 is coupled to the upper-body belt 111 and the left knee belt 112a or the right knee belt 112b so that the tension thereof is supported by the upper-body belt 111 and the left knee belt 112a or the right knee belt 112b. Thus, when each of the motors 114a1 to 114a4 pulls the corresponding wire among the wires 110, tension that causes the upper-body belt 111 and the left knee belt 112a or the right knee belt 112b to come into close proximity to each other is generated in the corresponding wire.

The force sensors 115 include four force sensors 115a1 to 115a4. The force sensor 115a1 detects the tension of the wire 110a1 and outputs the detected tension to the control unit 120. The force sensor 115a2 detects the tension of the wire 110a2 and outputs the detected tension to the control unit 120. The force sensor 115a3 detects the tension of the wire 110a3 and outputs the detected tension to the control unit 120. The force sensor 115a4 detects the tension of the wire 110a4 and outputs the detected tension to the control unit 120. The force sensor 115a1 is disposed on the wire 110a1 in the left knee belt 112a. The force sensor 115a2 is disposed on the wire 110a2 in the left knee belt 112a. The force sensor 115a3 is disposed on the wire 110a3 in the right knee belt 112b. The force sensor 115a4 is disposed on the wire 110a4 in the right knee belt 112b. The force sensors 115a1 to 115a4 may be located in the upper-body belt 111. Each of the force sensors 115a1 to 115a4 may be capable of detecting the tension of the corresponding wire among the wires 110a1 to 110a4, and may be a strain gauge force sensor or a piezoelectric force sensor, for example. The force sensors 115a1 to 115a4 and the wires 110a1 to 110a4 have a one-to-one correspondence.

Each of the wires 110a1 to 110a4 may be a metallic wire or a non-metallic wire. Examples of the non-metallic wire include a fiber wire and a fiber belt. A fiber wire or fiber belt is made of a material such as polyester fiber, nylon fiber, acrylic fiber, para-aramid fiber, ultrahigh molecular weight polyethylene fiber, poly-p-phenylenebenzobisoxazole (PBO) fiber, polyarylate fiber, or carbon fiber. In this embodiment, four coupling belts 111b1 to 111b4 are arranged along the wires 110a1 to 110a4, respectively, and each of the coupling belts 111b1 to 111b4 extends from the upper-body belt 111 to the left knee belt 112a or the right knee belt 112b. The coupling belts 111b1 to 111b4 and the wires 110a1 to 110a4 have a one-to-one correspondence. As a non-limiting example, the coupling belts 111b1 to 111b4 are each integrated with the upper-body belt 111 and the left knee belt 112a or the right knee belt 112b and are made of a material similar to that of the belts 111, 112a, and 112b. For example, the upper-body belt 111, the knee belts 112a and 112b, and the coupling belts 111b1 to 111b4 may form a single suit having an assistance function that is wearable by the user 1. Each of the coupling belts 111b1 to 111b4 contains and covers the corresponding wire among the wires 110a1 to 110a4. The coupling belts 111b1 to 111b4 may be collectively referred to as coupling belts 111b.

Figure 4:
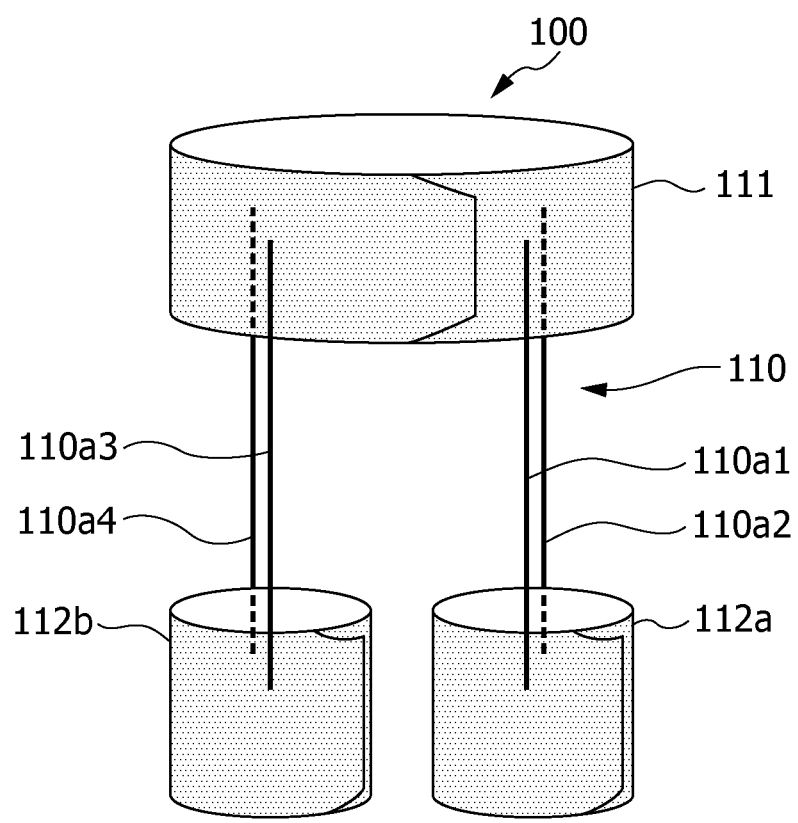
FIG. 4 is a diagram schematically illustrating the arrangement of constituent elements of the assistance apparatus illustrated in FIG. 1.

The arrangement configuration of the wires 110a1 to 110a4 will be described in detail with reference to FIG. 1, FIG. 2, and FIG. 4. FIG. 4 schematically illustrates the arrangement of the constituent elements of the assistance apparatus 100 illustrated in FIG. 1. The wire 110a1 couples the upper-body belt 111 and the left knee belt 112a to each other via the motor 114a1 on or above the front part of the body of the user 1. The wire 110a1 extends upward from the left knee belt 112a on or above the front part of the body of the user 1. The wire 110a2 couples the upper-body belt 111 and the left knee belt 112a to each other via the motor 114a2 on or above the back part of the body of the user 1. The wire 110a2 extends upward from the left knee belt 112a on or above the back part of the body of the user 1. The wire 110a3 couples the upper-body belt 111 and the right knee belt 112b to each other via the motor 114a3 on or above the front part of the body of the user 1. The wire 110a3 extends upward from the right knee belt 112b on or above the front part of the body of the user 1. The wire 110a4 couples the upper-body belt 111 and the right knee belt 112b to each other via the motor 114a4 on or above the back part of the body of the user 1. The wire 110a4 extends upward from the right knee belt 112b on or above the back part of the body of the user 1. In this manner, the wire 110a1 is located on or above the front part of the left leg of the user 1, the wire 110a2 is located on or above the back part of the left leg of the user 1, the wire 110a3 is located on or above the front part of the right leg of the user 1, and the wire 110a4 is located on or above the back part of the right leg of the user 1. The wires 110a1 to 110a4 are pulled individually to apply forces in different directions to the left and right legs.

In the example illustrated in FIG. 1, FIG. 2, and FIG. 4, the wires 110a1 and 110a3 do not cross each other on or above the front part of the body of the user 1. However, the wires 110a1 and 110a3 may cross each other on or above the front part of the body of the user 1. In the example illustrated in FIG. 1, FIG. 2, and FIG. 4, the wires 110a2 and 110a4 do not cross each other on or above the back part of the body of the user 1. However, the wires 110a2 and 110a4 may cross each other on or above the back part of the body of the user 1.

The motors 114a1 to 114a4 pull the wires 110a1 to 110a4 to apply tensions to the wires 110a1 to 110a4, respectively, and the tensions are transmitted to the left and right legs of the user 1 via the upper-body belt 111 and the knee belts 112a and 112b. To effectively transmit the tensions of the wires 110a1 to 110a4 to the left and right legs of the user 1, the upper-body belt 111 and the knee belts 112a and 112b may have rigidity so as not to be deformable and have inflexibility so as not to be extensible. As described above, examples of the material of the upper-body belt 111 and the knee belts 112a and 112b include a non-extensible material. The upper-body belt 111 and the knee belts 112a and 112b described above are worn by the user 1 in such a manner as to tightly fit the body of the user 1, thus efficiently transmitting the driving forces of the motors 114a1 to 114a4 to the legs of the user 1 through the wires 110a1 to 110a4 and effectively assisting movements of the legs of the user 1. The term "assisting", as used herein, is used to include supporting the movement of the user in order to allow the user to perform a predetermined motion and forcing the body of the user to perform the predetermined motion to induce movements of the body.

Figure 5:
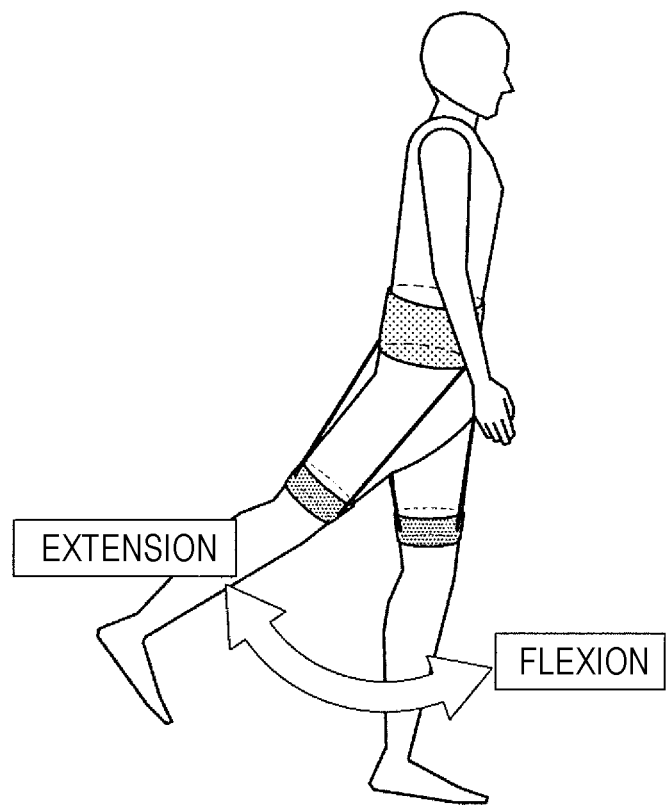
FIG. 5 is a diagram illustrating example motions of the right leg of the user, which are assisted by the assistance apparatus.

A further description will be given of a relationship between tensions applied to the wires 110a1 to 110a4 by the assistance apparatus 100 and motions of the user that are assisted with the tensions. For example, FIG. 5 illustrates example motions of the right leg of the user, which are assisted by the assistance apparatus 100. In the example illustrated in FIG. 5, the assistance apparatus 100 applies an assistance force to the right leg during the swing phase of gait. The assistance apparatus 100 may apply an assistance force to the right leg during the stance phase of gait. The assistance apparatus 100 also enables the left leg of the user to perform motions similar to those of the right leg. As illustrated in FIG. 5, the assistance apparatus 100 can apply an assistance force for flexion and extension to the hip joint of the right leg of the user. The flexion of the hip joint is a motion of moving the thigh forward, and the extension of the hip joint is a motion of moving the thigh backward.

Figure 6A:
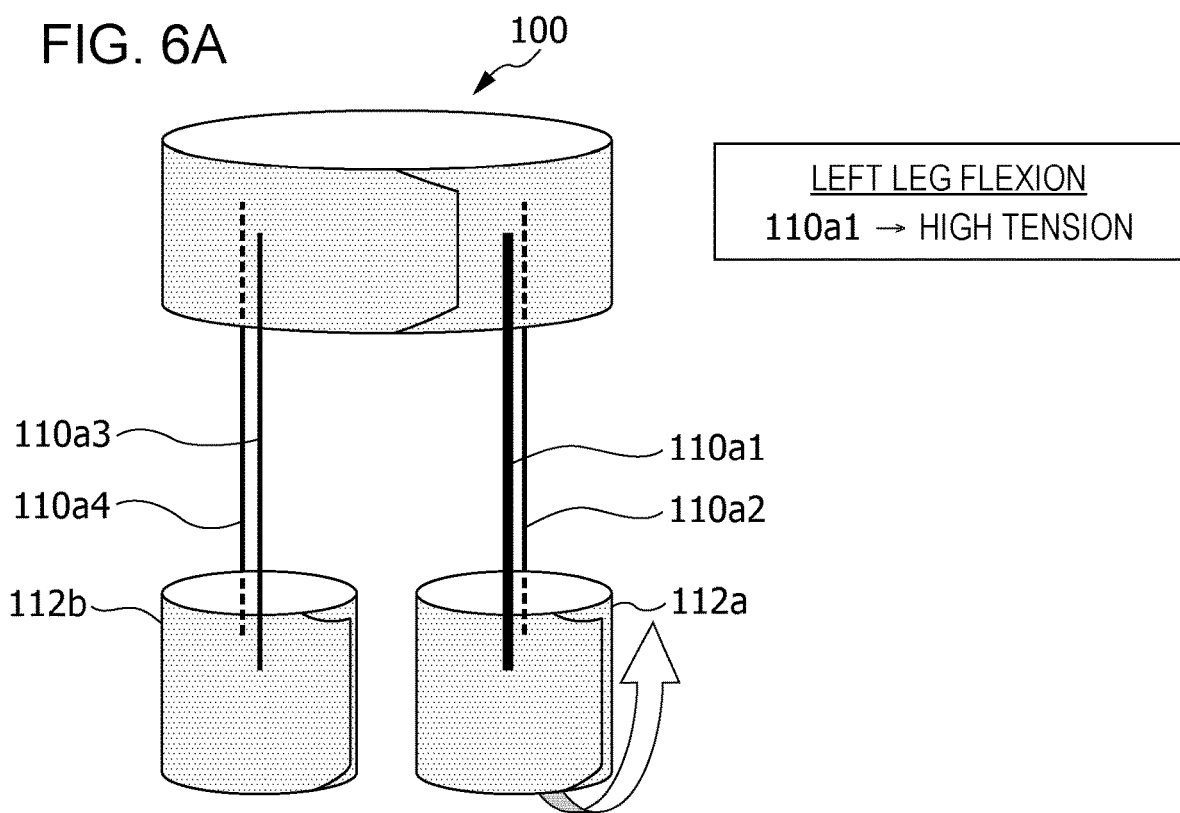
FIG. 6A is a diagram illustrating a case where the assistance apparatus according to the embodiment assists flexion of the hip joint of the left leg of the user.
Figure 6B:
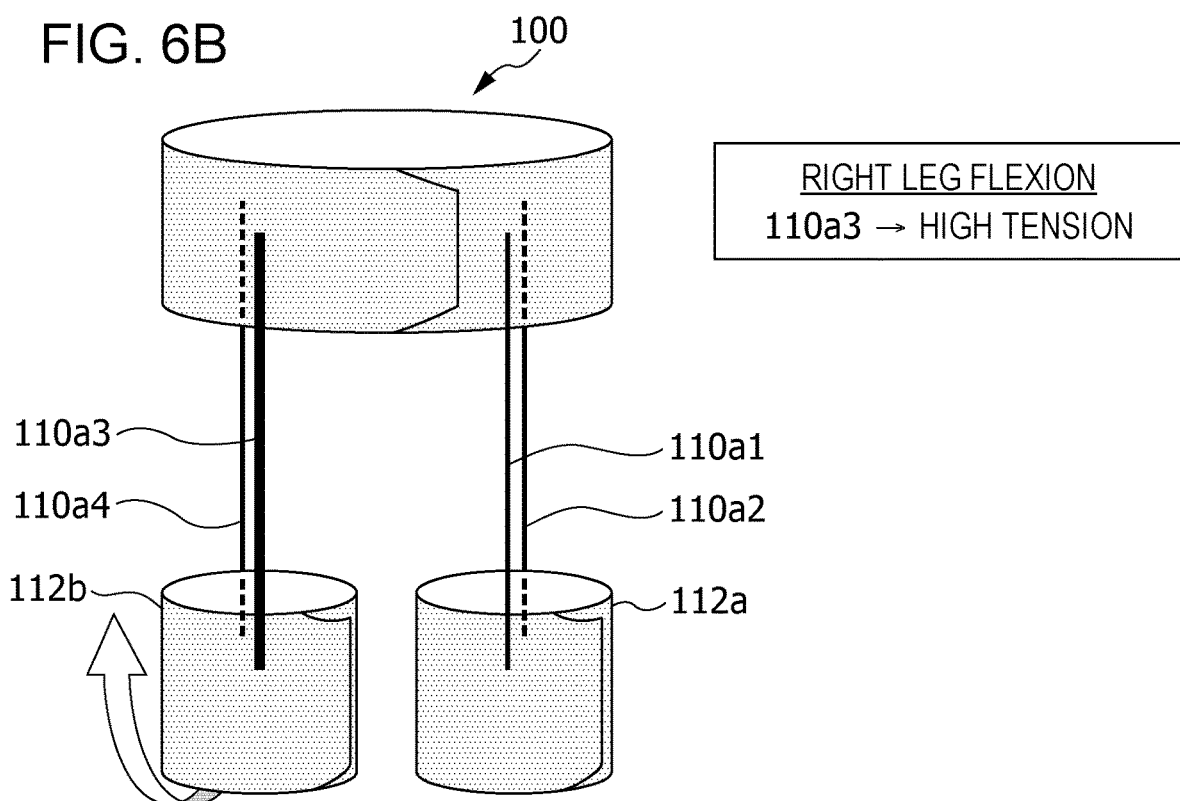
FIG. 6B is a diagram illustrating a case where the assistance apparatus according to the embodiment assists flexion of the hip joint of the right leg of the user.

Further, a relationship between motions of the user, which are induced, or assisted, by the assistance apparatus 100, and assistance forces given to the user through the wires 110$a$1 to 110$a$4 will be described with reference to FIG. 6A to FIG. 7B. FIG. 6A illustrates a case where the assistance apparatus 100 according to the embodiment assists flexion of the hip joint of the left leg of the user, and FIG. 6B illustrates a case where the assistance apparatus 100 according to the embodiment assists flexion of the hip joint of the right leg of the user. In FIG. 6A, to flex the left leg, the control unit 120 drives the motor 114$a$1 to increase the tension of the wire 110$a$1, that is, to generate a tension in the wire 110$a$1. In FIG. 6B, to flex the right leg, the control unit 120 drives the motor 114$a$3 to increase the tension of the wire 110$a$3. The control unit 120 may control the tensions of the wires 110 in accordance with the detection results of the force sensors 115$a$1 to 115$a$4 or in accordance with the amount of driving of the motors 114$a$1 to 114$a$4. The details of the control unit 120 will be described below.

In this embodiment, as a non-limiting example, a tension is applied to each of the wires 110$a$1 to 110$a$4 in a normal state before flexion. The tension may be applied so as to prevent the corresponding one of the wires 110$a$1 to 110$a$4 from loosening and may be less than or equal to 10 N or less than or equal to 5 N, for example. To flex the left leg and the right leg, the tensions of the wires 110$a$1 and 110$a$3 are each increased to, for example, a value greater than or equal to 40 N and less than or equal to 100 N. An example for the left leg will be described. A tension greater than or equal to 40 N is exerted on the wire 110$a$1 for a user, who is a healthy adult male in 20s to 40s. At this time, the user is able to clearly recognize that a force in a flexing direction acts on the left leg and promotes flexion of the left leg. When a tension over 80 N is exerted on the wire 110$a$1, the left leg of the user is raised in the flexing direction. When the tension exerted on the wire 110$a$1 is less than or equal to 20 N, the user continues the current motion without substantially perceiving the resistance caused by the tension of the wire 110$a$1. The tension values described above are examples. The tension values may be changed, as desired, in accordance with the age, gender, body size, or physical activity level of the user, the type of motion of the leg, the degree of assistance on the leg, and so on.

Figure 7A:
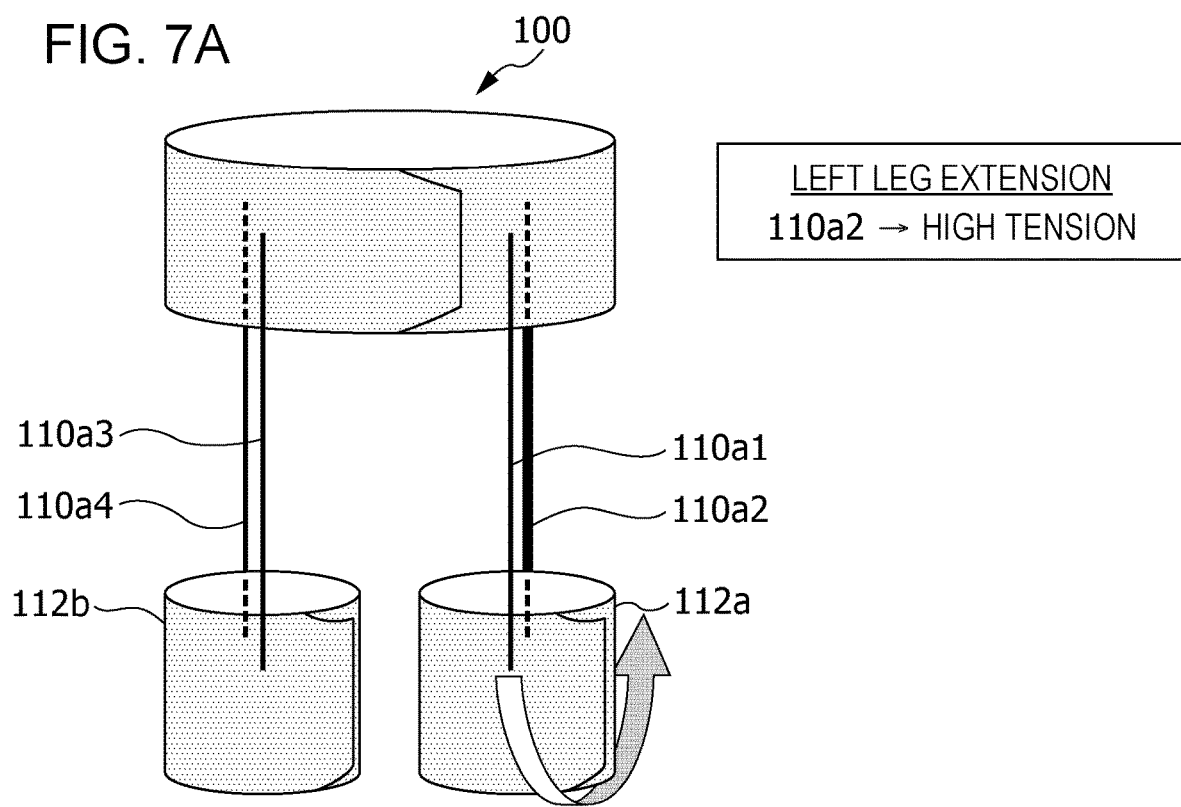
FIG. 7A is a diagram illustrating a case where the assistance apparatus according to the embodiment assists extension of the hip joint of the left leg of the user.
Figure 7B:
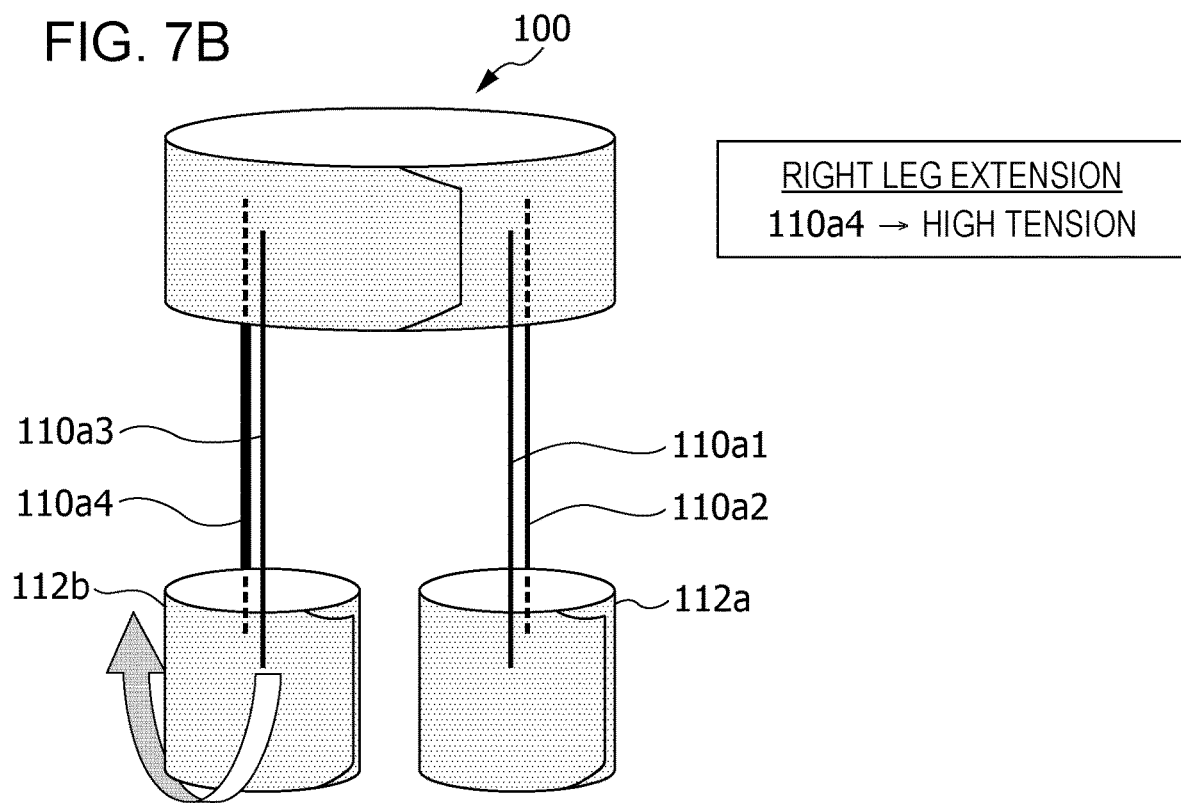
FIG. 7B is a diagram illustrating a case where the assistance apparatus according to the embodiment assists extension of the hip joint of the right leg of the user.

FIG. 7A and FIG. 7B illustrate cases where the assistance apparatus 100 according to the embodiment assists extension of the hip joints of the left and right legs of the user, respectively. In FIG. 7A, the control unit 120 increases the tension of the wire 110$a$2 to extend the left leg. In FIG. 7B, the control unit 120 increases the tension of the wire 110$a$4 to extend the right leg. The tensions of the wires 110 during extension may be similar to those during flexion.

In the foregoing description, the control unit 120 increases the tension of one wire to assist one motion of one leg. At this time, the control unit 120 may control the motors corresponding to the other three wires in accordance with the motion of the user so that the tensions of the other three wires are kept in the current states, and adjust the tensions of the other three wires. The control unit 120 may control the motors corresponding to the other three wires so as not to exert tension on the three wires. For example, the control unit 120 may stop the operation of the motors corresponding to the other three wires.

The assistance apparatus 100 described above is capable of assisting the user in walking by applying assistance torques, which are assistance forces in flexing and extending directions, to the user in accordance with torques generated during the stance phase and swing phase of the leg of the user while the user is walking.

Further, the configuration of the control unit 120 of the assistance apparatus 100 will be described with reference to FIG. 3. The control unit 120 controls the overall operation of the assistance apparatus 100. The control unit 120 determines operations to be individually applied to the wires 110$a$1 to 110$a$4 and controls assistance for the hip joints of the user 1. The operations to be individually applied to the wires 110$a$1 to 110$a$4 are operation patterns of the wires 110$a$1 to 110$a$4, including the timings of applying tensions to the wires 110$a$1 to 110$a$4, the magnitudes of the tensions, and periods during which the tensions are applied.

The control unit 120 acquires an instruction entered by the user 1 or the like from an input device 140 included in the assistance apparatus 100 or from a terminal device 150 external to the assistance apparatus 100, and controls the assistance apparatus 100 to start and stop assistance in accordance with the acquired instruction. The input device 140 of the assistance apparatus 100 may be a button, a switch, a key, a touch pad, a microphone of an audio recognition device, or any other suitable device. The terminal device 150 may be a terminal device carried by the user 1 wearing the assistance apparatus 100, and examples of the terminal device 150 include a smartphone, a smartwatch, a tablet, and a personal computer. The control unit 120 may communicate with the input device 140 and the terminal device 150 in a wired or wireless way. The wireless communication may be implemented using a wireless local area network (LAN) such as wireless fidelity (Wi-Fi (registered trademark)), or may be short-range wireless communication such as Bluetooth (registered trademark) or ZigBee (registered trademark), or any other type of wireless communication. The wired communication may be any existing wired communication. The control unit 120 may include a wired or wireless communication circuit. The wired or wireless communication circuit included in the assistance apparatus 100 may be used to perform wired communication or wireless communication. The input device 140 and the terminal device 150 are examples of an interface device.

Figure 8:
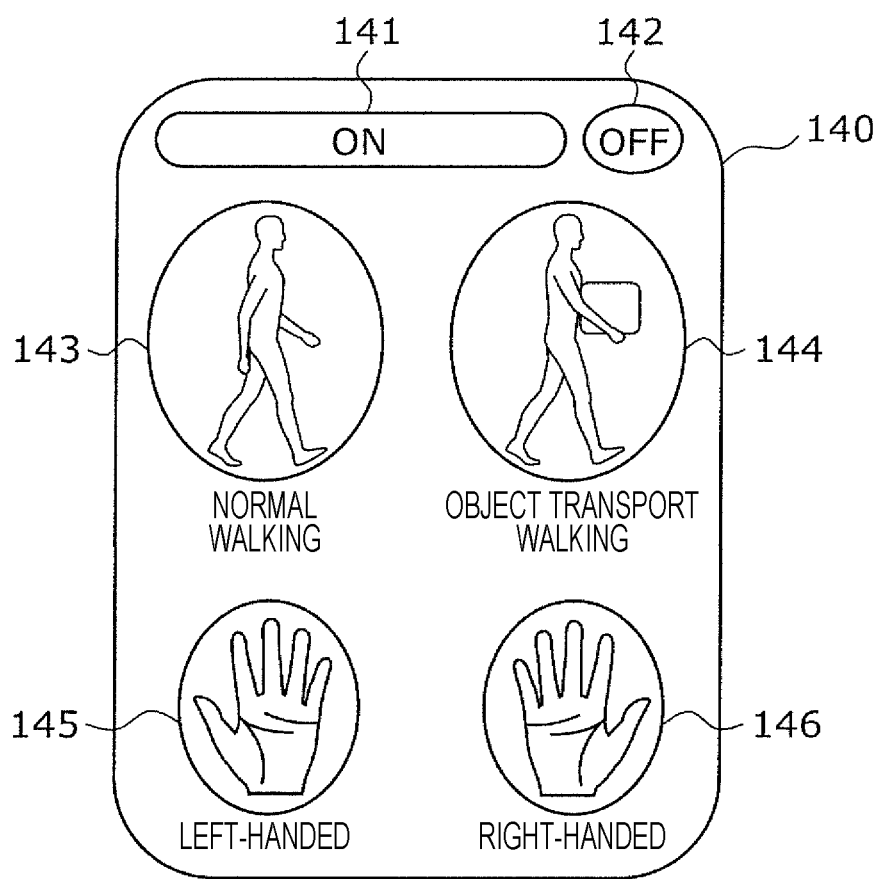
FIG. 8 is a diagram illustrating an example of an input section of an input device included in the assistance apparatus according to the embodiment.

For example, FIG. 8 illustrates an example input section of the input device 140 included in the assistance apparatus 100 according to the embodiment. The input device 140 includes six physical buttons that accept input. The six buttons include an "ON" button 141 for starting the assistance apparatus 100, an "OFF" button 142 for stopping the operation of the assistance apparatus 100, a normal walking button 143 for selecting a normal walking mode, an object transport walking button 144 for selecting an object transport walking mode, a "left-handed" button 145 for inputting the "left hand" as the dominant hand of the user, and a "right-handed" button 146 for inputting the "right hand" as the dominant hand of the user. The normal walking mode is one of the operation modes of the assistance apparatus 100. The object transport walking mode is one of the operation modes of the assistance apparatus 100. When the input section of the input device 140 is a touch panel, each button may be implemented as an icon on a screen. The "left-handed" button 145 and the "right-handed" button 146 may be each a dial, a slide button, a lever such as a joystick, or any other suitable device. In this embodiment, the input device 140 is disposed on the upper-body belt 111, as a non-limiting example. Alternatively, the input device 140 may be disposed on the knee belt 112a or 112b or attached to a part of the body of the user 1, which is away from the upper-body belt 111. The terminal device 150, which is external to the assistance apparatus 100, may have a button configuration similar to that of the input device 140 or an icon configuration on a screen.

Figure 9:
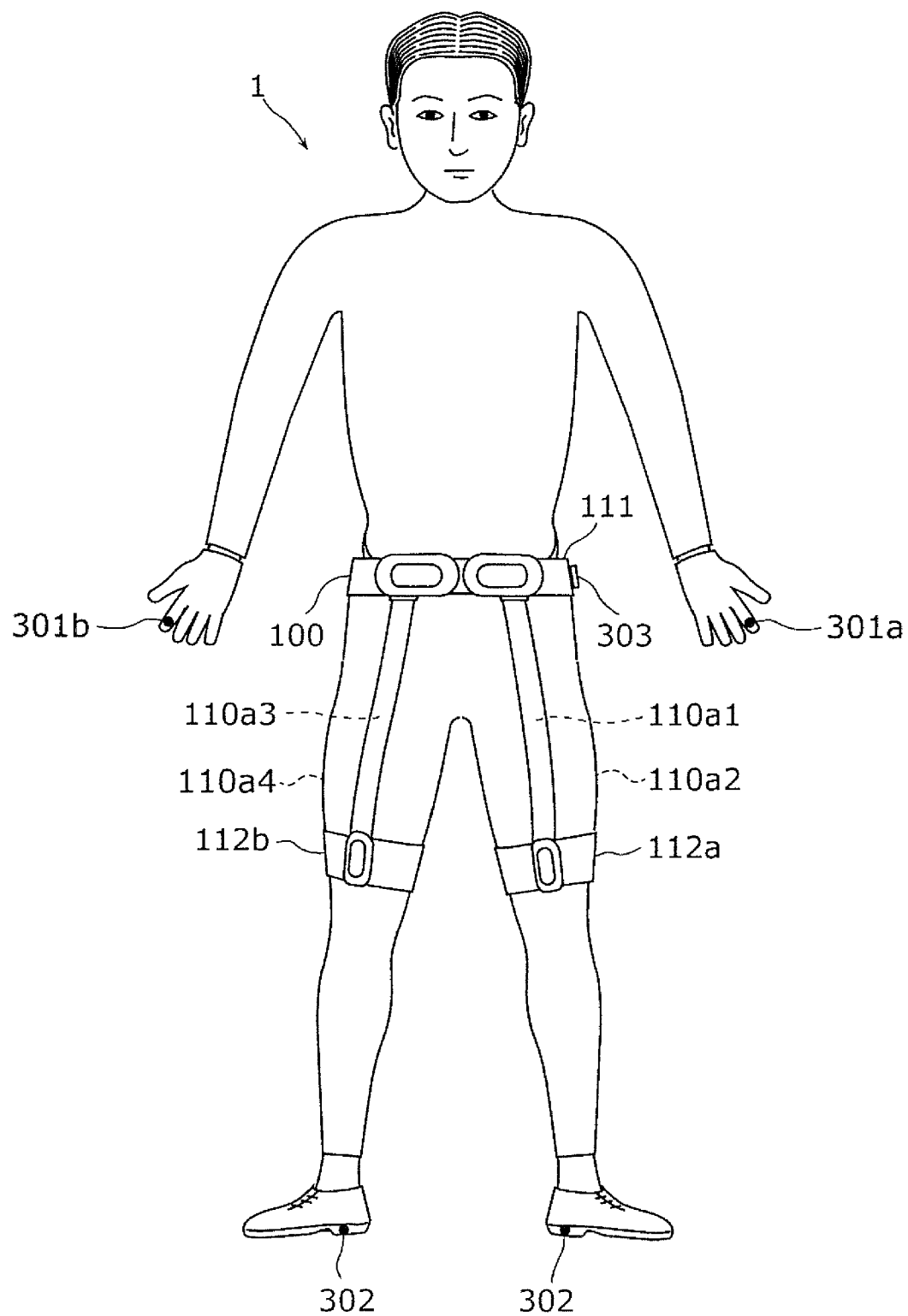
FIG. 9 is a diagram illustrating the arrangement of sensors and so on that are attached to the body of the user.

In this embodiment, furthermore, as illustrated in FIG. 9, contact sensors 301a and 301b and at least one of a pressure-sensitive sensor 302 and an inertial measurement unit 303 are attached to the body of the user 1. FIG. 9 is a diagram illustrating the arrangement of sensors and so on to be attached to the body of the user 1. The contact sensors 301a and 301b, the pressure-sensitive sensor 302, and the inertial measurement unit 303 output detection results to the control unit 120. The contact sensor 301a is attached to the left hand of the user 1, and the contact sensor 301b is attached to the right hand of the user 1. Specifically, the contact sensor 301a is attached to a finger tip or the like of a left glove to be worn by the user 1, and the contact sensor 301b is attached to a finger tip or the like of a right glove to be worn by the user 1. In this embodiment, as a non-limiting example, the contact sensor 301a is attached to the forefinger of the left hand, which frequently comes into contact with an object when the user 1 is carrying the object, and the contact sensor 301b is attached to the forefinger of the right hand, which frequently comes into contact with an object when the user 1 is carrying the object. The contact sensor 301a and the contact sensor 301b may be each attached to any other finger, a palm, or the like. The contact sensors 301a and 301b detect a direct contact and an indirect contact between the hands of the user 1 and an object. Examples of the contact sensors 301a and 301b include a contact detection sensor, a touch sensor, a proximity sensor, and a sensor similar to the pressure-sensitive sensor 302. The contact sensors 301a and 301b may be attached to the arms of the user 1 or the like, which may come into contact with an object when the user 1 is carrying the object. The contact sensor 301a is a left contact sensor attachable to the left hand and is an example of a left pressure sensor. The contact sensor 301b is a right contact sensor attachable to the right hand and is an example of a right pressure sensor.

The left pressure sensor may be a left load sensor or a left force sensor. The right pressure sensor may be a right load sensor or a right force sensor. The left pressure value may be a left pressure value obtained from the left pressure sensor, a left load value obtained from the left load sensor, or a left force value obtained from the left force sensor. The right pressure value may be a right pressure value obtained from the right pressure sensor, a right load value obtained from the right load sensor, or a right force value obtained from the right force sensor.

The pressure-sensitive sensor 302 is attached to each of the soles of the feet of the user 1. Specifically, the pressure-sensitive sensor 302 is attached to each of the bottoms or the like of shoes worn by the user 1. The pressure-sensitive sensor 302 may be attached to each of both feet of the user 1 or to either foot of the user 1. The pressure-sensitive sensor 302 detects a pressure acting on each of the soles of the feet of the user 1, that is, a load. Examples of the pressure-sensitive sensor 302 include a capacitive pressure sensor, a piezoelectric pressure sensor, and a strain gauge pressure sensor. The inertial measurement unit 303 is attached to a portion of the body of the user 1 that moves along with the movement of the user 1, such as the waist in the upper half of the body of the user 1. Specifically, the inertial measurement unit 303 is attached to the upper-body belt 111. The inertial measurement unit 303 includes an acceleration sensor and a gyro sensor (also referred to as an "angular velocity sensor"). Examples of the acceleration sensor include a three-axis acceleration sensor, and examples of the gyro sensor include a three-axis gyro sensor. The inertial measurement unit 303 may include an acceleration sensor, but may include no gyro sensor. The inertial measurement unit 303 may further include a geomagnetic sensor. The inertial measurement unit 303 detects, on the basis of a detected acceleration and angular velocity, the acceleration of the user 1 in each direction, and the movement direction, movement speed, and movement distance of the user 1. The pressure-sensitive sensor 302 and the inertial measurement unit 303 are examples of a gait sensor.

The contact sensors 301a and 301b, the pressure-sensitive sensor 302, and the inertial measurement unit 303 exchange information with the control unit 120 via wired communication or wireless communication. The wired communication may be any of the wired communication described above, and the wireless communication may be any of the wireless communication described above.

As illustrated in FIG. 3, the control unit 120 includes a grasp recognition unit 121, a drive control unit 122, a gait timing detection unit 123, a wire tension recognition unit 124, and a storage unit 125. The grasp recognition unit 121, the drive control unit 122, the gait timing detection unit 123, and the wire tension recognition unit 124, which are constituent elements of the control unit 120, may be implemented by a computer system including a processor such as a central processing unit (CPU) or a digital signal processor (DSP) and a memory such as a random access memory (RAM) and a read-only memory (ROM). Some or all of the functions of the constituent elements described above may be achieved by the CPU or the DSP executing a program recorded on the ROM by using the RAM as a work memory. Alternatively, some or all of the functions of the constituent elements described above may be achieved by a dedicated hardware circuit such as an electronic circuit or an integrated circuit. The functions of some or all of the constituent elements described above may be implemented by a combination of the software functions described above and a hardware circuit. The program may be provided as an application by communication via a communication network such as the Internet, communication conforming to a mobile communication standard, communication via any other wireless or wired network, broadcasting, or the like. A computer system and/or a hardware circuit constituted by the control unit 120 may be mounted on the upper-body belt 111, accommodated in the containers 111a1 to 111a4 together with the motors 114a1 to 114a4, or embedded in the upper-body belt 111 at a different location from the motors 114a1 to 114a4, for example. The control unit 120 is an example of a control circuit.

The storage unit 125 is capable of storing information, and the stored information is retrievable from the storage unit 125. The storage unit 125 stores computer programs in accordance with which the constituent elements of the control unit 120 execute processes, threshold values described below, input profiles of wire tensions described below, and so on. The storage unit 125 is implemented as a storage device, for example, a semiconductor memory such as a ROM, a RAM, or a flash memory, a hard disk drive, or a solid state drive (SSD). In this embodiment, the storage unit 125 is included in the control unit 120. Alternatively, the storage unit 125 may be disposed separately from the control unit 120. The storage unit 125 is an example of a memory.

Figure 10A:
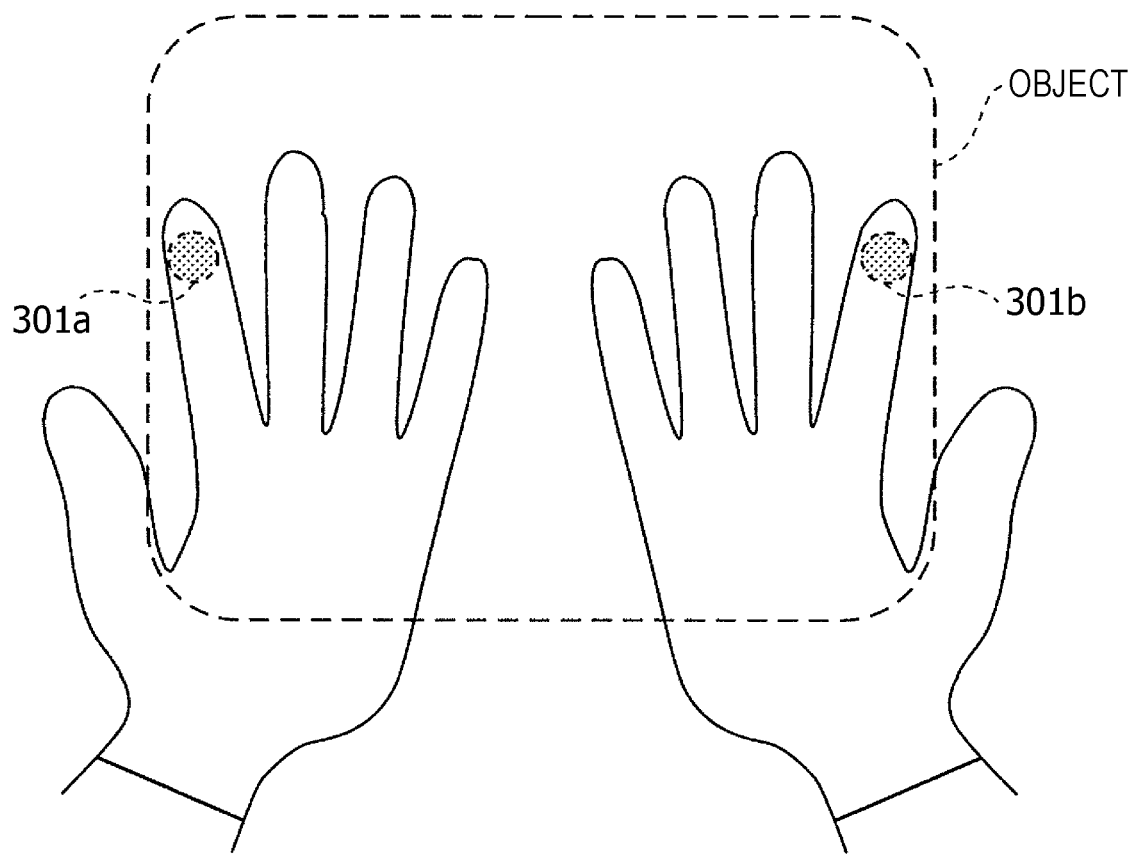
FIG. 10A is a diagram illustrating a relationship between contact sensors and the hands of the user.

The grasp recognition unit 121 detects a load applied to the hand of the user 1 and detects a grasp of an object by the user 1 accordingly. The grasp recognition unit 121 detects loads applied to the left and right hands of the user 1 on the basis of amounts of changes in the sensor values acquired from the contact sensors 301a and 301b, respectively. The loads detected from the sensor values of the contact sensors 301a and 301b are examples of a pressure value. For example, as illustrated in FIG. 10A, the left contact sensor 301a is placed on the left hand of the user 1, and the right contact sensor 301b is placed on the right hand of the user 1. Specifically, the left contact sensor 301a is attached to the tip of the forefinger of the left hand, and the right contact sensor 301b is attached to the tip of the forefinger of the right hand. FIG. 10A is a diagram illustrating a relationship between the contact sensors 301a and 301b and the hands of the user.

Figure 10B:
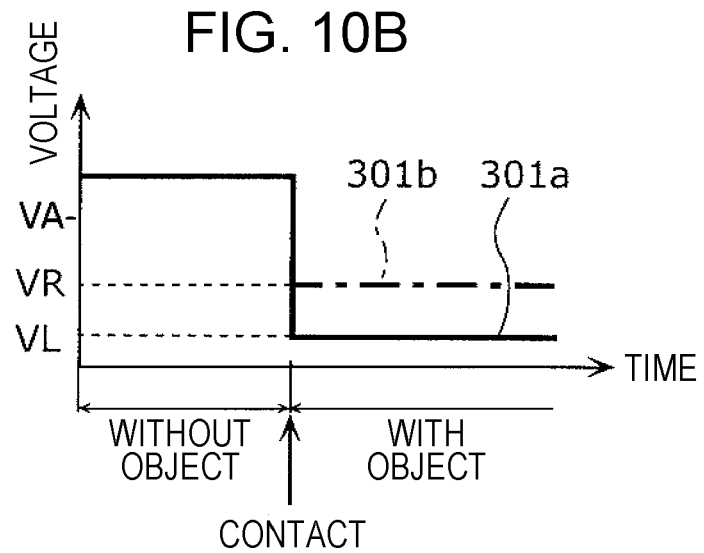
FIG. 10B is a diagram illustrating an example of a signal of a contact sensor.

When the contact sensors 301a and 301b are piezoelectric sensors, the grasp recognition unit 121 detects a time point at which each of voltage values corresponding to sensor values detected by the contact sensors 301a and 301b becomes less than a predetermined value, as a time point at which the corresponding one of the left and right hands of the user 1 touches an object, that is, a time point at which the corresponding one of the left and right hands of the user 1 grasps the object. As each of the voltage values of the contact sensors 301a and 301b decreases, the load applied by the object to the corresponding one of the left and right hands of the user 1 increases. Accordingly, the grasp recognition unit 121 calculates the loads applied to the left and right hands of the user 1 from the voltage values of the contact sensors 301a and 301b, respectively. For example, in example signals of the contact sensors 301a and 301b illustrated in FIG. 10B, the predetermined value is represented by "VA". In FIG. 10B, when the voltage values of the contact sensors 301a and 301b remain less than the predetermined value VA, that is, when the user 1 is carrying an object, a voltage value VL of the left contact sensor 301a is smaller than a voltage value VR of the right contact sensor 301b. Thus, a load LL applied to the left hand of the user 1 is larger than a load LR applied to the right hand. The grasp recognition unit 121 calculates the load LL applied to the left hand of the user 1 and the load LR applied to the right hand of the user 1 from the voltage values VL and VR of the contact sensors 301a and 301b, respectively, and outputs the loads LL and LR to the drive control unit 122. In the example illustrated in FIG. 10B, VL<VR and LL>LR hold.

The gait timing detection unit 123 detects a gait timing to determine a timing of assisting the user 1. The gait timing may include a timing of starting assisting the user 1 during walking, and a timing of determining phases such as a stance phase and a swing phase in a period during which the user 1 takes one step. The drive control unit 122 determines a timing of assisting the user 1 from the gait timing detected by the gait timing detection unit 123 and controls the operation of the motors 114.

Specifically, the gait timing detection unit 123 estimates a gait cycle of the user 1 wearing the assistance apparatus 100, predicts gait phases in the next one step on the basis of the estimation result, and outputs assistance timings based on the predicted gait phases to the drive control unit 122. A gait cycle is a time interval from heel strike of one leg to the next heel strike of the same leg. The gait cycle is constituted by a period of a stance phase and a period of a swing phase. The gait cycle may be sequence of motions occurring from heel strike of one leg to the next heel strike of the same leg.

The gait timing detection unit 123 detects a timing of heel strike of the user 1 on the basis of a sensor value acquired from the pressure-sensitive sensor 302 or on the basis of sensor values acquired from the acceleration sensor and the gyro sensor of the inertial measurement unit 303, and estimates a gait phase for each step, or a gait cycle, of the user 1 in real time. The gait cycles and the steps may be in a one-to-one relationship. Each step of the user 1 is a step with either of the left and right legs. For example, each step of the user 1 corresponds to a period from when the left leg touches the ground to when the left leg touches the ground again. The gait timing detection unit 123 predicts, based on the estimated gait cycle, a gait phase for the next step and a starting time and duration of each of the stance phase and swing phase for the next step, and outputs the prediction results to the drive control unit 122. When the terminal device 150 carried by the user 1 includes an inertial measurement unit, the gait timing detection unit 123 may acquire a sensor value of an acceleration sensor and a sensor value of a gyro sensor from the terminal device 150.

Gait phases represent temporal timings of gait states during a single step taken by the user 1. A time point at which one leg of the user 1 touches the ground corresponds to a time point at which a gait phase is 0%, and a time point at which the same leg of the user 1 touches the ground again corresponds to a time point at which a gait phase is 100%. In a gait phase, timings of gait states of the user 1 are represented in the range of 0% to 100%. For example, a value of 0% to 100% of a gait phase may correspond to the time elapsed from when one leg of the user 1 touches the ground to when the same leg of the user 1 touches the ground again. Specifically, when the time period from when one leg of the user 1 touches the ground to when the same leg of the user 1 touches the ground again is 1 second, the gait phase at the point in time at which a period of 0.5 seconds elapses from the time when the leg of the user 1 touches the ground is represented by 50%.

Figure 11:
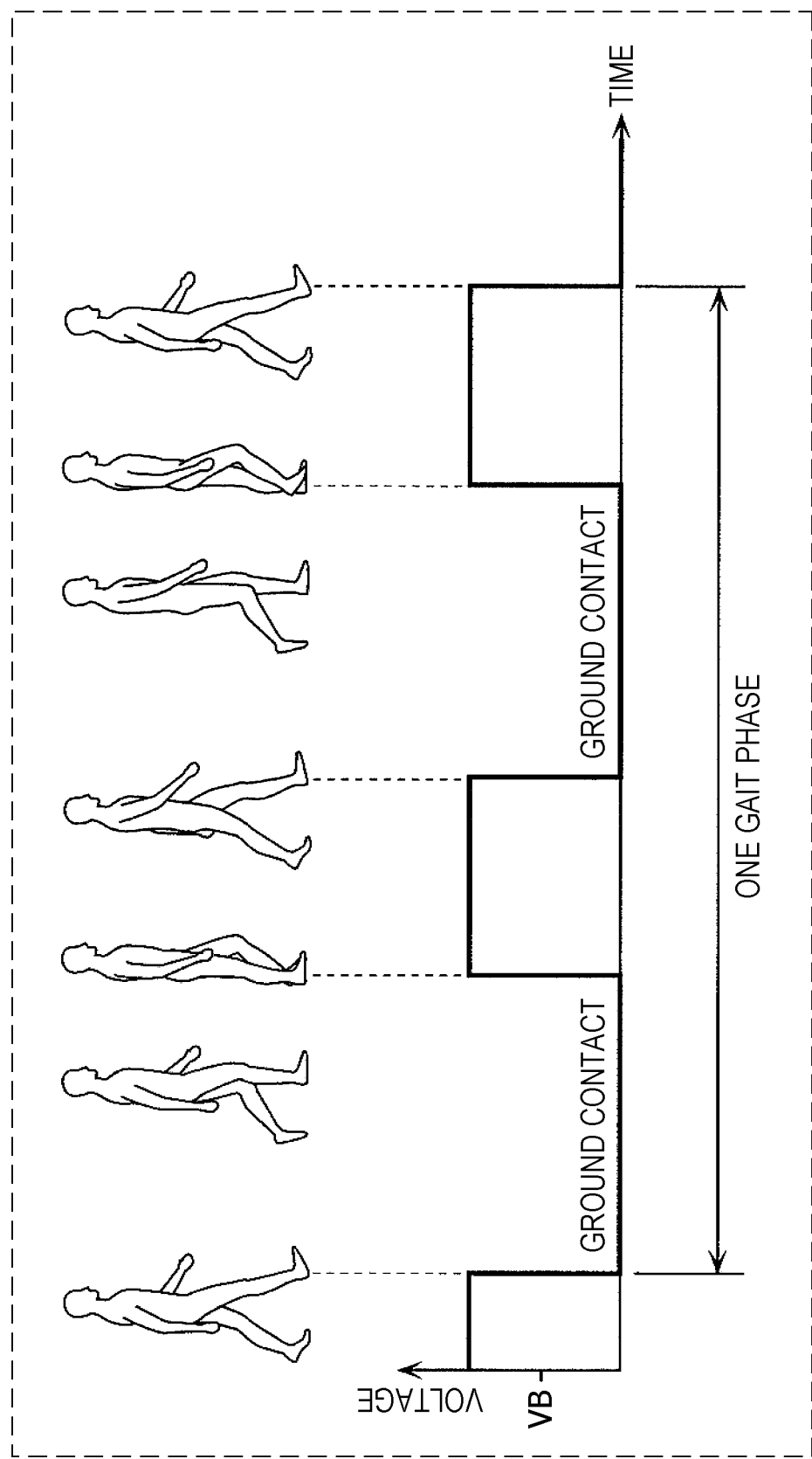
FIG. 11 is a diagram illustrating an example of a signal of a pressure-sensitive sensor.

More specifically, the gait timing detection unit 123 determines a time point at which the leg of the user 1 touches the ground on the basis of the sensor value of the pressure-sensitive sensor 302 in such a manner that, for example, as illustrated in FIG. 11, a time point at which the voltage value corresponding to the pressure sensor value of the pressure-sensitive sensor 302 becomes less than a predetermined value is detected as a timing of heel strike. FIG. 11 illustrates an example of a signal based on signals of the pressure-sensitive sensors 302. For example, the predetermined value is represented by "VB" in FIG. 11. A period during which the pressure-sensitive sensor 302 measures a pressure value greater than or equal to the predetermined value corresponds to a period of heel contact. The pressure-sensitive sensor 302 is placed at each of the feet of the user 1. The gait timing detection unit 123 acquires a timing at which the shoe touches the ground using the pressure-sensitive sensor 302, rather than a timing that is based on the inertial measurement unit 303 located in the upper-body belt 111 or the like. Thus, the gait timing detection unit 123 can more reliably estimate a gait cycle.

Figure 12:
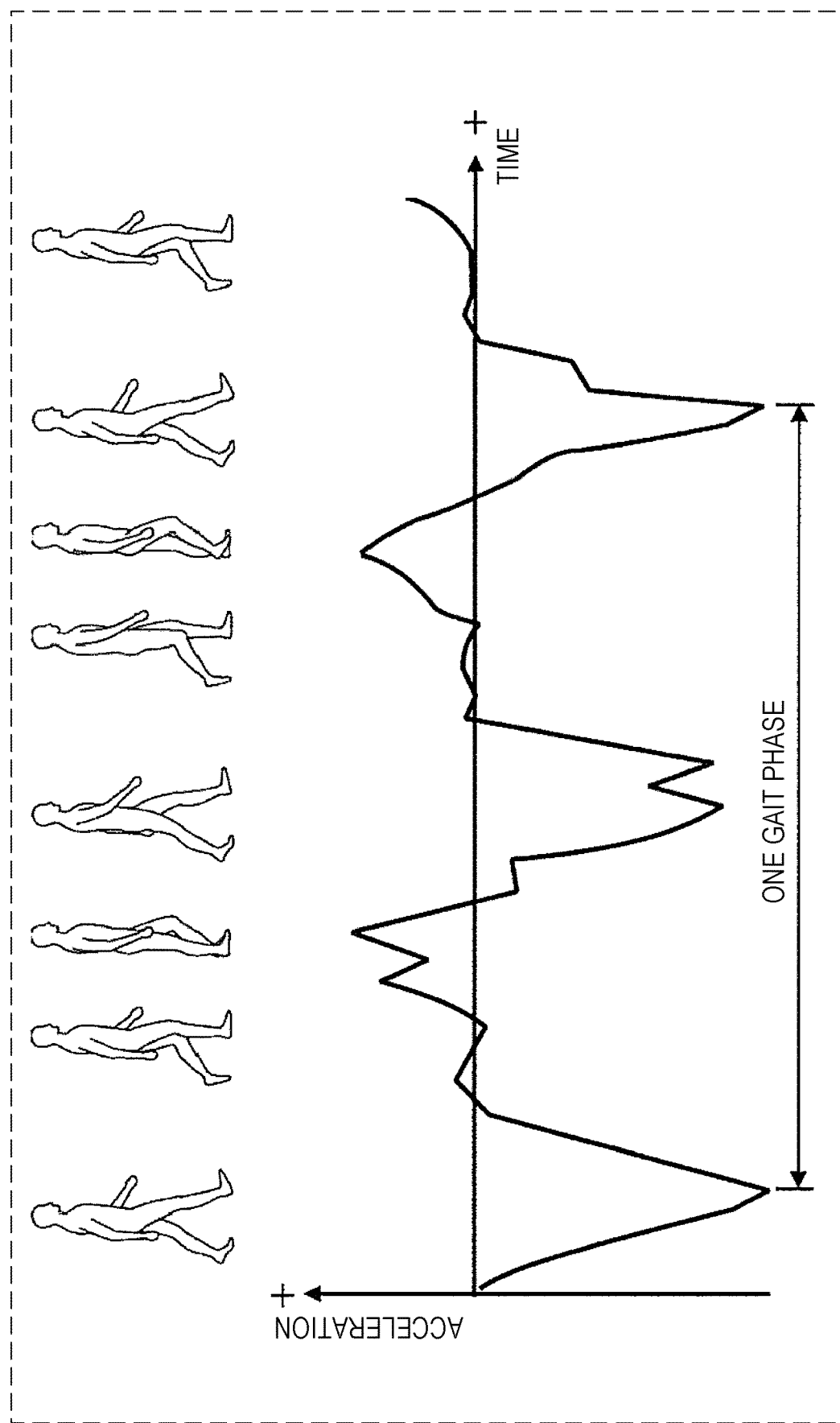
FIG. 12 is a diagram illustrating an example of a signal of an acceleration sensor of an inertial measurement unit.

When the inertial measurement unit 303 is used, the gait timing detection unit 123 determines a time point at which the foot of the user 1 touches the ground on the basis of information obtained by the acceleration sensor. For a method for estimating a time point at which a foot touches the ground by using an acceleration sensor, see, for example, IEEE TRANSACTIONS ON BIOMEDICAL ENGINEERING, VOL. 52, NO. 3, 2005, p. 488, FIG. 1, p. 489, FIG. 2. When estimating a gait cycle on the basis of a sensor value of the inertial measurement unit 303, the gait timing detection unit 123 may estimate a gait cycle by using signal waveforms obtained from the acceleration sensor and the gyro sensor. For example, a gait cycle can be estimated by using a signal waveform obtained from the acceleration sensor, as illustrated in FIG. 12. In the example illustrated in FIG. 12, the signal waveform obtained from the acceleration sensor can be used to estimate a time point at which the foot of the user 1 touches the ground, and a gait cycle can be estimated accordingly. FIG. 12 illustrates an example of a signal of the acceleration sensor of the inertial measurement unit 303.

The user 1 may wear an angle sensor (also referred to as a "tilt sensor"). In this case, the angle sensor is attached to, for example, a thigh of the user 1. The gait timing detection unit 123 acquires the angle of the hip joint of the user 1 as gait information. The gait timing detection unit 123 calculates a gait phase on the basis of a cycle of change in the angle of the hip joint of the user 1.

Regardless of which of the pressure-sensitive sensor 302 and the inertial measurement unit 303 is used, for example, the gait timing detection unit 123 may estimate, based on a sensor value of the pressure-sensitive sensor 302 or a sensor value of the inertial measurement unit 303 for the latest three steps of the user 1, an elapsed time of 0% to 100% of a gait phase for each step and may calculate an average value of the three elapsed times. Then, the gait timing detection unit 123 may predict the point in time corresponding to 100% of the gait phase for the next step on the basis of the average value of the elapsed times. Further, the gait timing detection unit 123 may estimate the start timings of the stance phase and the swing phase during the gait phase for each step on the basis of the signal waveform of the sensor and calculate an average value of the start timings for the three steps. Then, the gait timing detection unit 123 may predict, based on the average value, the start timings of the stance phase and the swing phase for the next one step.

Alternatively, the gait timing detection unit 123 may estimate, based on a sensor value of the pressure-sensitive sensor 302 or a sensor value of the inertial measurement unit 303 for the last one step of the user 1, an elapsed time of 0% to 100% of the gait phase for the one step and may predict the point in time corresponding to 100% of the gait phase for the next step on the basis of the estimated elapsed time. Further, the gait timing detection unit 123 may estimate the start timings of the stance phase and the swing phase during the one step on the basis of the sensor values for the last one step of the user 1, and may predict the start timings of the stance phase and the swing phase for the next one step.

The wire tension recognition unit 124 detects the tensions generated in the wires 110a1 to 110a4. The wire tension recognition unit 124 detects the tensions of the wires 110a1 to 110a4 on the basis of sensor values acquired from the force sensors 115a1 to 115a4. The wire tension recognition unit 124 outputs the detected tensions of the wires 110a1 to 110a4 to the drive control unit 122.

The drive control unit 122 controls the motors 114a1 to 114a4, which respectively adjust the tensions of the wires 110a1 to 110a4, on the basis of information on a predicted gait phase of the user 1, which is acquired from the gait timing detection unit 123, and on the basis of information indicating whether the user 1 is carrying an object, which is acquired from the grasp recognition unit 121. The drive control unit 122 starts the motors 114a1 to 114a4, stops the operation of the motors 114a1 to 114a4, and controls the amount by which the wires 110a1 to 110a4 are respectively pulled by the motors 114a1 to 114a4 and the pulling tensions of the wires 110a1 to 110a4. The drive control unit 122 controls the amount of rotation of each of the motors 114a1 to 114a4 and adjusts the rotation torque of each of the motors 114a1 to 114a4, thereby enabling control of the amount by which the corresponding wire among the wires 110 is pulled and the pulling tensions of the corresponding wire.

Specifically, the drive control unit 122 determines a type of assistance to be provided to the user 1 on the basis of the prediction result of the gait timing acquired from the gait timing detection unit 123. Examples of the type of assistance include motions of the leg on which assistance is to be provided to the user 1, such as flexion and extension. In accordance with the type of assistance, the drive control unit 122 further determines a wire to be pulled to assist a motion of the user 1 among the wires 110a1 to 110a4, a tension to be applied to the wire, and a timing of pulling the wire.

Further, the drive control unit 122 changes the relationship between the tension of a wire and the timing of pulling the wire even for the same type of assistance on the basis of information acquired from the grasp recognition unit 121 indicating whether the user 1 is carrying an object, the loads applied to the left and right hands of the user 1, and so on.

An assistance correspondence, which is a relationship between the gait timing acquired from the gait timing detection unit 123 and the type of assistance, is set in advance and is stored in, for example, the storage unit 125. A wire-tension relationship, which is a relationship between a wire to be pulled, a tension of the wire, and a timing of pulling the wire, is set in advance in accordance with the type of assistance, information indicating whether the user 1 is carrying an object, and so on, and is stored in, for example, the storage unit 125. The wire-tension relationship may be updated on the basis of the achievement of assistance-based control by the assistance apparatus 100. On the basis of information on the assistance correspondence and the wire-tension relationship, which are stored in the storage unit 125, the drive control unit 122 determines a type of assistance to be provided to the user 1 and determines control of wires corresponding to the determined type of assistance. The drive control unit 122 controls the motors linked to the determined wires, in accordance with tensions to be applied to the wires and timings of puling the wires.

Further, the drive control unit 122 controls the operation of the motors 114a1 to 114a4 on the basis of information on the tensions of the wires 110a1 to 110a4, which is acquired from the wire tension recognition unit 124, so that the tensions of the wires 110a1 to 110a4 have predetermined levels. In addition, the drive control unit 122 may change the wire-tension relationship on the basis of, in addition to the information acquired from the grasp recognition unit 121, the gait timing detection unit 123, and the wire tension recognition unit 124, information on the user 1, such as age, gender, body size, and physical activity level, the degree of assistance on the leg, and so on, and may use the changed wire-tension relationship.

2. Modification of Assistance Apparatus

Figure 13:
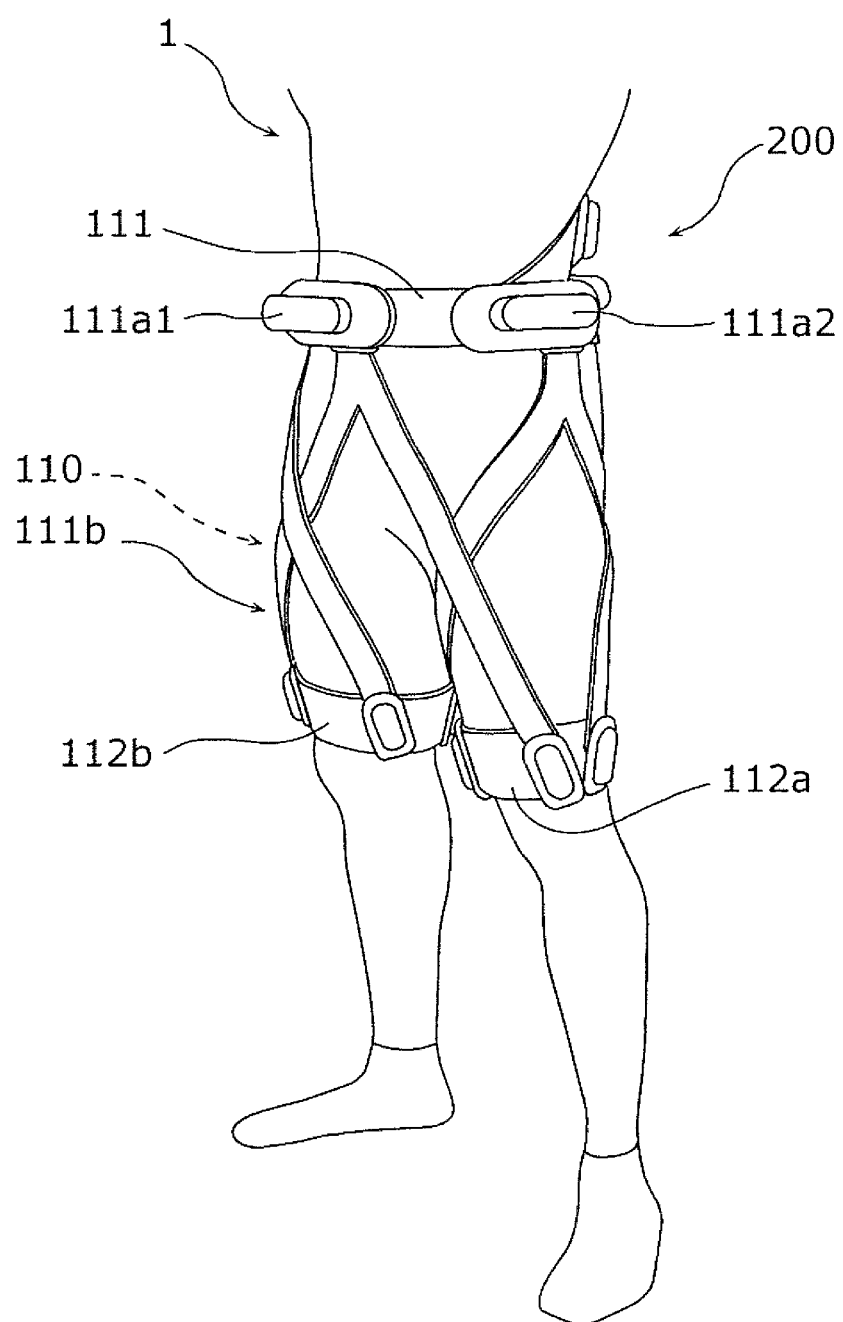
FIG. 13 is a perspective view of a user wearing an assistance apparatus according to a modification of the embodiment, as viewed obliquely from the front.
Figure 14:
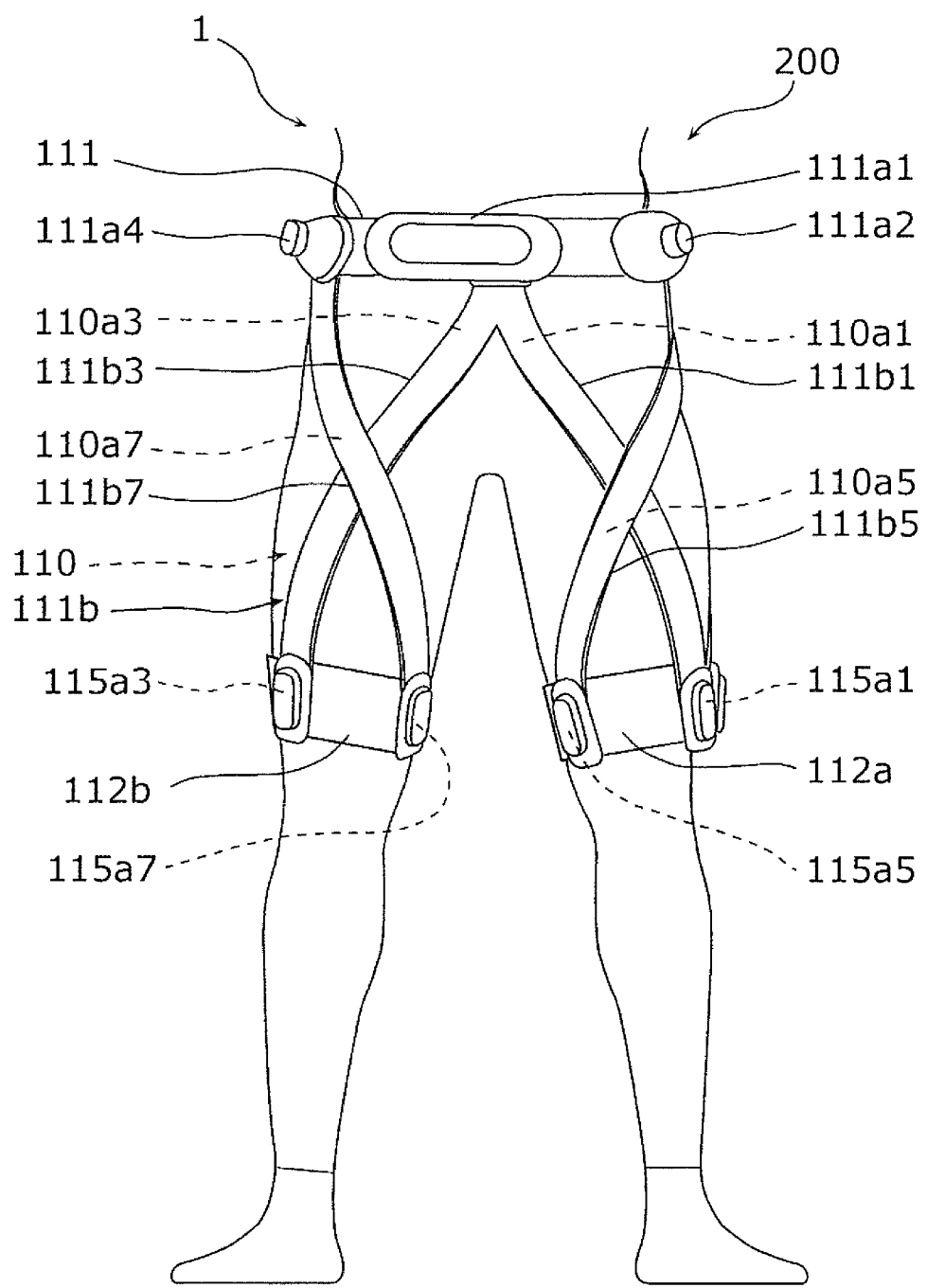
FIG. 14 is a front view of the user wearing the assistance apparatus illustrated in FIG. 13.
Figure 15:
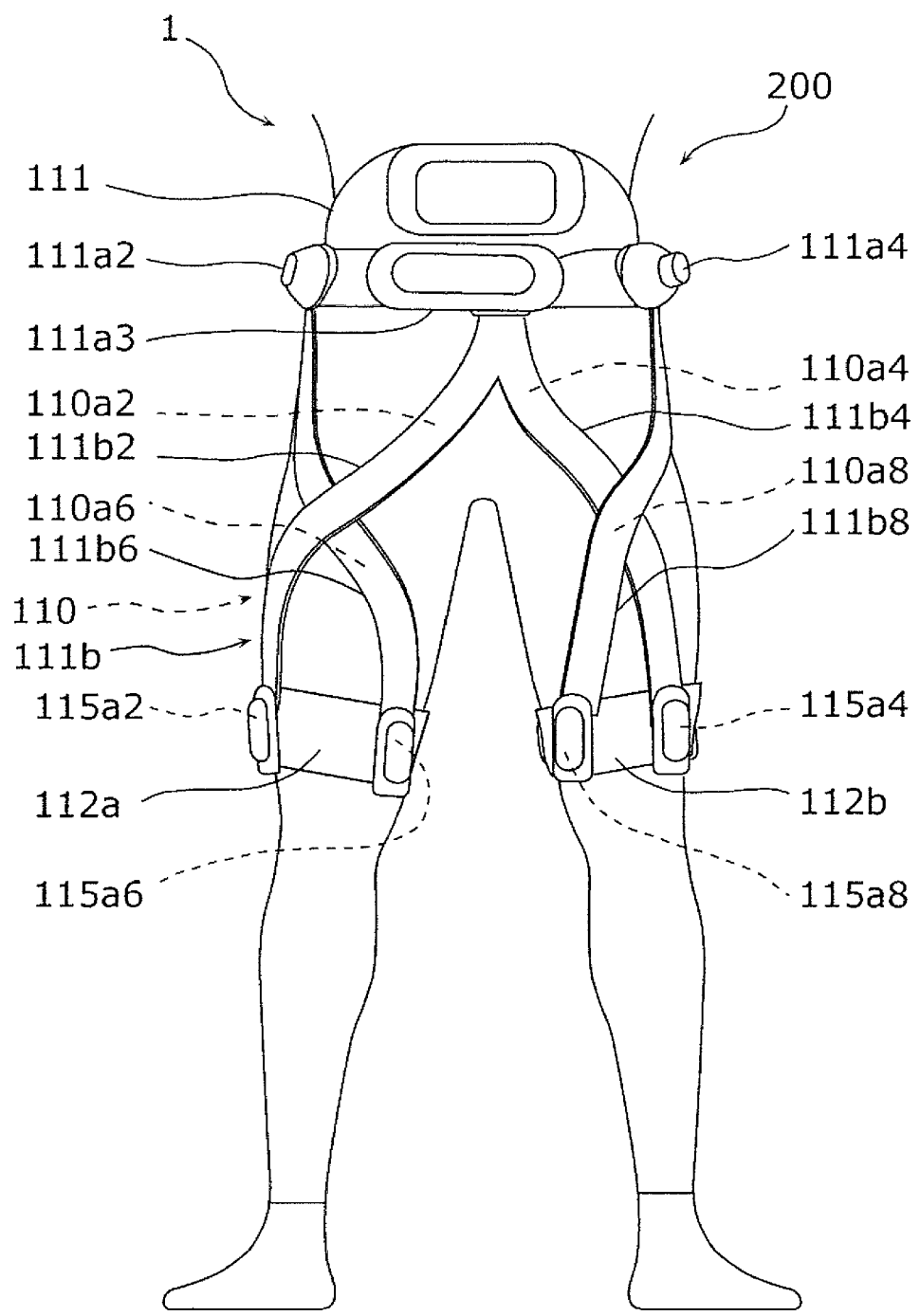
FIG. 15 is a back view of the user wearing the assistance apparatus illustrated in FIG. 13.
Figure 16:
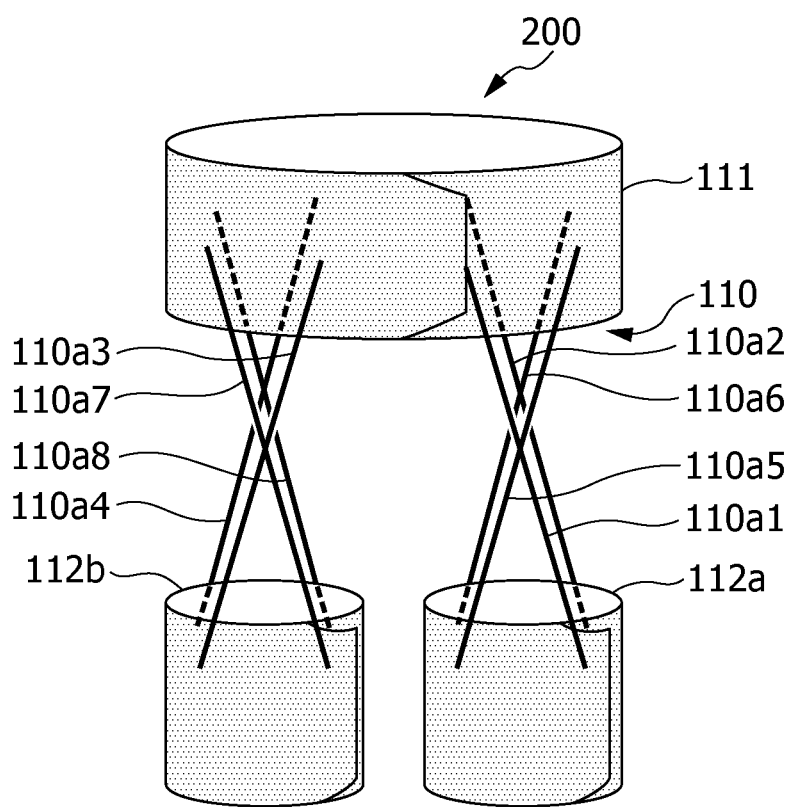
FIG. 16 is a diagram schematically illustrating the arrangement of constituent elements of the assistance apparatus illustrated in FIG. 13.
Figure 17:
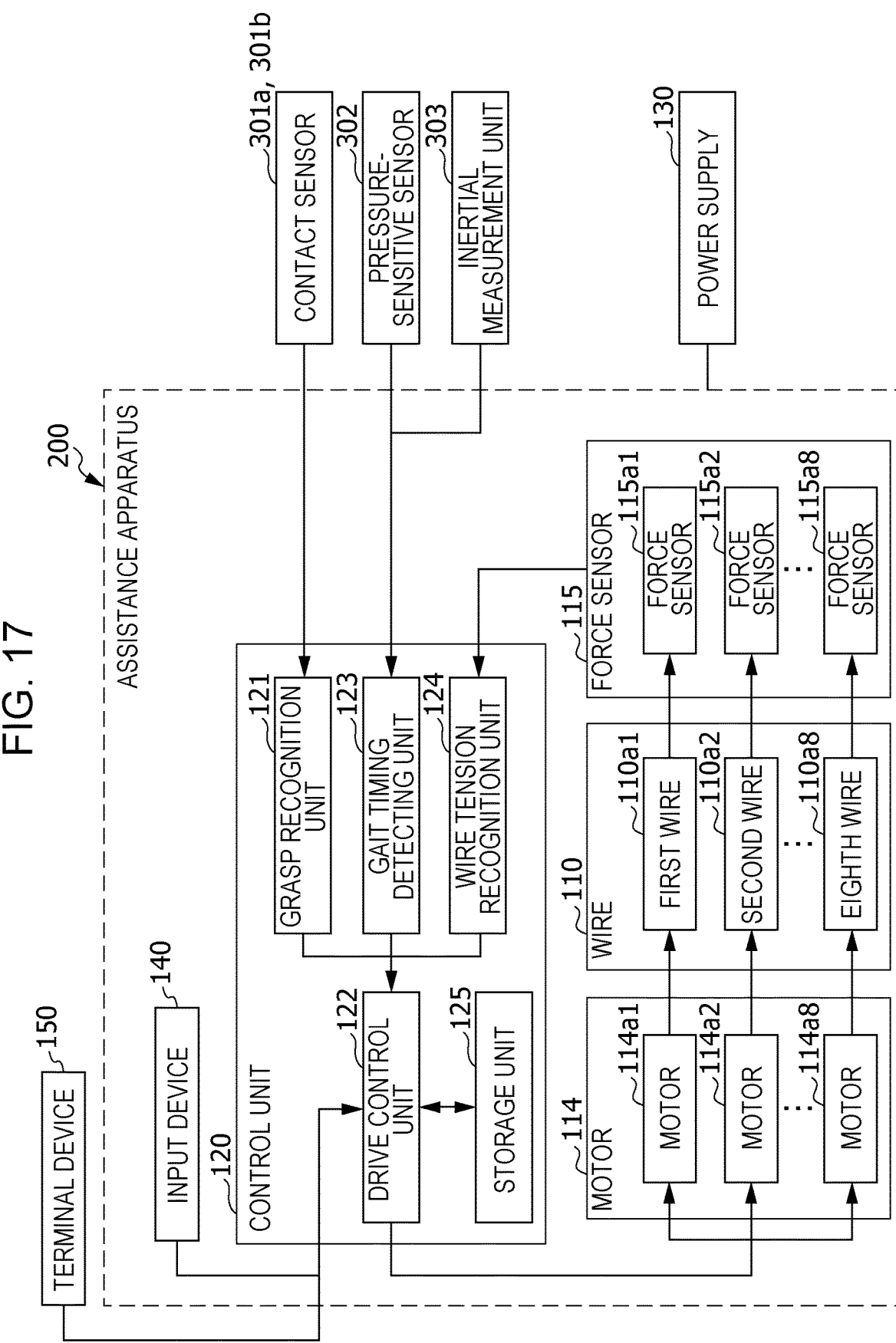
FIG. 17 is a block diagram illustrating a functional configuration of the assistance apparatus illustrated in FIG. 13.

In the assistance apparatus 100 described above, the upper-body belt 111 is coupled to the knee belts 112a and 112b by using the four wires 110a1 to 110a4. However, the number of wires is not limited to that in the embodiment. For example, as illustrated in FIG. 13 to FIG. 17, eight wires may be used. FIG. 13 is a perspective view of a user 1 wearing an assistance apparatus 200 according to a modification of the embodiment, as viewed obliquely from the front. FIG. 14 is a front view of the user 1 wearing the assistance apparatus 200 illustrated in FIG. 13. FIG. 15 is a back view of the user 1 wearing the assistance apparatus 200 illustrated in FIG. 13. FIG. 16 is a diagram schematically illustrating the arrangement of constituent elements of the assistance apparatus 200 illustrated in FIG. 13. FIG. 17 is a block diagram illustrating a functional configuration of the assistance apparatus 200 illustrated in FIG. 13.

As illustrated in FIG. 13 to FIG. 17, the assistance apparatus 200 according to the modification includes an upper-body belt 111, knee belts 112a and 112b, and eight wires, namely, first to eighth wires 110a1 to 110a8. The assistance apparatus 200 further includes a motor 114a1 linked to the first wire 110a1, a motor 114a2 linked to the second wire 110a2, a motor 114a3 linked to the third wire 110a3, a motor 114a4 linked to the fourth wire 110a4, a motor 114a5 linked to the fifth wire 110a5, a motor 114a6 linked to the sixth wire 110a6, a motor 114a7 linked to the seventh wire 110a7, a motor 114a8 linked to the eighth wire 110a8, a force sensor 115a1 disposed on the first wire 110a1, a force sensor 115a2 disposed on the second wire 110a2, a force sensor 115a3 disposed on the third wire 110a3, a force sensor 115a4 disposed on the fourth wire 110a4, a force sensor 115a5 disposed on the fifth wire 110a5, a force sensor 115a6 disposed on the sixth wire 110a6, a force sensor 115a7 disposed on the seventh wire 110a7, a force sensor 115a8 disposed on the eighth wire 110a8, and a control unit 120.

The upper-body belt 111 includes containers 111a1, 111a2, 111a3, and 111a4 so as to correspond to the front part, left side part, back part, and right side part of the body of the user 1, respectively. The motors 114a1 and 114a3 are accommodated in the container 111a1, the motors 114a5 and 114a6 are accommodated in the container 111a2, the motors 114a2 and 114a4 are accommodated in the container 111a3, and the motors 114a7 and 114a8 are accommodated in the container 111a4.

The first wire 110a1 and the fifth wire 110a5 are arranged to extend in directions crossing each other on or above the front part of the body of the user 1, and, more specifically, are arranged to cross each other. Each of the first wire 110a1 and the fifth wire 110a5 has one end fixed to the left knee belt 112a. The first wire 110a1 has another end coupled to the motor 114a1, and the fifth wire 110a5 has another end coupled to the motor 114a5. That is, the first wire 110a1 couples the left knee belt 112a and the motor 114a1 to each other, and the fifth wire 110a5 couples the left knee belt 112a and the motor 114a5 to each other.

The second wire 110a2 and the sixth wire 110a6 are arranged to extend in directions crossing each other on or above the back part of the body of the user 1, and, more specifically, are arranged to cross each other. Each of the second wire 110a2 and the sixth wire 110a6 has one end fixed to the left knee belt 112a. The second wire 110a2 has another end coupled to the motor 114a2, and the sixth wire 110a6 has another end coupled to the motor 114a6. That is, the second wire 110a2 couples the left knee belt 112a and the motor 114a2 to each other, and the sixth wire 110a6 couples the left knee belt 112a and the motor 114a6 to each other.

The third wire 110a3 and the seventh wire 110a7 are arranged to extend in directions crossing each other on or above the front part of the body of the user 1, and, more specifically, are arranged to cross each other. Each of the third wire 110a3 and the seventh wire 110a7 has one end fixed to the right knee belt 112b. The third wire 110a3 has another end coupled to the motor 114a3, and the seventh wire 110a7 has another end coupled to the motor 114a7. That is, the third wire 110a3 couples the right knee belt 112b and the motor 114a3 to each other, and the seventh wire 110a7 couples the right knee belt 112b and the motor 114a7 to each other.

The fourth wire 110a4 and the eighth wire 110a8 are arranged to extend in directions crossing each other on or above the back part of the body of the user 1, and, more specifically, are arranged to cross each other. Each of the fourth wire 110a4 and the eighth wire 110a8 has one end fixed to the right knee belt 112b. The fourth wire 110a4 has another end coupled to the motor 114a4, and the eighth wire 110a8 has another end coupled to the motor 114a8. That is, the fourth wire 110a4 couples the right knee belt 112b and the motor 114a4 to each other, and the eighth wire 110a8 couples the right knee belt 112b and the motor 114a8 to each other.

Further, the first wire 110a1 and the second wire 110a2 extend upward and toward the right side of the body of the user 1 from the left knee belt 112a. Specifically, the first wire 110a1 and the second wire 110a2 extend to the right side of the body of the user 1 while extending upward from the left knee belt 112a, and, for example, extend upward and diagonally to the right from the left knee belt 112a. The fifth wire 110a5 and the sixth wire 110a6 extend upward and toward the left side of the body of the user 1 from the left knee belt 112a. Specifically, the fifth wire 110a5 and the sixth wire 110a6 extend to the left side of the body of the user 1 while extending upward from the left knee belt 112a, and, for example, extend upward and diagonally to the left from the left knee belt 112a. The third wire 110a3 and the fourth wire 110a4 extend upward and toward the left side of the body of the user 1 from the right knee belt 112b. Specifically, the third wire 110a3 and the fourth wire 110a4 extend to the left side of the body of the user 1 while extending upward from the right knee belt 112b, and, for example, extend upward and diagonally to the left from the right knee belt 112b. The seventh wire 110a7 and the eighth wire 110a8 extend upward and toward the right side of the body of the user 1 from the right knee belt 112b. Specifically, the seventh wire 110a7 and the eighth wire 110a8 extend to the right side of the body of the user 1 while extending upward from the right knee belt 112b, and, for example, extend upward and diagonally to the right from the right knee belt 112b.

Figure 18:
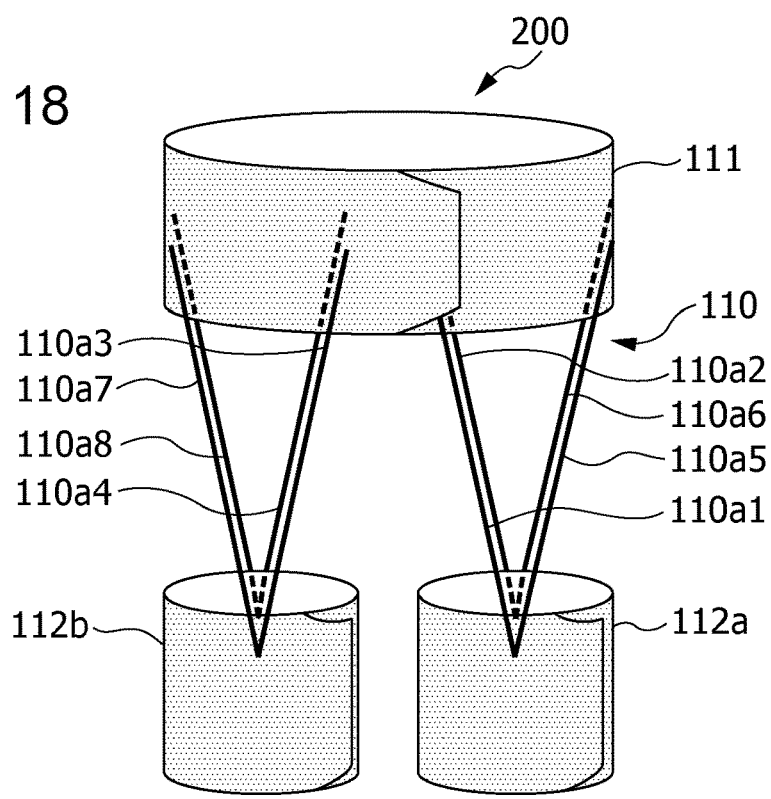
FIG. 18 is a diagram illustrating a modification of the arrangement of wires in the assistance apparatus illustrated in FIG. 13.
Figure 19:
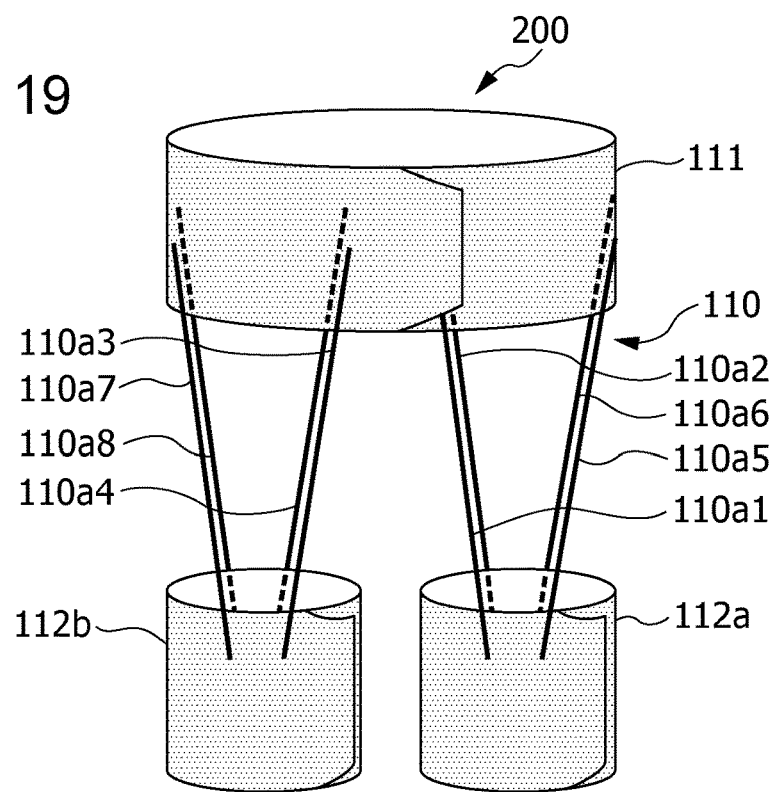
FIG. 19 is a diagram illustrating a modification of the arrangement of wires in the assistance apparatus illustrated in FIG. 13.

Extending of two wires in directions crossing each other is equivalent to crossing of directions in which the two wires extend. Further, crossing of directions in which the two wires extend is equivalent to extending of the two wires in directions that are not parallel to each other. The directions may cross each other at an intersection, or may have no intersection therebetween and may not cross each other. Thus, the two wires may actually cross each other at an intersection or may not actually cross each other. Such two wires extending in directions crossing each other may or may not cross each other when the user 1 is viewed from outside the user 1. When the two wires do not cross each other, as illustrated in FIG. 18 and FIG. 19, the two wires may extend to form a V shape, for example, or may extend away from each other. FIG. 18 and FIG. 19 illustrate modifications of the arrangement of the wires 110 in the assistance apparatus 200 illustrated in FIG. 13.

In this modification, furthermore, eight coupling belts 111b1 to 111b8 are arranged along the first wire 110a1 to the eighth wire 110a8, respectively, and each of the eight coupling belts 111b1 to 111b8 extends from the upper-body belt 111 to the left knee belt 112a or the right knee belt 112b. The coupling belts 111b1 to 111b8 and the first wire 110a1 to the eighth wire 110a8 have a one-to-one correspondence.

In this modification, as a non-limiting example of pairs of two wires extending in directions crossing each other, two wires in each pair of wires cross each other to form an X shape. The first wire 110a1 to the eighth wire 110a8 may have any other arrangement configuration. As illustrated in FIG. 18, for example, the first wire 110a1 and the fifth wire 110a5 may be arranged to form a V shape. In this case, the first wire 110a1 and the fifth wire 110a5 may form a tapered shape that becomes wider toward the top from the left knee belt 112a. In addition, on the left knee belt 112a, the first wire 110a1 and the fifth wire 110a5 may be arranged in close proximity to each other in the manner illustrated in FIG. 18 or may be arranged away from each other in the manner illustrated in FIG. 19. The same applies to the other pairs of wires.

Figure 20:
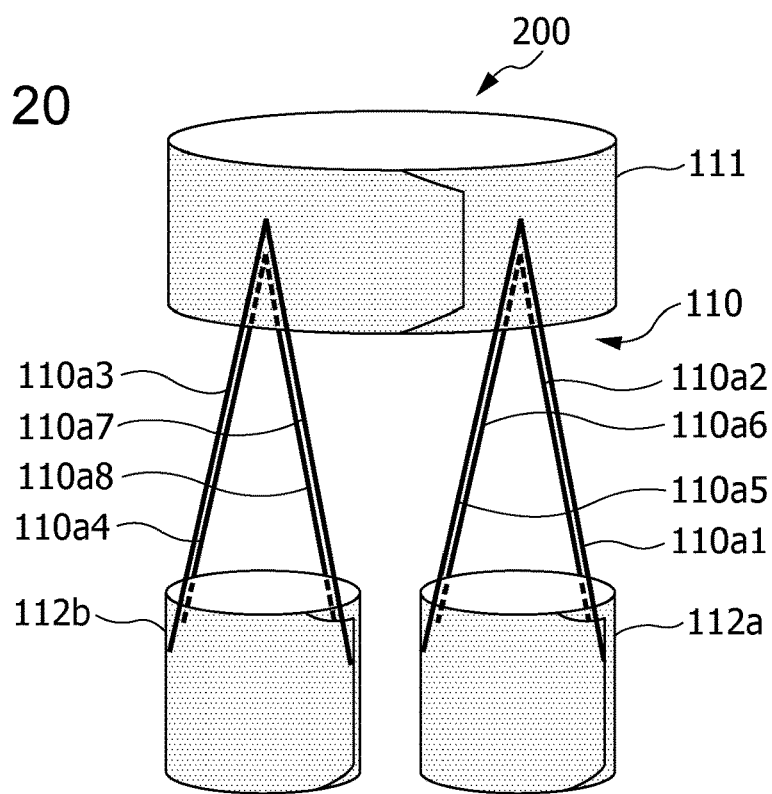
FIG. 20 is a diagram illustrating a modification of the arrangement of wires in the assistance apparatus illustrated in FIG. 13.
Figure 21:
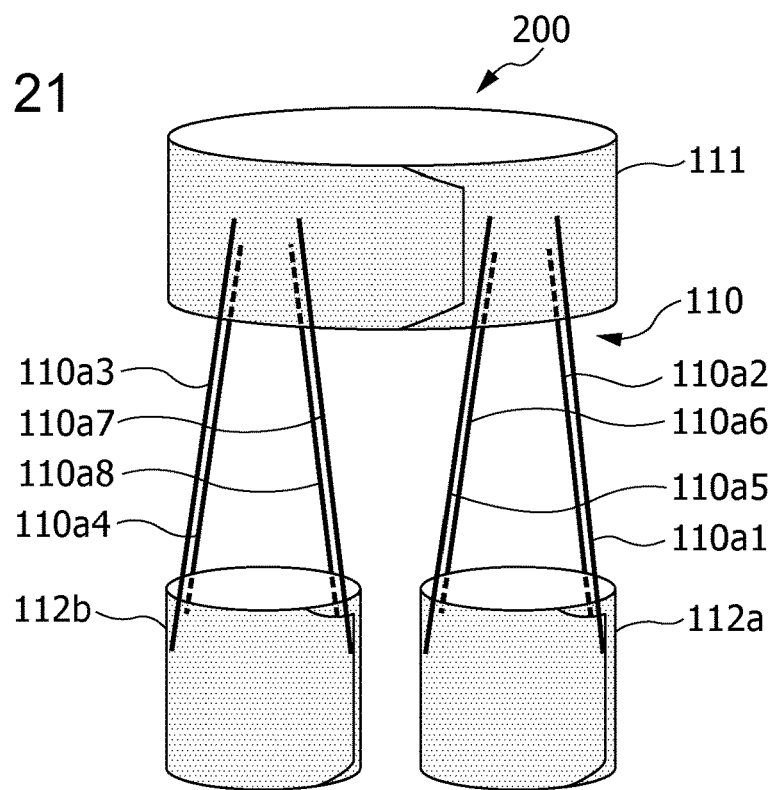
FIG. 21 is a diagram illustrating a modification of the arrangement of wires in the assistance apparatus illustrated in FIG. 13.

Alternatively, as illustrated in FIG. 20, for example, the first wire 110a1 and the fifth wire 110a5 may be arranged to form an inverted V shape. In this case, the first wire 110a1 and the fifth wire 110a5 may form a tapered shape that becomes narrower toward the top from the left knee belt 112a. In addition, on the upper-body belt 111, the first wire 110a1 and the fifth wire 110a5 may be arranged in close proximity to each other in the manner illustrated in FIG. 20 may be arranged away from each other in the manner illustrated in FIG. 21. The same applies to the other pairs of wires. FIG. 20 and FIG. 21 illustrate modifications of the arrangement of the wires 110 in the assistance apparatus 200 illustrated in FIG. 13.

In FIG. 13 to FIG. 15, the first wire 110a1 and the third wire 110a3 extending from the container 111a1 form an inverted V shape, the fifth wire 110a5 and the sixth wire 110a6 extending from the container 111a2 form an inverted V shape, the second wire 110a2 and the fourth wire 110a4 extending from the container 111a3 form an inverted V shape, and the seventh wire 110a7 and the eighth wire 110a8 extending from the container 111a4 form an inverted V shape. However, the arrangement of the first wire 110a1 to the eighth wire 110a8 on the upper-body belt 111 is not limited to the arrangement described above. For example, a wound portion of the first wire 110a1 and a wound portion of the third wire 110a3 may be arranged away from each other so that the two wires 110a1 and 110a3 do not cross each other or may be arranged so that the two wires 110a1 and 110a3 cross each other to form an X shape. A wound portion of the fifth wire 110a5 and a wound portion of the sixth wire 110a6 may be arranged away from each other so that the two wires 110a5 and 110a6 do not cross each other or may be arranged so that the two wires 110a5 and 110a6 cross each other to form an X shape. A wound portion of the second wire 110a2 and a wound portion of the fourth wire 110a4 may be arranged away from each other so that the two wires 110a2 and 110a4 do not cross each other or may be arranged so that the two wires 110a2 and 110a4 cross each other to form an X shape. A wound portion of the seventh wire 110a7 and a wound portion of the eighth wire 110a8 may be arranged away from each other so that the two wires 110a7 and 110a8 do not cross each other or may be arranged so that the two wires 110a7 and 110a8 cross each other to form an X shape.

In the assistance apparatus 200 described above, for example, the motor 114a1 generates a tension in the first wire 110a1, and the motor 114a5 generates a tension in the fifth wire 110a5. The assistance apparatus 200 drives the motor 114a1 to increase the tension of the first wire 110a1. Thus, a force is exerted on the leg of the user 1 in a direction in which the distance between the knee and the heel is reduced to assist a motion of the ankle of the user 1 during walking. The assistance apparatus 200 drives the motor 114a5 to increase the tension of the fifth wire 110a5. Thus, a force is exerted on the leg of the user 1 in a direction in which the distance between the knee and the heel is reduced to assist a motion of the ankle of the user 1 during walking. Further, by setting the tensions of the first wire 110a1 and the fifth wire 110a5 to different values, the assistance apparatus 200 can generate a moment of force regarding a left or right tilt of the heel of the user 1 and can assist a motion of the ankle of the user 1 during walking.

Figure 22A:
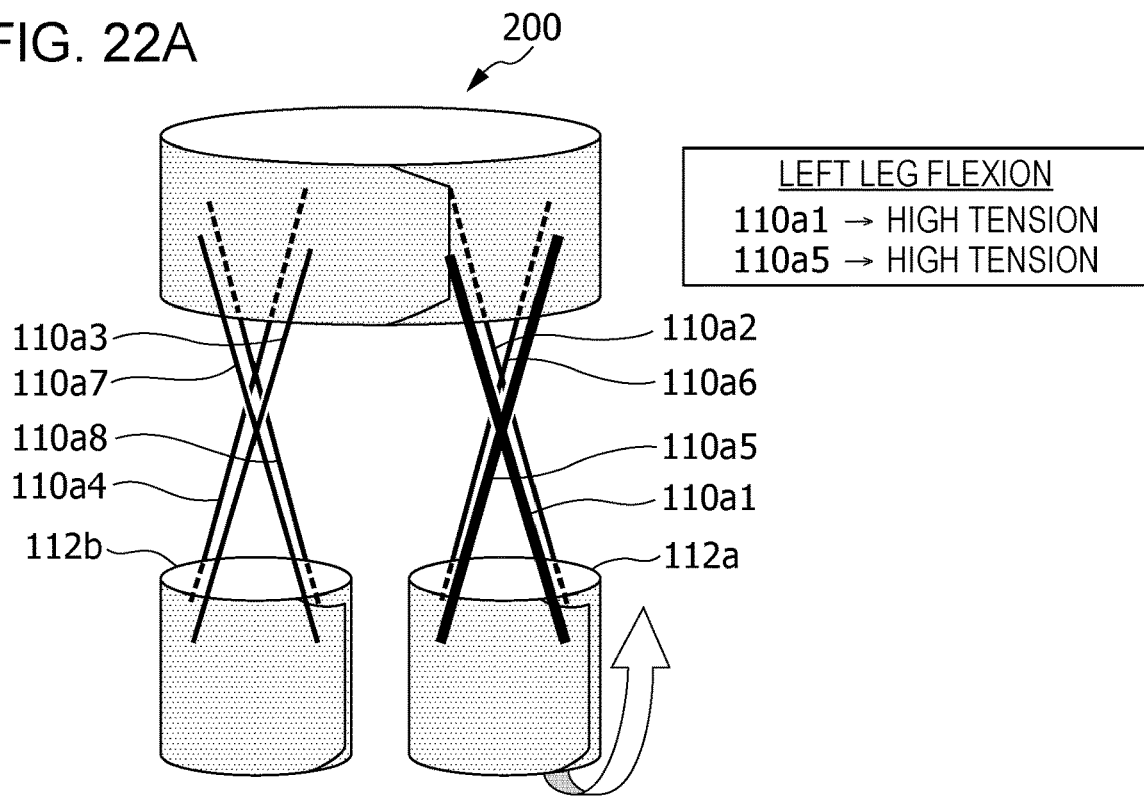
FIG. 22A is a diagram illustrating a case where the assistance apparatus according to the modification assists flexion of the hip joint of the left leg of the user.
Figure 22B:
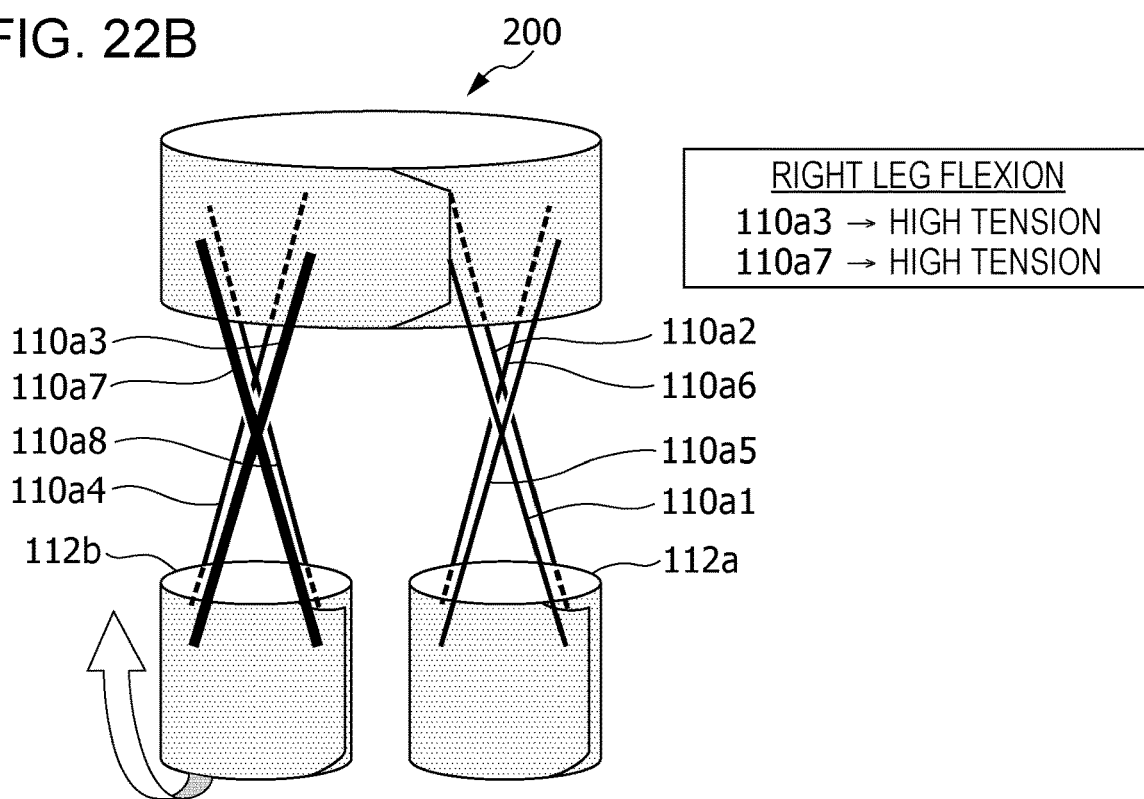
FIG. 22B is a diagram illustrating a case where the assistance apparatus according to the modification assists flexion of the hip joint of the right leg of the user.

The assistance apparatus 200 can apply an assistance force to the hip joint of the left leg and the hip joint of the right leg of the user 1 to flex and extend the hip joints. Referring to FIG. 22A, a case is illustrated in which the assistance apparatus 200 according to the modification assists flexion of the hip joint of the left leg of the user 1. Referring to FIG. 22B, a case is illustrated in which the assistance apparatus 200 according to the modification assists flexion of the hip joint of the right leg of the user 1. In FIG. 22A, to flex the left leg, the drive control unit 122 drives the motors 114a1 and 114a5 to increase the tensions of the first wire 110a1 and the fifth wire 110a5. In FIG. 22B, to flex the right leg, the drive control unit 122 drives the motors 114a3 and 114a7 to increase the tensions of the third wire 110a3 and the seventh wire 110a7. In this modification, the tensions of the first wire 110a1 and the fifth wire 110a5 are assumed to be equivalent, but may be different. In this modification, the tensions of the third wire 110a3 and the seventh wire 110a7 are assumed to be equivalent, but may be different.

Figure 23A:
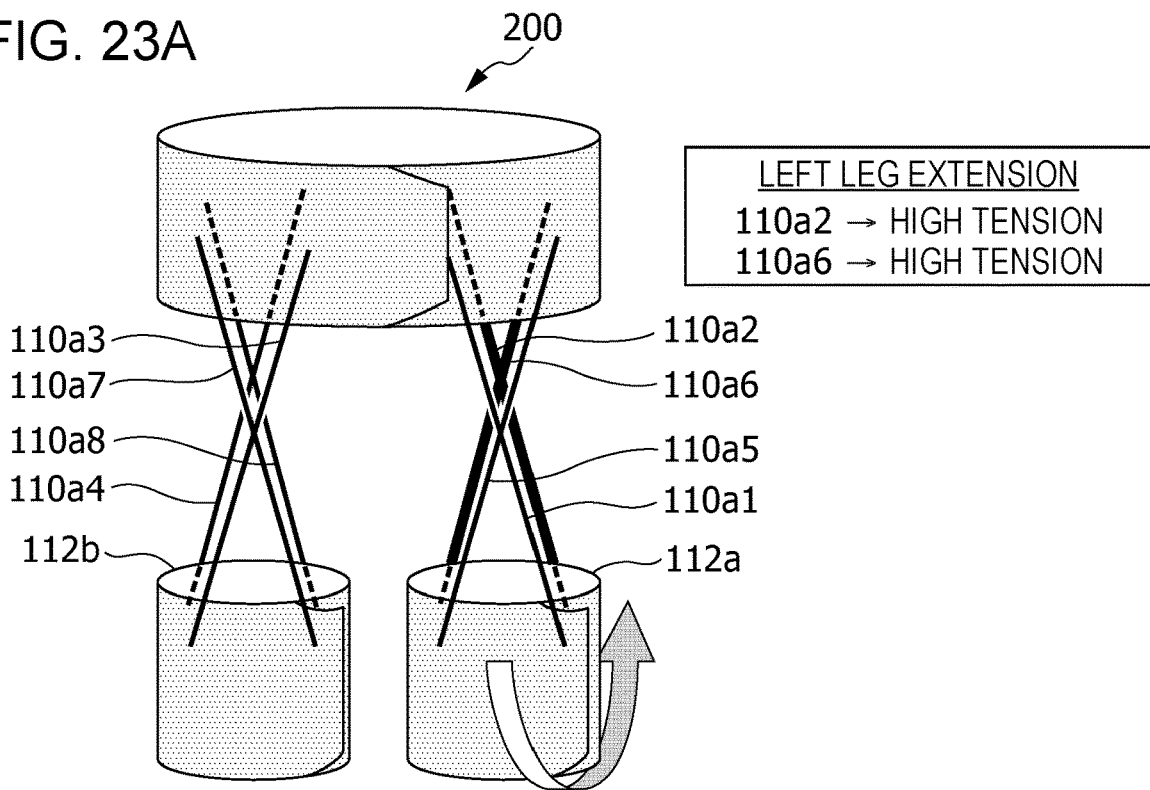
FIG. 23A is a diagram illustrating a case where the assistance apparatus according to the modification assists extension of the hip joint of the left leg of the user.
Figure 23B:
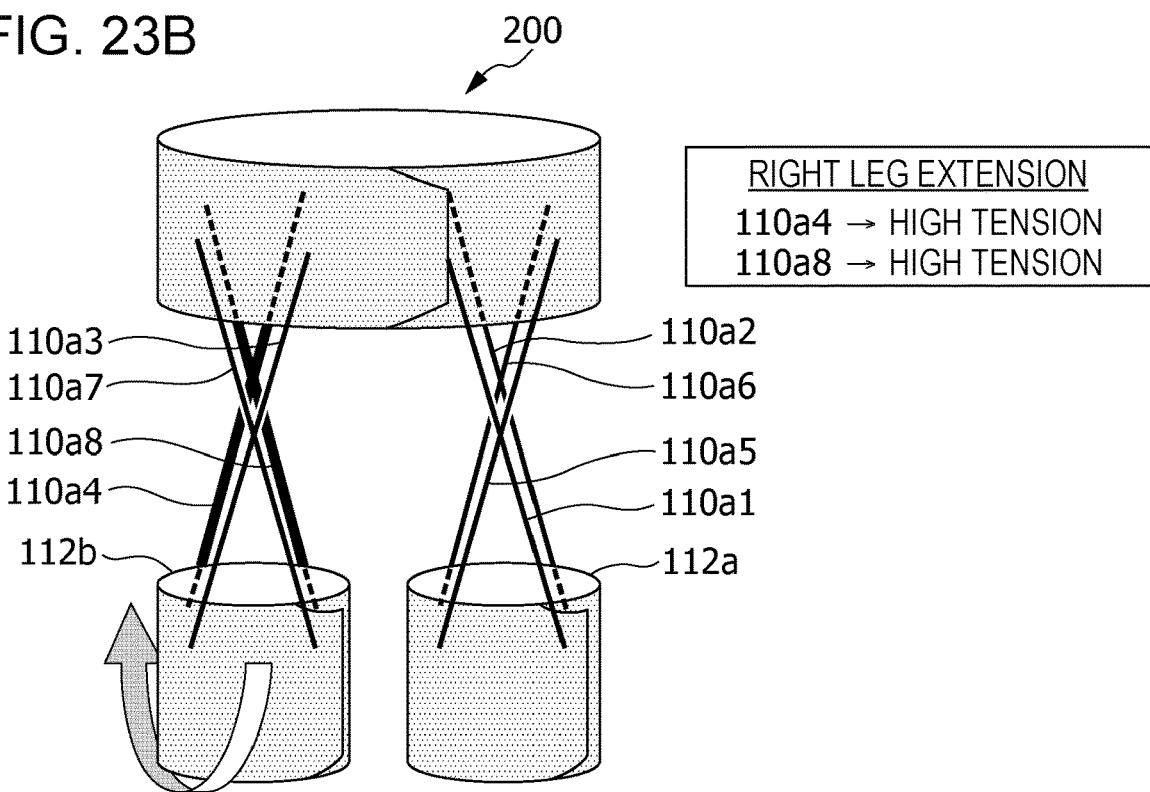
FIG. 23B is a diagram illustrating a case where the assistance apparatus according to the modification assists extension of the hip joint of the right leg of the user.

Referring to FIG. 23A, a case is illustrated in which the assistance apparatus 200 according to the modification assists extension of the hip joint of the left leg of the user 1. Referring to FIG. 23B, a case is illustrated in which the assistance apparatus 200 according to the modification assists extension of the hip joint of the right leg of the user 1. In FIG. 23A, to extend the left leg, the drive control unit 122 increases the tensions of the second wire 110a2 and the sixth wire 110a6. In FIG. 23B, to extend the right leg, the drive control unit 122 increases the tensions of the fourth wire 110a4 and the eighth wire 110a8. The tension of the second wire 110a2 for extension may be similar to the tension of the first wire 110a1 for flexion. The tension of the sixth wire 110a6 for extension may be similar to the tension of the fifth wire 110a5 for flexion. The tension of the fourth wire 110a4 for extension may be similar to the tension of the third wire 110a3 for flexion. The tension of the eighth wire 110a8 for extension may be similar to the tension of the seventh wire 110a7 for flexion.

In the foregoing description, the drive control unit 122 increases the tensions of two wires among the wires 110 to assist one motion of one leg. In this case, the drive control unit 122 may control the motors 114 to adjust the tensions of the wires 110 in accordance with a motion of the user 1 while keeping the tensions of the other six wires at the current value, or may stop the motors corresponding to the six wires so as not to exert the tensions on the six wires.

3. Operation of Assistance Apparatus 3-1. Overall Operation of Assistance Apparatus Next, the overall operation flow of an assistance apparatus will be described. Since the assistance apparatus 100 according to the embodiment and the assistance apparatus 200 according to the modification are similar in terms of the overall operation flow of an assistance apparatus, the operation of the assistance apparatus 100 according to the embodiment will be described, with no description given of the operation of the assistance apparatus 200 according to the modification. FIG. 24 is a flowchart illustrating the overall flow of an operation of the assistance apparatus 100 for assisting the user 1.

As illustrated in FIG. 3 and FIG. 24, in step S001, the control unit 120 of the assistance apparatus 100 acquires, or receives, an instruction for an operation mode from the user 1. The control unit 120 determines the operation mode of the assistance apparatus 100 in accordance with the acquired instruction. Specifically, the drive control unit 122 of the control unit 120 receives an instruction for an operation mode to be implemented by the assistance apparatus 100 from the input device 140 of the assistance apparatus 100 or from the terminal device 150. Examples of the operation mode include the normal walking mode, in which a user walks without an object such as an item like luggage, and the object transport walking mode, in which, a user walks with an object.

In step S002, the drive control unit 122 determines whether the instruction indicates the object transport walking mode. If the instruction indicates the object transport walking mode (Yes in step S002), the drive control unit 122 proceeds to step S003. If the instruction does not indicate the object transport walking mode (No in step S002), the drive control unit 122 proceeds to step S009.

In step S003, the grasp recognition unit 121 of the control unit 120 determines whether the user 1 is carrying an object. The grasp recognition unit 121 detects whether the user 1 is carrying an object on the basis of the sensor values acquired from the contact sensors 301*a* and 301*b* that the user 1 wears on their hands, and outputs a detection result to the drive control unit 122. If the grasp recognition unit 121 determines that the user 1 is carrying an object (Yes in step S003), the process proceeds to step S004. If the grasp recognition unit 121 determines that the user 1 is carrying no object (No in step S003), the process proceeds to step S007.

In step S004, the drive control unit 122 acquires a gait phase predicted by the gait timing detection unit 123. Further, in step S005, the drive control unit 122 controls the motors 114*a*1 to 114*a*4 on the basis of the acquired gait phase to generate tensions in the wires 110*a*1 to 110*a*4 of the assistance apparatus 100 in accordance with preset input profiles for assisting the user 1 in walking. The preset input profiles are stored in the storage unit 125. By generating tensions in the wires 110*a*1 to 110*a*4, the drive control unit 122 assists flexion and extension of the left and right legs of the user 1. At this time, the drive control unit 122 controls the tension of the wire 110*a*1 on the basis of the tension of the wire 110*a*1, which is acquired from the force sensor 115*a*1, controls the tension of the wire 110*a*2 on the basis of the tension of the wire 110*a*2, which is acquired from the force sensor 115*a*2, controls the tension of the wire 110*a*3 on the basis of the tension of the wire 110*a*3, which is acquired from the force sensor 115*a*3, and controls the tension of the wire 110*a*4 on the basis of the tension of the wire 110*a*4, which is acquired from the force sensor 115*a*4.

Further, the drive control unit 122 changes the balance, or ratio, of tensions to be generated in the wires 110*a*1 to 110*a*4, on the basis of a detection result of the grasp recognition unit 121. Then, the drive control unit 122 generates tensions in the wires 110*a*1 to 110*a*4 in accordance with input profiles in which the ratio has been changed. The input profiles in which the ratio has been changed may be stored in the storage unit 125 or may be calculated by the drive control unit 122.

For example, if the loads applied to the left and right hands of the user 1, which are detected by the grasp recognition unit 121, are equal, the drive control unit 122 makes the tension to be generated in the wire 110*a*1 equal to the tension to be generated in the wire 110*a*3, makes the tension to be generated in the wire 110*a*1 equal to the tension to be generated in the wire 110*a*4, makes the tension to be generated in the wire 110*a*2 equal to the tension to be generated in the wire 110*a*3, and makes the tension to be generated in the wire 110*a*2 equal to the tension to be generated in the wire 110*a*4. If the loads applied to the left and right hands of the user 1 are different, the drive control unit 122 makes the tension to be generated in the wire 110*a*1 different from the tension to be generated in the wire 110*a*3, makes the tension to be generated in the wire 110*a*1 different from the tension to be generated in the wire 110*a*4, makes the tension to be generated in the wire 110*a*2 different from the tension to be generated in the wire 110*a*3, or makes the tension to be generated in the wire 110*a*2 different from the tension to be generated in the wire 110*a*4. In this way, the assistance apparatus 100 assists a user in walking while carrying an object on the basis of loads applied to the left and right hands of the user. The expression "two loads being equal" is used to include not only a state in which the two loads are the same but also a state in which the difference between the two loads is within a range of several to ten or so percent (%).

Each input profile includes a timing at which a tension is generated in a wire during a gait cycle of the left leg, a period during which a tension is generated in the wire, the value of the tension of the wire during the period, a timing at which a tension is generated in a wire during a gait cycle of the right leg, a period during which a tension is generated in the wire, and the value of the tension of the wire during the period. The input profiles are set in advance and are stored in the storage unit 125. While receiving assistance provided by the assistance apparatus 100, the user 1 may adjust the timing of generation of a wire tension, the period of generation of the wire tension, and the value of the wire tension via the input device 140 or the terminal device 150. The drive control unit 122 may reflect the adjustment results to change the input profile, and may store the changed input profile in the storage unit 125. The drive control unit 122 may control the wire tension by using the changed input profile.

Then, in step S006, the drive control unit 122 determines whether a stop instruction for stopping assistance provided by the assistance apparatus 100 has been acquired from the user 1. If the stop instruction has been acquired (Yes in step S006), the drive control unit 122 stops the operation of the assistance apparatus 100 and terminates the series of processes. If no stop instruction is acquired (No in step S006), the process returns to step S003. The stop instruction may be an instruction for changing the operation mode.

By repeatedly performing the operations of steps S003 to S006, the drive control unit 122 controls wire tensions by using input profiles in which the balance of the tensions to be generated in the wires 110*a*1 to 110*a*4 has been changed in accordance with a difference between the loads applied to the left and right hands of the user 1 and so on. Thus, even if the relationship between the loads applied to the left and right hands is changed, the drive control unit 122 controls wire tensions in accordance with the changed relationship.

In step S007, the drive control unit 122 acquires a gait phase predicted by the gait timing detection unit 123. Further, in step S008, the drive control unit 122 controls the motors 114*a*1 to 114*a*4 on the basis of the acquired gait phase to generate tensions in the wires 110a1 to 110a4 in accordance with preset input profiles for assisting the user 1 in walking. The drive control unit 122 controls the tension of the wire 110a1 on the basis of the tension of the wire 110a1, which is acquired from the force sensor 115a1, controls the tension of the wire 110a2 on the basis of the tension of the wire 110a2, which is acquired from the force sensor 115a2, controls the tension of the wire 110a3 on the basis of the tension of the wire 110a3, which is acquired from the force sensor 115a3, and controls the tension of the wire 110a4 on the basis of the tension of the wire 110a4, which is acquired from the force sensor 115a4, to assist flexion and extension of the left and right legs of the user 1. In addition, the drive control unit 122 does not acquire the loads applied to the left and right hands of the user 1 from the grasp recognition unit 121 and thus controls the tensions of the wires 110a1 to 110a4 in accordance with input profiles similar to those when the loads applied to the left and right hands of the user 1 are equal. In this way, the assistance apparatus 100 assists a user in walking while carrying no object. After step S008, the drive control unit 122 proceeds to step S006.

In step S009 and the subsequent steps, the drive control unit 122 operates in the normal walking mode. In step S009, the drive control unit 122 acquires a gait phase predicted by the gait timing detection unit 123. Then, in step S010, the drive control unit 122 controls the motors 114a1 to 114a4 on the basis of the acquired gait phase to generate tensions in the wires 110a1 to 110a4 in accordance with preset input profiles for assisting the user 1 in walking. The input profiles used in step S010 may be the same as the input profiles used in step S008. The drive control unit 122 controls the tensions of the wires 110a1 to 110a4 on the basis of the tensions of the wires 110a1 to 110a4, which are respectively acquired from the force sensors 115a1 to 115a4, to assist flexion and extension of the left and right legs of the user 1. In this way, the assistance apparatus 100 assists a user in walking while carrying no object.

Then, in step S011, the drive control unit 122 determines whether a stop instruction for stopping assistance provided by the assistance apparatus 100 has been acquired from the user 1. If the stop instruction has been acquired (Yes in step S011), the drive control unit 122 stops the operation of the assistance apparatus 100 and terminates the series of processes. If no stop instruction is acquired (No in step S011), the process returns to step S009. The stop instruction may be an instruction for changing the operation mode.

As described above, the assistance apparatus 100 assists a user in walking in accordance with the normal walking mode or the object transport walking mode, which is selected by the user. In the object transport walking mode, the assistance apparatus 100 changes the balance of the tensions to be generated in the wires 110a1 to 110a4 in accordance with, for example, the loads applied to the left and right hands of a user who is carrying an object, and assists the user in accordance with the state of the user.

3-2. Details of Assistance Operation of Assistance Apparatus

The assistance operation of an assistance apparatus will be described in detail. The following describes an operation of an assistance apparatus for assisting a user in walking when the user walks forward while carrying, or holding, an object such as an item. Specifically, the following describes a relationship between a wire for which a tension is to be increased and the timing of increasing the tension of the wire in assistance for flexion and extension of each of the left and right legs of a user who is walking forward. The operation of the assistance apparatus 100 according to the embodiment and the operation of the assistance apparatus 200 according to the modification are the same, except that the number of wires in which tensions are to be generated for assistance for flexion and extension and maximum tension values are different. Thus, the following describes the operation of the assistance apparatus 100 according to the embodiment, with no description given of the operation of the assistance apparatus 200 according to the modification.

Figure 25:
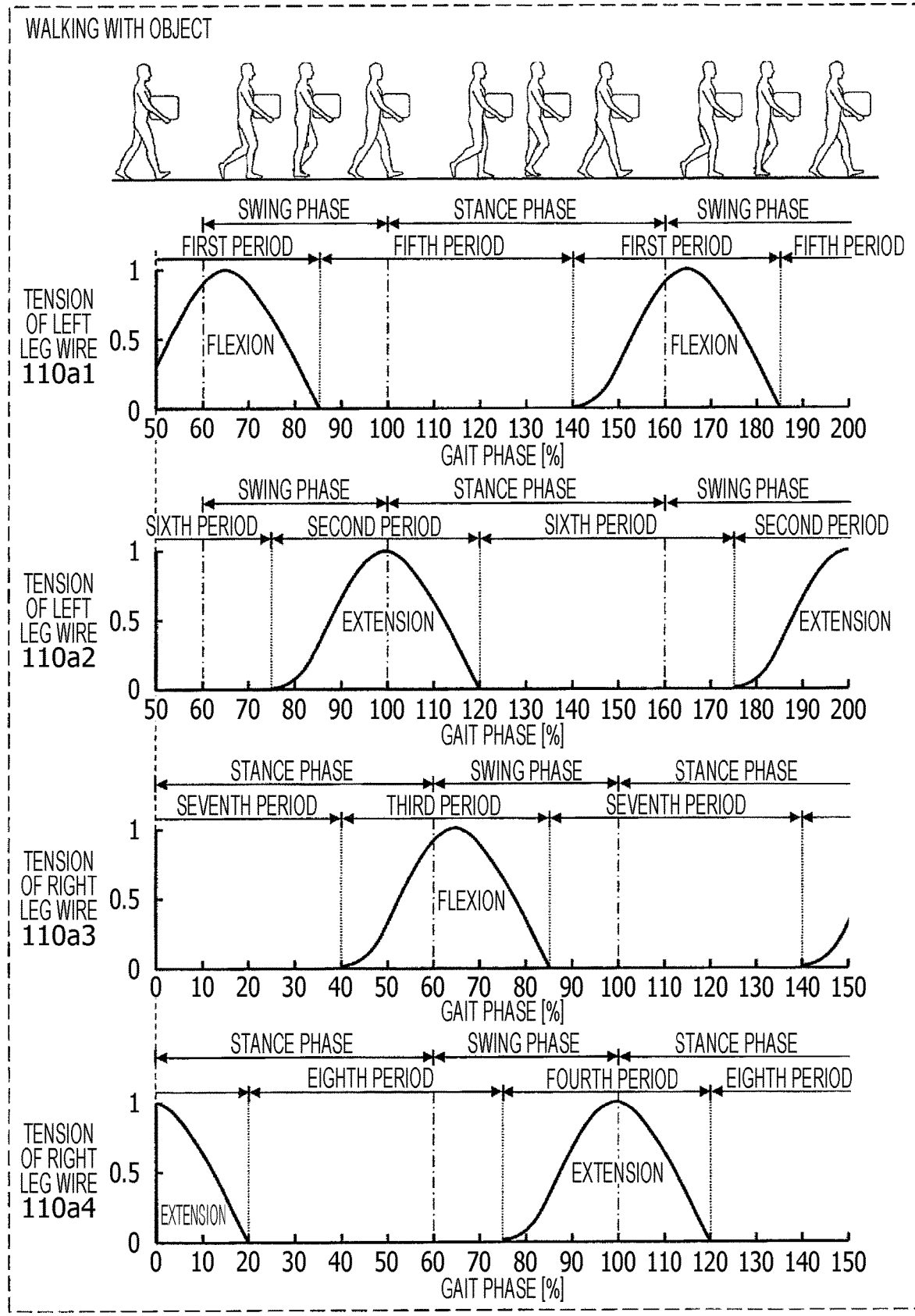
FIG. 25 is a diagram illustrating an example operation of the assistance apparatus according to the embodiment for assisting a user in walking forward while carrying an object.

The drive control unit 122 of the assistance apparatus 100 determines, based on a wire-tension relationship for a type of assistance, namely, either of flexion and extension, wires in which tensions are to be generated, pulling tensions of the wires, and the timing at which and the period during which the tensions of the wires are generated, and assists motions of the user. For example, FIG. 25 illustrates an example operation of the assistance apparatus 100 for assisting a user in walking forward while carrying an object. FIG. 25 illustrates a case where the loads applied to the left and right hands of the user are equal. Also when assisting a user in walking forward while carrying no object, the assistance apparatus 100 operates in a way similar to that in the example illustrated in FIG. 25.

In FIG. 25, a relationship is illustrated among a gait state of a user, a gait phase of each leg, and the swing phase and stance phase of each leg. In the illustration of FIG. 25, the gait phase of each leg, wires in which tensions are to be generated, and the states of the tensions of the wires, that is, the input profiles of wire tensions, are associated with each other. An input profile of a wire tension represents the ratio of a wire tension to a maximum tension to be generated in each wire (also referred to as tension gain). For example, when the tension gain of each wire is 100 N, a tension to be actually generated is represented by an expression of a tension value included in the input profile×tension gain. During a period of 0 to 100% of a gait phase, the assistance apparatus 100 produces a wire tension while changing the wire tension, with a maximum tension being 100 N.

In the example illustrated in FIG. 25, the assistance apparatus 100 assists both flexion and extension of the left and right legs of the user. As described above, the assistance apparatus 100 generates a tension in the wire 110a1 to apply an assistance force for flexion to the left leg, and generates a tension in the wire 110a2 to apply an assistance force for extension to the left leg. The assistance apparatus 100 generates a tension in the wire 110a3 to apply an assistance force for flexion to the right leg, and generates a tension in the wire 110a4 to apply an assistance force for extension to the right leg. The assistance apparatus 100 may assist either flexion or extension of the left and right legs of the user, instead of both flexion and extension of the left and right legs of the user.

In FIG. 25, the gait phase of the right leg is used as a reference gait phase. In the gait phase of the right leg, heel strike of the right leg occurs at 0%, and heel strike of the left leg occurs at 50%. In this embodiment, as a non-limiting example, a time point of 0% of the gait phase of the right leg corresponds to a time point of 50% of the gait phase of the left leg. In the example illustrated in FIG. 25, the gait phase of the right leg is used as a reference gait phase, for convenience of illustration. The gait phase of either leg may be used as a reference gait phase, and the gait phase of one leg need not be used as a reference gait phase.

The stance phase of the right leg is a period of 0% or more and 60% or less of the gait phase of the right leg, and the swing phase of the right leg is a period of more than 60% and less than 100% of the gait phase of the right leg.

The swing phase of the left leg is a period of more than 60% and less than 100% of the gait phase of the left leg, and the stance phase of the left leg is a period of 100% or more and 160% or less of the gait phase of the left leg. In the gait phase of the left leg, a period of more than 60% and less than 100% of the gait phase of the left leg, which is the swing phase of the left leg, is included in a first gait cycle of the left leg, and a period of 100% or more and 160% or less of the gait phase of the left leg, which is the stance phase of the left leg, is included in a second gait cycle of the left leg, which is subsequent to the first gait cycle of the left leg. That is, a period of 100% or more and 160% or less of the gait phase of the left leg corresponds to a period of 0% or more and 60% or less of the second gait phase of the left leg. In the following description, a gait phase represented using a value greater than or equal to 100% means a gait phase subsequent to a gait phase represented using a value of 0% to 100%. In FIG. 25, furthermore, a gait phase represented using a value over 100% may be converted into a value of 0% to 100% and represented using the value of 0% to 100%.

When assisting the user in walking forward, for example, the assistance apparatus 100 applies an assistance force for flexion to the left leg at a timing of about 40% of the gait phase of the left leg. A timing of about 40% of the gait phase of the left leg is included in the stance phase of the left leg and the swing phase of the right leg. Specifically, a timing of about 40% of the gait phase of the left leg is a timing immediately before the right leg touches the ground during the swing phase. At this time, the center of gravity of the body of the user shifts forward. When assisting the user in walking forward, for example, the assistance apparatus 100 applies an assistance force for flexion to the right leg at a timing of about 40% of the gait phase of the right leg. A timing of about 40% of the gait phase of the right leg is included in the swing phase of the left leg and the stance phase of the right leg. Specifically, a timing of about 40% of the gait phase of the right leg is a timing immediately before the left leg touches the ground during the swing phase. At this time, the center of gravity of the body of the user shifts forward.

Further, the assistance apparatus 100 applies an assistance force for extension to the left leg at a timing of about 75% of the gait phase of the left leg, for example. A timing of about 75% of the gait phase of the left leg is included in the swing phase of the left leg and the stance phase of the right leg. Specifically, a timing of about 75% of the gait phase of the left leg is a timing in the middle of moving the left leg of the user forward during the swing phase and is included in the period during which the center of gravity of the body of the user shifts from backward to forward. Further, the assistance apparatus 100 applies an assistance force for extension to the right leg at a timing of about 75% of the gait phase of the right leg, for example. A timing of about 75% of the gait phase of the right leg is included in the stance phase of the left leg and the swing phase of the right leg. Specifically, a timing of about 75% of the gait phase of the right leg is a timing in the middle of moving the right leg of the user forward during the swing phase and is included in the period during which the center of gravity of the body of the user shifts from backward to forward.

When assisting the user in walking forward, the assistance apparatus 100 generates a tension greater than or equal to a first threshold value in each of the wires 110a1 to 110a4. In the example illustrated in FIG. 25, the respective tensions of the wires 110a1 to 110a4 are 100 N, for example. The first threshold value may be a tension value that allows the user to recognize that flexion or extension is promoted by a tension generated in a wire. The first threshold value is, for example, 40 N, which is 40% of 100 N. In the example illustrated in FIG. 25, the assistance apparatus 100 generates a wire tension in each of the wires 110a1 to 110a4 in such a manner that the wire tension gradually increases, reaches a maximum tension, and then gradually decreases during the period of generation of the wire tension. The input profiles of the wire tensions generated in the wires 110a1 to 110a4 by the assistance apparatus 100 each exhibit a waveform that is convex curve. In this example, the maximum tension is 100 N.

To assist flexion of the left leg, for example, the assistance apparatus 100 continuously generates a tension in the wire 110a1 during the entirety of a first period, which is a period of 40% or more and 85% or less of the gait phase of the left leg. Then, the assistance apparatus 100 generates a tension greater than or equal to the first threshold value in the wire 110a1 during at least a portion of the first period. In the first period, the left leg shifts from the stance phase to the swing phase. Applying an assistance force for flexion to the left leg in the shift from the stance phase to the swing phase allows the user to easily raise the left leg and ensures that the user can easily walk.

In the example illustrated in FIG. 25, the assistance apparatus 100 generates no tension in the wire 110a1 during a fifth period, which is a period other than the first period. The fifth period may be a period of 0% or more and less than 40% of the gait phase of the left leg and a period of more than 85% and less than 100% of the gait phase of the left leg. However, the assistance apparatus 100 may generate a tension during the fifth period. For example, the assistance apparatus 100 may generate a tension less than a fourth threshold value in the wire 110a1 during the fifth period. The fourth threshold value is a tension value that is smaller than the first threshold value and that is not perceivable by the user, for example. For example, the fourth threshold value may be a tension value that prevents the wire 110a1 from loosening. The fourth threshold value is a value that is 0.2 to 0.4 times the first threshold value or is 10 N, for example. In the specification and the appended claims, generation of a tension less than the fourth threshold value means generation of a tension greater than or equal to 0 and less than the fourth threshold value and includes generation of a tension of 0.

The start timing of the first period may be included in a period of 35% or more and 55% or less of the gait phase of the left leg. The end timing of the first period may be included in a period of 80% or more and 90% or less of the gait phase of the left leg. In the example illustrated in FIG. 25, the wire tension is maximum at a timing of 65% of the gait phase of the left leg. However, the wire tension may be maximum at a time during a period of 60% or more and 70% or less of the gait phase of the left leg. Thus, the first period may be a period of 35% or more and 90% or less of the gait phase of the left leg.

To assist extension of the left leg, for example, the assistance apparatus 100 continuously generates a tension in the wire 110a2 during the entirety of a second period, which is a period of 75% or more and 120% or less of the gait phase of the left leg. Then, the assistance apparatus 100 generates a tension greater than or equal to the first threshold value in the wire 110a2 during at least a portion of the second period. In the second period, the left leg shifts from the swing phase to the stance phase. Applying an assistance force for extension to the left leg in the shift from the swing phase to the stance phase allows the left leg of the user to touch the ground stably and ensures that the user can easily walk. In the example illustrated in FIG. 25, the assistance apparatus 100 generates no tension in the wire 110a2 during a sixth period, which is a period other than the second period. The sixth period may be a period of more than 20% and less than 75% of the gait phase of the left leg. However, the assistance apparatus 100 may generate a tension less than the fourth threshold value during the sixth period.

The start timing of the second period may be included in a period of 65% or more and 90% or less of the gait phase of the left leg. The end timing of the second period may be included in a period of 110% or more and 125% or less of the gait phase of the left leg. In the example illustrated in FIG. 25, the wire tension is maximum at a timing of 100% of the gait phase of the left leg. However, the wire tension may be maximum at a time during a period of 85% or more and 100% or less of the gait phase of the left leg. Thus, the second period may be a period of 65% or more and 125% or less of the gait phase of the left leg, that is, may include a period of 0% or more and 25% or less of the gait phase of the left leg and a period of 65% or more and less than 100% of the gait phase of the left leg.

To assist flexion of the right leg, for example, the assistance apparatus 100 continuously generates a tension in the wire 110a3 during the entirety of a third period, which is a period of 40% or more and 85% or less of the gait phase of the right leg. Then, the assistance apparatus 100 generates a tension greater than or equal to the first threshold value in the wire 110a3 during at least a portion of the third period. In the third period, the right leg shifts from the stance phase to the swing phase. In the example illustrated in FIG. 25, the assistance apparatus 100 generates no tension in the wire 110a3 during a seventh period, which is a period other than the third period. However, the assistance apparatus 100 may generate a tension less than the fourth threshold value during the seventh period. The seventh period may be a period of 0% or more and less than 40% of the gait phase of the right leg and a period of more than 85% and less than 100% of the gait phase of the right leg.

The start timing of the third period may be included in a period of 35% or more and 55% or less of the gait phase of the right leg. The end timing of the third period may be included in a period of 80% or more and 90% or less of the gait phase of the right leg. In the example illustrated in FIG. 25, the wire tension is maximum at a timing of 65% of the gait phase of the right leg. However, the wire tension may be maximum at a time during a period of 60% or more and 70% or less of the gait phase of the right leg. Thus, the third period may be a period of 35% or more and 90% or less of the gait phase of the right leg.

To assist extension of the right leg, for example, the assistance apparatus 100 continuously generates a tension in the wire 110a4 during the entirety of a fourth period, which is a period of 75% or more and 120% or less of the gait phase of the right leg. Then, the assistance apparatus 100 generates a tension greater than or equal to the first threshold value in the wire 110a4 during at least a portion of the fourth period. In the fourth period, the right leg shifts from the swing phase to the stance phase. In the example illustrated in FIG. 25, the assistance apparatus 100 generates no tension in the wire 110a4 during an eighth period, which is a period other than the fourth period. The eighth period may be a period of more than 20% and less than 75% of the gait phase of the right leg. However, the assistance apparatus 100 may generate a tension less than the fourth threshold value during the eighth period.

The start timing of the fourth period may be included in a period of 65% or more and 90% or less of the gait phase of the right leg. The end timing of the fourth period may be included in a period of 110% or more and 125% or less of the gait phase of the right leg. In the example illustrated in FIG. 25, the wire tension is maximum at a timing of 100% of the gait phase of the right leg. However, the wire tension may be maximum at a time during a period of 85% or more and 100% or less of the gait phase of the right leg. Thus, the fourth period may be a period of 65% or more and 125% or less of the gait phase of the right leg, that is, may include a period of 0% or more and 25% or less of the gait phase of the right leg and a period of 65% or more and less than 100% of the gait phase of the right leg.

As described above, during the entirety of a period corresponding to each input profile of a wire tension, the assistance apparatus 100 continuously generates a tension in the wire corresponding to the input profile. However, the embodiment is not limited to this. The assistance apparatus 100 may temporarily stop the generation of the tension in the wire during the period corresponding to the input profile. In this case, a load imposed on the leg of the user by the assistance apparatus 100 is reduced, and the load felt by the user on which the assistance apparatus 100 acts is reduced.

The input profiles of wire tensions illustrated in FIG. 25 are set so that the tension of each wire rises earlier than a desired time point by several percent (%) of the gait phase in consideration of a time delay from when the drive control unit 122 outputs a signal to the corresponding motor to when a tension is actually generated in the wire. For example, in the example illustrated in FIG. 25, input profiles of wire tensions are created so that the tension of each wire rises earlier than a desired time point by approximately 5%. For assistance for flexion, the assistance apparatus 100 provides assistance so that the assistance for flexion is completed immediately before the heel strikes the ground. Thus, input profiles of wire tensions are created so that assistance for flexion ends at a time during a period of 80% or more and 90% or less of the gait phase of the each leg in order to complete assistance for flexion at a timing of about 100% of the gait phase of each leg in consideration of a delay of output of the tension of each wire.

As described above, in the example illustrated in FIG. 25, a case is illustrated in which the loads applied to the left and right hands of the user are equal. However, when the loads applied to the left and right hands of the user are different, the assistance apparatus 100 controls the tensions of the wires 110 by using input profiles different from the input profiles of the wire tensions illustrated in FIG. 25.

Specifically, the assistance apparatus 100 detects loads applied to the left and right hands of a user who is carrying an object, on the basis of sensor values acquired from the contact sensors 301a and 301b. Further, the assistance apparatus 100 changes the input profiles of the wire tensions illustrated in FIG. 25 on the basis of a difference between the loads applied to the left and right hands, and controls the tensions of the wires 110a1 to 110a4 by using the changed input profiles to assist the user in walking.

For example, as illustrated in FIG. 26A to FIG. 26C, the loads applied to the left and right hands of the user vary depending on how the user carries an object. FIG. 26A to FIG. 26C are diagrams illustrating examples of how a user carries an object.

In the example illustrated in FIG. 26A, the user 1 wearing the assistance apparatus 100 carries an object A in such a manner that the object A is held in the left and right hands at an equal height positions. That is, the user 1 carries the object A with the left and right arms kept in balanced postures. In this case, the loads applied to the left and right hands of the user 1 are equal. Thus, the drive control unit 122 controls the tensions of the wires 110a1 to 110a4 by using the input profiles of the wire tensions illustrated in FIG. 25.

In the input profiles illustrated in FIG. 25, the input profile of the tension of the wire 110a1 during the first period in the gait phase of the left leg and the input profile of the tension of the wire 110a3 during the third period in the gait phase of the right leg are similar. That is, the maximum tension of the wire 110a1 in the first period and the maximum tension of the wire 110a3 in the third period are equal.

Further, the input profile of the tension of the wire 110a2 during the second period in the gait phase of the left leg and the input profile of the tension of the wire 110a4 during the fourth period in the gait phase of the right leg are similar. That is, the maximum tension of the wire 110a2 in the second period and the maximum tension of the wire 110a4 in the fourth period are equal.

In the example illustrated in FIG. 26B, the user 1 wearing the assistance apparatus 100 carries an object A in such a manner that the object A is held in the left and right hands at unequal height positions. Specifically, the height position of the right hand is higher than the height position of the left hand. In this case, the load applied to the left hand of the user 1 is larger than the load applied to the right hand of the user 1. Accordingly, the center of gravity of the body of the user 1 shifts leftward from the center, resulting in an increase in the load on the left leg of the user 1. Thus, the drive control unit 122 uses input profiles of the wire tensions obtained by changing the input profiles of the wire tensions illustrated in FIG. 25 in such a manner that the tensions of the wires 110a1 and 110a2 of the left leg are greater than the tensions of the wires 110a3 and 110a4 of the right leg. In this embodiment, the relationship between the tension of the wires 110a1 and 110a2 of the left leg and the tension of the wires 110a3 and 110a4 of the right leg is defined on the basis of the tension ratio, as a non-limiting example. Alternatively, for example, the relationship may be defined on the basis of the tension difference.

Specifically, in the case described above, the ratio of the tension of the wires 110a1 and 110a2 of the left leg to the tension of the wires 110a3 and 110a4 of the right leg is represented as a first ratio. That is, first ratio=(tension of wire of left leg)/(tension of wire of right leg) holds. The first ratio is set to any value in the range of 1.2 or more and 2.0 or less. The first ratio increases as the difference between the load applied to the left hand and the load applied to the right hand increases. However, the first ratio may be a fixed value. When the first ratio is a fixed value, the first ratio may be determined in advance and stored in the storage unit 125, or may be determined by the user 1 through the input device 140 or the terminal device 150 and stored in the storage unit 125. For example, in the input device 140 illustrated in FIG. 8, the "left-handed" button 145 and the "right-handed" button 146 may have a function of decreasing and increasing the first ratio.

The first ratio includes the tensions of a pair of wires of the left and right legs, which are used to assist the same motion. Examples of the tensions of a pair of wires making up the first ratio include a pair of the maximum tension of the wire 110a1 in the first period during the gait phase of the left leg and the maximum tension of the wire 110a3 in the third period during the gait phase of the right leg, and a pair of the maximum tension of the wire 110a2 in the second period during the gait phase of the left leg and the maximum tension of the wire 110a4 in the fourth period during the gait phase of the right leg.

Figure 27:
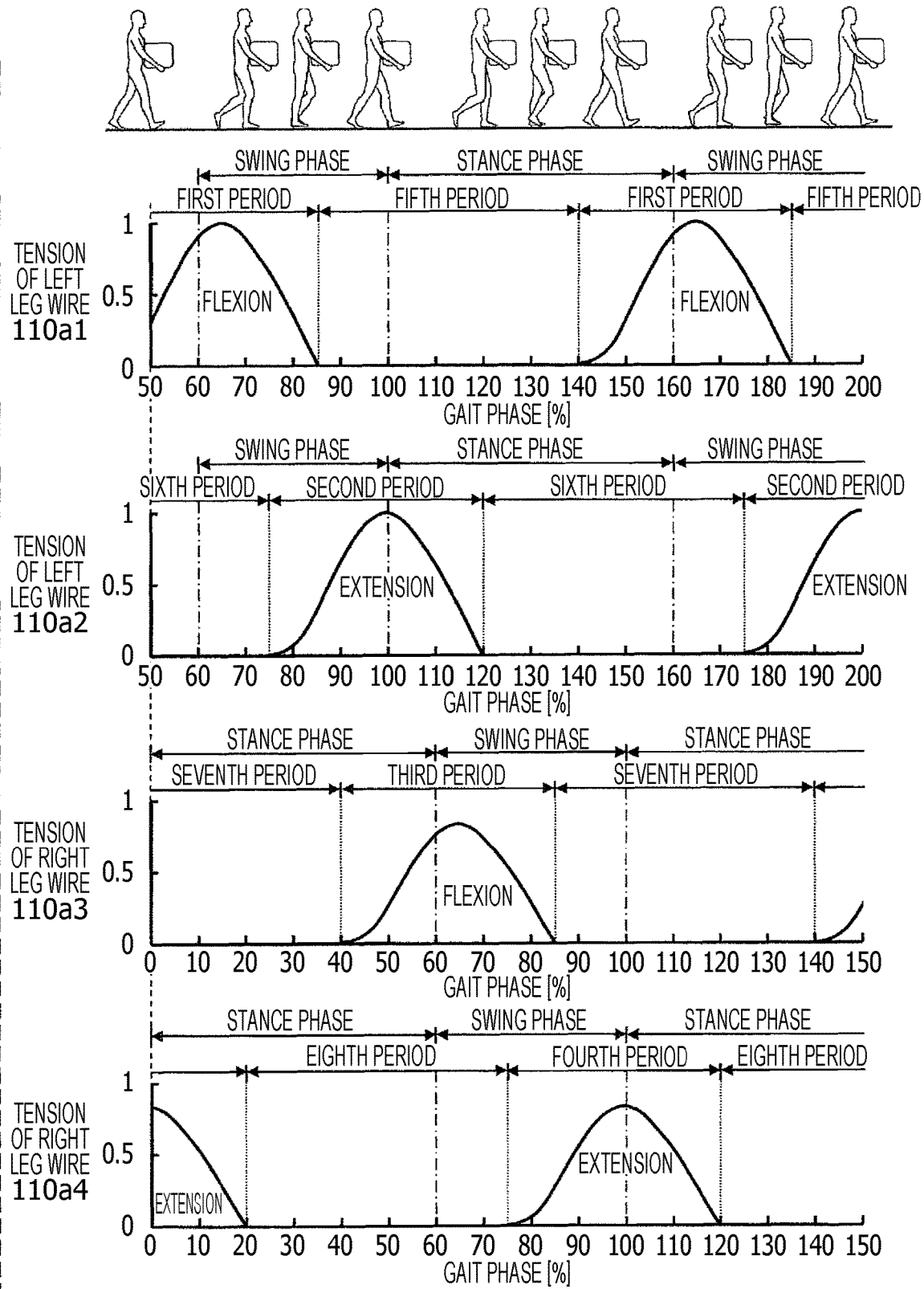
FIG. 27 is a diagram illustrating an example operation of the assistance apparatus according to the embodiment for assisting a user in walking forward while carrying an object in such a manner that the load applied to the left hand is larger than the load applied to the right hand.

In the example illustrated in FIG. 26B, the first ratio is set to, for example, "1.2". In this case, the drive control unit 122 controls the tensions of the wires 110 in accordance with input profiles of wire tensions illustrated in FIG. 27. FIG. 27 is a diagram illustrating an example operation of the assistance apparatus 100 for assisting a user in walking forward while carrying an object in such a manner that the load applied to the left hand is larger than the load applied to the right hand. In the example illustrated in FIG. 27, the maximum tensions to be generated in the wires 110a1 and 110a2 of the left leg are 100 N, and the maximum tensions to be generated in the wires 110a3 and 110a4 of the right leg are 83 N. The waveforms of the input profiles of the tensions of the wires 110a3 and 110a4 are entirely changed in accordance with the reduced maximum tensions. In the example illustrated in FIG. 27, the tension generation timings, the tension generation periods, and the timings at which the tensions are maximum in the waveforms of the input profiles of the tensions of the wires 110a3 and 110a4 remain unchanged from those illustrated in FIG. 25.

In the example illustrated in FIG. 27, the tension of the wire 110a1 in the first period, which is represented by $f1(\theta)$, the tension of the wire 110a2 in the second period, which is represented by $f2(\theta)$, the tension of the wire 110a3 in the third period, which is represented by $f3(\theta)$, and the tension of the wire 110a4 in the fourth period, which is represented by $f4(\theta)$, where $\theta$ denotes a gait phase, may be defined as follows: $f1(\theta)/f3(\theta)$=first ratio, $f2(\theta)/f4(\theta)$=first ratio, and first ratio=1.2. Note that the gait phase $\theta$ may not include a gait phase in which tension application is started. Note that the gait phase $\theta$ may not include a gait phase in which tension application is finished.

Accordingly, the drive control unit 122 makes the tension of the wire 110a1 in the first period during the gait phase of the left leg and the tension of the wire 110a2 in the second period during the gait phase of the left leg greater than the tension of the wire 110a3 in the third period during the gait phase of the right leg and the tension of the wire 110a4 in the fourth period during the gait phase of the right leg.

As illustrated in FIG. 27, making the maximum tensions of the wires 110a1 and 110a2 of the left leg greater than the maximum tensions of the wires 110a3 and 110a4 of the right leg is most effective to assist a user in walking. The user receives a larger assistance force at the left leg, which bears a larger load, and a smaller assistance force at the right leg, which bears a smaller load, and can thus smoothly walk while feeling uniform loads being imposed on the left and right legs. Further, there is a tendency that the center of gravity of the body of a user who carries an object is moved forward. Accordingly, increasing the tensions to be generated in the wires 110a2 and 110a4 in the back part of the body of the user to increase an assistance force for extension is effective to keep the center of gravity of the body of the user in the upright state. Thus, only the maximum tension of the wire 110a2 of the left leg may be made larger than the maximum tensions of the wires 110a3 and 110a4 of the right leg, and the maximum tension of the wire 110a1 of the left leg may be made equal to the maximum tensions of the wires 110a3 and 110a4 of the right leg. Also in this case, a user who carries an object can feel relatively uniform loads being imposed on the left and right legs.

When the load applied to the right hand of the user 1 is larger than the load applied to the left hand of the user 1, the first ratio is given by (tension of wire of right leg)/(tension of wire of left leg). The assistance apparatus 100 provides assistance based on the first ratio in such a manner that the tensions to be generated in the wires 110a3 and 110a4 of the right leg are greater than the tensions to be generated in the wires 110a1 and 110a2 of the left leg.

Accordingly, the drive control unit 122 makes the tension of the wire 110a3 in the third period during the gait phase of the right leg and the tension of the wire 110a4 in the fourth period during the gait phase of the right leg greater than the tension of the wire 110a1 in the first period during the gait phase of the left leg and the tension of the wire 110a2 in the second period during the gait phase of the left leg.

Figure 28:
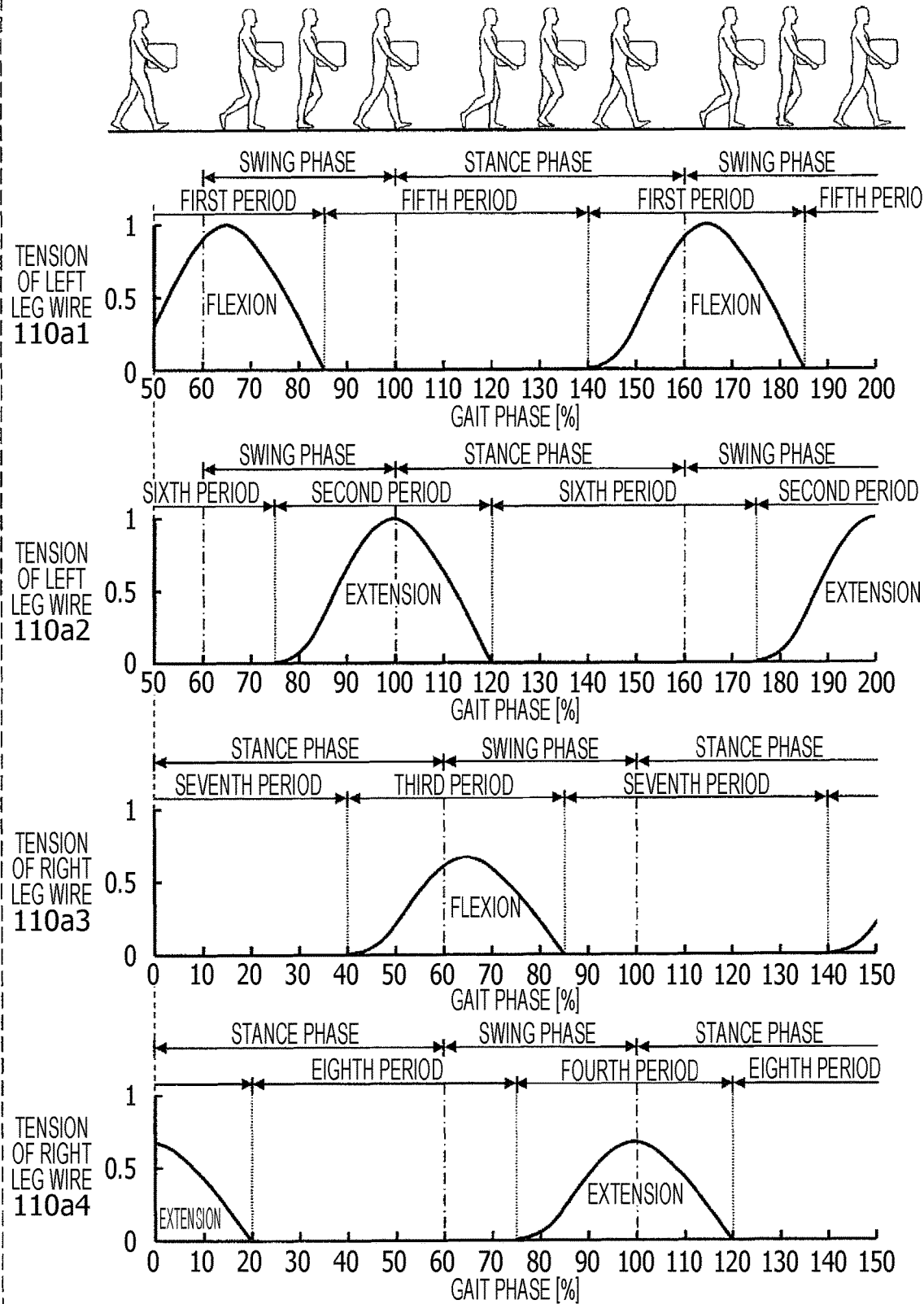
FIG. 28 is a diagram illustrating another example operation of the assistance apparatus according to the embodiment for assisting a user in walking forward while carrying an object in such a manner that the load applied to the left hand is larger than the load applied to the right hand.

In the example illustrated in FIG. 26C, the user 1 wearing the assistance apparatus 100 carries an object A only using the left hand. In this case, the load applied to the left hand of the user 1 is much larger than the load applied to the right hand of the user 1, and the center of gravity of the body of the user 1 shifts leftward from the center, resulting in an increase in the load on the left leg of the user 1. Thus, the drive control unit 122 controls the tensions of the wires 110a1 to 110a4 by using input profiles of wire tensions corresponding to a first ratio larger than that in the example illustrated in FIG. 26B. Such a first ratio is set to any value in the range of 1.2 or more and 3.0 or less. In the example illustrated in FIG. 26C, the first ratio is set to, for example, "1.5". In this case, the drive control unit 122 controls the tensions of the wires 110a1 to 110a4 in accordance with input profiles of wire tensions illustrated in FIG. 28. FIG. 28 is a diagram illustrating another example operation of the assistance apparatus 100 for assisting a user in walking forward while carrying an object in such a manner that the load applied to the left hand is larger than the load applied to the right hand. In the example illustrated in FIG. 28, the maximum tensions to be generated in the wires 110a1 and 110a2 of the left leg are 100 N, and the maximum tensions to be generated in the wires 110a3 and 110a4 of the right leg are 67 N. The waveforms of the input profiles of the tensions of the wires 110a3 and 110a4 are entirely changed in accordance with the reduced maximum tensions.

In the example illustrated in FIG. 28, the tension of the wire 110a1 in the first period, which is represented by $g1(\theta)$, the tension of the wire 110a2 in the second period, which is represented by $g2(\theta)$, the tension of the wire 110a3 in the third period, which is represented by $g3(\theta)$, and the tension of the wire 110a4 in the fourth period, which is represented by $g4(\theta)$, where $\theta$ denotes a gait phase, may be defined as follows: $g1(\theta)/g3(\theta)$=first ratio, $g2(\theta)/g4(\theta)$=first ratio, and first ratio=1.5. Note that the gait phase $\theta$ may not include a gait phase in which tension application is started. Note that the gait phase $\theta$ may not include a gait phase in which tension application is finished.

As described above, the assistance apparatus 100 determines the first ratio on the basis of the difference between the loads applied to the left and right hands of a user. Specifically, as the difference increases, the first ratio increases. Further, the assistance apparatus 100 changes the input profiles of wire tensions illustrated in FIG. 25, in which the first ratio is equal to 1, by making the wire tensions of the left and right legs different from each other in accordance with the first ratio, and controls the tensions of the wires 110a1 to 110a4 in accordance with the changed input profiles. That is, the assistance apparatus 100 changes the balance between the wire tension of the left leg and the wire tension of the right leg on the basis of the difference between the loads applied to the left and right hands of the user. The difference between the loads applied to the left and right hands may be represented as the discrepancy between the loads applied to the left and right hands, the ratio of the loads applied to the left and right hands, or the like. The changed input profiles may be stored in the storage unit 125 in advance or may be calculated by the drive control unit 122. Further, as described with reference to FIG. 24, even if the manner in which a user carries an object is changed between, for example, the examples illustrated in FIG. 26A to FIG. 26C during walking, the assistance apparatus 100 can change the balance between the wire tensions of the left and right legs in accordance with the changed manner.

3-3-1. First Modification of Assistance Operation of Assistance Apparatus

A first modification of the assistance operation of the assistance apparatus 100 will be described. In this modification, the assistance apparatus 100 makes the wire tension to be generated in the wires 110a1 and 110a2 of the left leg different from the wire tension to be generated in the wires 110a3 and 110a4 of the right leg on the basis of information on the dominant hand of a user. The information on the dominant hand of a user is information indicating which of the left and right hands is the dominant hand of the user. The drive control unit 122 of the assistance apparatus 100 may acquire information on the dominant hand of the user, which is stored in the storage unit 125 in advance, or may acquire information on the dominant hand of the user, which is input via the input device 140 or the terminal device 150.

As illustrated in FIG. 8, when the input device 140 is used, the user presses the "left-handed" button 145 or the "right-handed" button 146 to determine the dominant hand. The drive control unit 122 receives a signal generated by the "left-handed" button 145 or the "right-handed" button 146 to acquire information indicating which of the left and right hands is the dominant hand. It may be possible to set a muscular difference between the dominant hand and the non-dominant hand. For example, in the input device 140, a muscular difference may be set in accordance with the number of times the "left-handed" button 145 or the "right-handed" button 146 is pressed. Specifically, for example, as the number of times the "left-handed" button 145 is pressed increases, the muscle strength of the left hand may be set to be higher than that of the right hand. The same applies to the "right-handed" button 146. The method for setting a muscular difference is not limited to that described above, and any method may be used. For example, a button, a dial, a slide button, a lever, or any other suitable device for setting a muscular difference may be disposed. The timing at which information on the dominant hand of a user is input may be, for example, any timing in a process during which the user performs an operation of determining that an operation mode is to be implemented.

A user is more likely to place a larger load on the dominant hand when carrying an object in both hands. Further, a user is more likely to carry an object in the dominant hand when carrying the object in one hand. Thus, the center of gravity of the body of a user who carries an object shifts toward the dominant hand, and the load on the leg on the same side as the dominant hand is larger. For example, when the dominant hand is the left hand, the load on the left leg is larger than that on the right leg. When the dominant hand is the right hand, the load on the right leg is larger than that on the left leg. Thus, the drive control unit 122 changes the input profiles of the wire tensions illustrated in FIG. 25 in such a manner that the tension of the wires 110 of the leg on the same side as the dominant hand is greater than the tension of the wires 110 of the leg on the side opposite to the dominant hand, and uses the changed input profiles. For example, when the left hand is the dominant hand, in the changed input profiles, the tensions to be generated in the wires 110a1 and 110a2 of the left leg are greater than the tensions to be generated in the wires 110a3 and 110a4 of the right leg.

Also in this modification, the relationship between the tension of the wires 110a1 and 110a2 of the left leg and the tension of the wires 110a3 and 110a4 of the right leg is defined on the basis of the tension ratio, as a non-limiting example. Alternatively, for example, the relationship may be defined on the basis of the tension difference. Specifically, a second ratio similar to the first ratio is used. When the dominant hand is the left hand, second ratio=(tension of wire of left leg)/(tension of wire of right leg) holds. The second ratio is set to any value in the range of 1.2 or more and 1.5 or less. The drive control unit 122 may use the second ratio, which is determined in advance, or may determine a second ratio on the basis of the muscular difference described above between the dominant hand and the non-dominant hand. In this case, as the muscular difference increases, the second ratio increases. For example, when the dominant hand is the left hand and the second ratio is "1.2", as in the case where there is a difference between the loads applied to the left and right hands, the drive control unit 122 controls the tensions of the wires 110 in accordance with the input profiles of the wire tensions illustrated in FIG. 27.

When the dominant hand is the left hand, the drive control unit 122 makes the tension of the wire 110a1 in the first period during the gait phase of the left leg and the tension of the wire 110a2 in the second period during the gait phase of the left leg greater than the tension of the wire 110a3 in the third period during the gait phase of the right leg and the tension of the wire 110a4 in the fourth period during the gait phase of the right leg. When the dominant hand is the right hand, the drive control unit 122 makes the tension of the wire 110a3 in the third period during the gait phase of the right leg and the tension of the wire 110a4 in the fourth period during the gait phase of the right leg greater than the tension of the wire 110a1 in the first period during the gait phase of the left leg and the tension of the wire 110a2 in the second period during the gait phase of the left leg.

Also in this modification, for example, when the dominant hand is the left hand, both the maximum tensions of the wires 110a1 and 110a2 of the left leg may be made larger than the maximum tensions of the wires 110a3 and 110a4 of the right leg, or only the maximum tension of the wire 110a2 of the left leg may be made larger than the maximum tensions of the wires 110a3 and 110a4 of the right leg.

As described above, the assistance apparatus 100 determines the second ratio on the basis of information on the dominant hand of a user. Further, the assistance apparatus 100 changes the input profiles of wire tensions illustrated in FIG. 25, in which the second ratio is equal to 1, by making the wire tensions of the left and right legs different from each other in accordance with the second ratio, and controls the tensions of the wires 110 in accordance with the changed input profiles. That is, the assistance apparatus 100 changes the balance between the wire tension of the left leg and the wire tension of the right leg on the basis of information on the dominant hand of the user. The changed input profiles may be stored in the storage unit 125 in advance or may be calculated by the drive control unit 122.

As in this modification, when changing the balance between the wire tensions of the left and right legs on the basis of information on the dominant hand of a user, the assistance apparatus 100 may or may not apply a change in the balance between the wire tensions of the left and right legs based on the difference between the loads applied to the left and right hands of the user. When the change in the balance is not applied, detection performed by the contact sensors 301a and 301b is no longer necessary. Thus, the assistance apparatus 100 can be simplified, and the process for controlling wire tensions can be simplified. When the change in the balance is applied, elaborate wire tension control that reflects the state of a user who carries an object and the characteristics of the user is feasible.

3-3-2. Second Modification of Assistance Operation of Assistance Apparatus

A second modification of the assistance operation of the assistance apparatus 100 will be described. In this modification, the assistance apparatus 100 detects that a user is carrying an object in one hand on the basis of the loads applied to the left and right hands. When a user carries an object in one hand, in the embodiment, the assistance apparatus 100 makes the tensions of the wires 110 of the leg on the same side as the hand carrying the object greater than the tensions of the wires 110 of the leg on the opposite side. In this modification, in contrast, the assistance apparatus 100 makes the tensions of a different combination of wires 110 from that in the embodiment greater than the tensions of the other wires 110.

First, among the operations of the assistance apparatus 100 according to this modification, an operation of detecting that a user is carrying an object in one hand on the basis of the loads applied to the left and right hands will be described. Referring to FIG. 3, FIG. 10A, and FIG. 10B, the grasp recognition unit 121 detects loads applied to the left contact sensor 301a and the right contact sensor 301b on the basis of sensor values acquired from the left contact sensor 301a and the right contact sensor 301b, and detects loads applied to the left and right hands of the user 1 accordingly.

A condition in which the load, or force, applied to the left contact sensor 301a is greater than or equal to a second threshold value and in which no load is applied to the right contact sensor 301b is represented as a first condition. A condition in which the load applied to the right contact sensor 301b is greater than or equal to the second threshold value and in which no load is applied to the left contact sensor 301a is represented as a second condition. When the first condition is satisfied, the drive control unit 122 detects that the user 1 is carrying an object only in the left hand. When the second condition is satisfied, the drive control unit 122 detects that the user 1 is carrying an object only in the right hand.

The second threshold value may be a value that allows a user to feel, when a load greater than or equal to the second threshold value is exerted on one hand, an increase in the load on the leg on the same side as the hand. The second threshold value may have a temporal meaning. For example, keeping a value greater than or equal to the second threshold value over a predetermined time period or longer may represent being a value greater than or equal to the second threshold value. The second threshold value may be set for each user. The second threshold value may be selected from within a range of voltage values 50 to 220, which is normalized with, for example, 0 to 255, and is, for example, 200. Further, the expression "no load being applied to the left contact sensor 301a and the right contact sensor 301b" is used to include not only a load of "0" but also a load smaller than a third threshold value. If a load greater than or equal to 0 and less than the third threshold value is applied to the left contact sensor 301a and the right contact sensor 301b, the drive control unit 122 regards no load as being applied to the left contact sensor 301a and the right contact sensor 301b. The third threshold value may be a value such as a voltage value normalized with 0 to 255. The third threshold value may be selected from within a range of 10 to 50, and is, for example, 20.

As described above, the drive control unit 122 detects whether the user 1 is carrying an object only in the left hand or the right hand, in accordance with whether the first condition or the second condition is satisfied. If the load applied to one of the left contact sensor 301*a* and the right contact sensor 301*b* is greater than or equal to the second threshold value and the load applied to the other contact sensor is greater than or equal to the third threshold value, the drive control unit 122 may detect that the user 1 is carrying an object in both hands.

Then, the operations of the assistance apparatus 100 when the first condition is satisfied and when the second condition is satisfied will be described. First, when the first condition is satisfied, the user 1 carries an object only in the left hand and the load imposed on the left leg is larger than that on the right leg. Thus, the drive control unit 122 uses input profiles of wire tensions obtained by changing the input profiles of the wire tensions illustrated in FIG. 25 in such a manner that the tensions of the wire 110*a*2 of the left leg and the wire 110*a*3 of the right leg are greater than the tensions of the wire 110*a*1 of the left leg and the wire 110*a*4 of the right leg. That is, the assistance apparatus 100 changes the balance of the tensions of the wires 110*a*1 to 110*a*4. Specifically, the maximum tension of the wire 110*a*2 in the second period during the gait phase of the left leg is made greater than the maximum tension of the wire 110*a*4 in the fourth period during the gait phase of the right leg. Further, the maximum tension of the wire 110*a*3 in the third period during the gait phase of the right leg is made greater than the maximum tension of the wire 110*a*1 in the first period during the gait phase of the left leg.

Accordingly, the drive control unit 122 makes the tension of the wire 110*a*2 in the second period during the gait phase of the left leg greater than the tension of the wire 110*a*4 in the fourth period during the gait phase of the right leg, and makes the tension of the wire 110*a*3 in the third period during the gait phase of the right leg greater than the tension of the wire 110*a*1 in the first period during the gait phase of the left leg. Thus, the assistance apparatus 100 makes the assistance force for extension of the left leg and the assistance force for flexion of the right leg greater than the assistance force for extension of the right leg and the assistance force for flexion of the left leg, respectively.

Further, the relationship between the wire tensions after the balance is changed is defined on the basis of a third ratio similar to the first ratio used in the embodiment, as a non-limiting example. Alternatively, for example, the relationship may be defined on the basis of the tension difference. In the case of the third ratio, third ratio=(tension of wire 110*a*2)/(tension of wire 110*a*4), and third ratio=(tension of wire 110*a*3)/(tension of wire 110*a*1) hold. The third ratio is set to any value in the range of 1.2 or more and 2.0 or less. The third ratio increases as the difference between the load applied to the left hand and the load applied to the right hand increases. However, the third ratio may be a fixed value. When the third ratio is a fixed value, the third ratio may be determined in advance and stored in the storage unit 125, or may be determined by the user 1 through the input device 140 or the terminal device 150 and stored in the storage unit 125. For example, in the input device 140 illustrated in FIG. 8, the "left-handed" button 145 and the "right-handed" button 146 may have a function of decreasing and increasing the third ratio.

Figure 29:
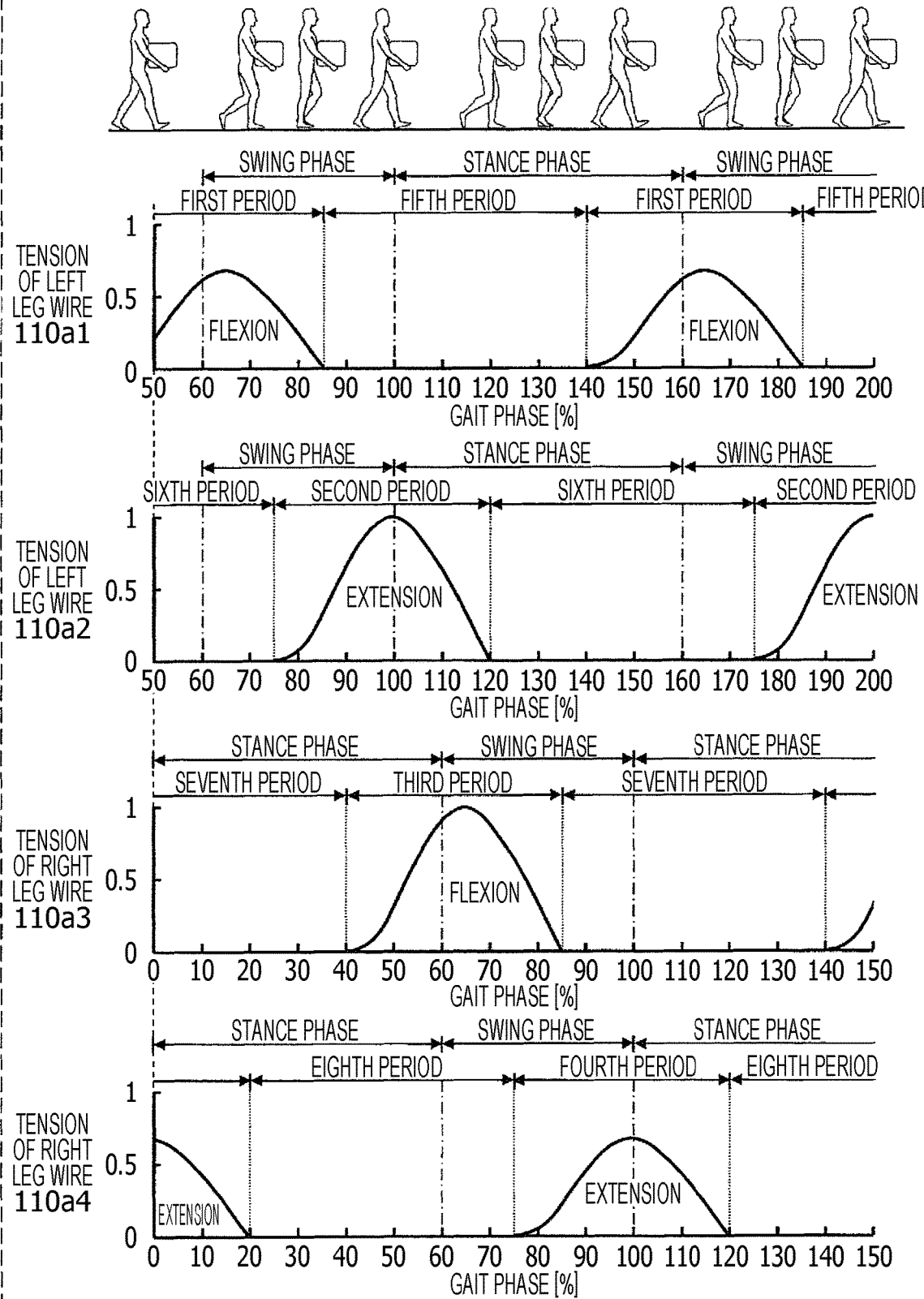
FIG. 29 is a diagram illustrating an example operation of the assistance apparatus according to the embodiment for assisting a user in walking forward while carrying an object only in the left hand.

When the first condition is satisfied, the drive control unit 122 controls the tensions of the wires 110 in accordance with input profiles of wire tensions illustrated in FIG. 29, which are obtained by changing the input profiles of the wire tensions illustrated in FIG. 25. FIG. 29 is a diagram illustrating an example operation of the assistance apparatus 100 for assisting a user in walking forward while carrying an object only in the left hand. In the example illustrated in FIG. 29, the third ratio is "1.5", the maximum tensions to be generated in the wire 110*a*2 and the wire 110*a*3 are 100 N, and the maximum tensions to be generated in the wire 110*a*4 and the wire 110*a*1 are 67 N. The waveforms of the input profiles of the tensions of the wires 110*a*1 and 110*a*4 are entirely changed in accordance with the reduced maximum tensions. In the example illustrated in FIG. 29, the tension generation timings, the tension generation periods, and the timings at which the tensions are maximum in the waveforms of the input profiles of the tensions of the wires 110*a*1 and 110*a*4 remain unchanged from those illustrated in FIG. 25.

In the example illustrated in FIG. 29, the tension of the wire 110*a*1 in the first period, which is represented by $h1(\theta)$, the tension of the wire 110*a*2 in the second period, which is represented by $h2(\theta)$, the tension of the wire 110*a*3 in the third period, which is represented by $h3(\theta)$, and the tension of the wire 110*a*4 in the fourth period, which is represented by $h4(\theta)$, where $\theta$ denotes a gait phase, may be defined as follows: $h2(\theta)/h4(\theta)$=third ratio, and $h3(\theta)/h1(\theta)$=third ratio. Note that the gait phase $\theta$ may not include a gait phase in which tension application is started. Note that the gait phase $\theta$ may not include a gait phase in which tension application is finished.

Then, when the second condition is satisfied, the user carries an object only in the right hand and the load imposed on the right leg is larger than that on the left leg. Thus, the drive control unit 122 uses input profiles of wire tensions obtained by changing the input profiles of the wire tensions illustrated in FIG. 25 in such a manner that the tensions of the wire 110*a*4 of the right leg and the wire 110*a*1 of the left leg are greater than the tensions of the wire 110*a*2 of the left leg and the wire 110*a*3 of the right leg. Specifically, the maximum tension of the wire 110*a*4 in the fourth period during the gait phase of the right leg is made greater than the maximum tension of the wire 110*a*2 in the second period during the gait phase of the left leg. Further, the maximum tension of the wire 110*a*1 in the first period during the gait phase of the left leg is made greater than the maximum tension of the wire 110*a*3 in the third period during the gait phase of the right leg.

Accordingly, the drive control unit 122 makes the tension of the wire 110*a*4 in the fourth period during the gait phase of the right leg greater than the tension of the wire 110*a*2 in the second period during the gait phase of the left leg, and makes the tension of the wire 110*a*1 in the first period during the gait phase of the left leg greater than the tension of the wire 110*a*3 in the third period during the gait phase of the right leg. Thus, the assistance apparatus 100 makes the assistance force for extension of the right leg and the assistance force for flexion of the left leg greater than the assistance force for extension of the left leg and the assistance force for flexion of the right leg, respectively. Accordingly, the assistance apparatus 100 provides assistance, which is similar to that for the left and right legs when the first condition is satisfied, to the right and left legs.

For the third ratio, third ratio=(tension of wire 110*a*4)/(tension of wire 110*a*2), and third ratio=(tension of wire 110*a*1)/(tension of wire 110*a*3) hold.

Figure 30:
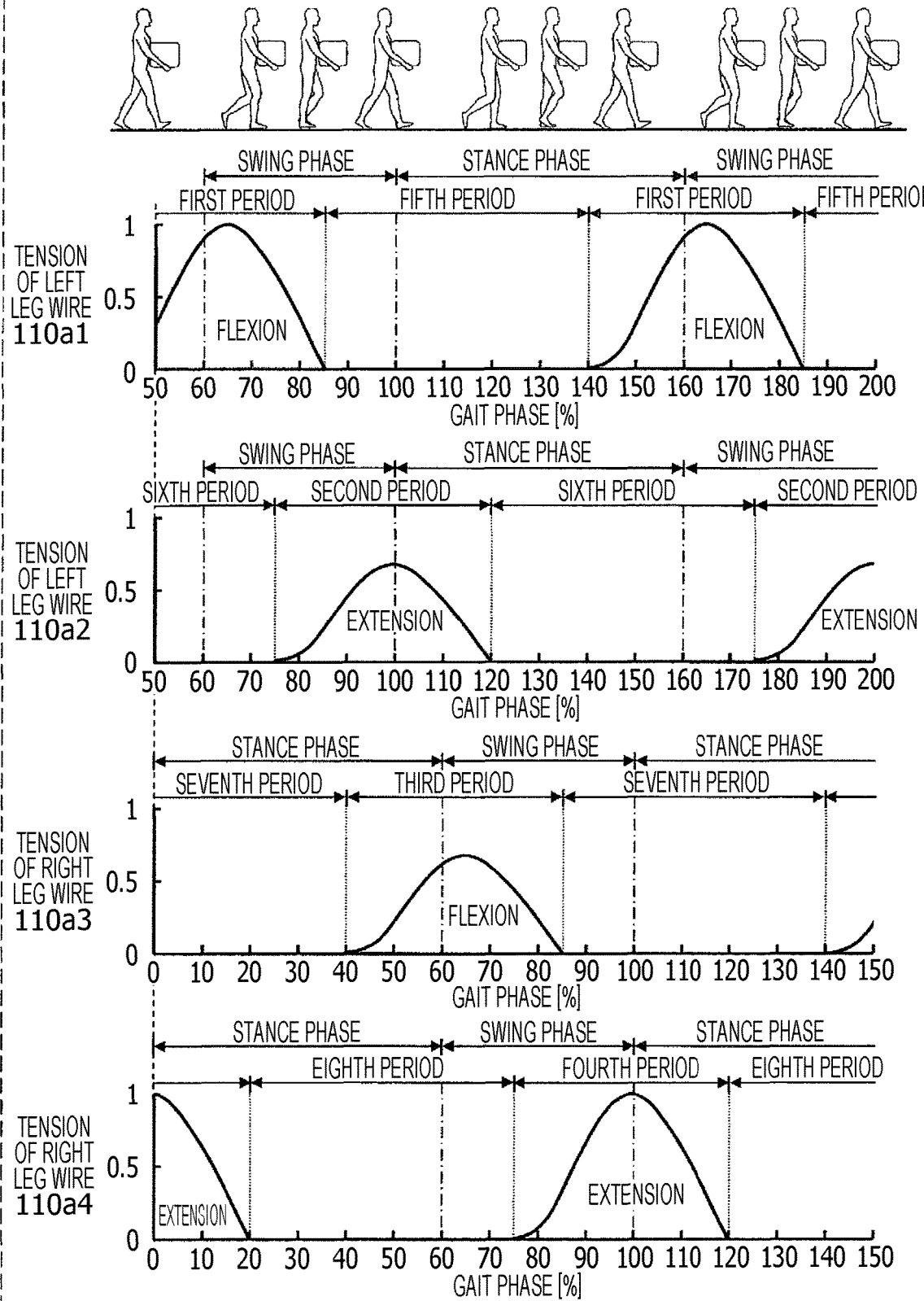
FIG. 30 is a diagram illustrating an example operation of the assistance apparatus according to the embodiment for assisting a user in walking forward while carrying an object only in the right hand.

When the second condition is satisfied, the drive control unit 122 controls the tension of the wires 110*a*1 to 110*a*4 in accordance with input profiles of wire tensions illustrated in FIG. 30, which are obtained by changing the input profiles of the wire tensions illustrated in FIG. 25. FIG. 30 is a diagram illustrating an example operation of the assistance apparatus 100 for assisting a user in walking forward while carrying an object only in the right hand. In the example illustrated in FIG. 30, the third ratio is "1.5", the maximum tensions to be generated in the wire 110a4 and the wire 110a1 are 100 N, and the maximum tensions to be generated in the wire 110a2 and the wire 110a3 are 67 N. The input profiles of the tensions of the wires 110a2 and 110a3 are configured using a method similar to that for the wires 110a1 and 110a4 illustrated in FIG. 29.

In the example illustrated in FIG. 30, the tension of the wire 110a1 in the first period, which is represented by i1(θ), the tension of the wire 110a2 in the second period, which is represented by i2(θ), the tension of the wire 110a3 in the third period, which is represented by i3(θ), and the tension of the wire 110a4 in the fourth period, which is represented by i4(θ), where θ denotes a gait phase, may be defined as follows: i4(θ)/i2(θ)=third ratio, and i1(θ)/i3(θ)=third ratio. Note that the gait phase θ may not include a gait phase in which tension application is started. Note that the gait phase θ may not include a gait phase in which tension application is finished.

The input profiles of the wire tensions illustrated in FIG. 29 and FIG. 30 may be created in advance and stored in the storage unit 125, or may be configured by the drive control unit 122.

The assistance apparatus 100, described above, applies a larger assistance force for extension to the left leg, which bears a larger gravitationally downward load due to an object being carried in the left hand, than that for the right leg, which bears a smaller load, and applies a larger assistance force for extension to the right leg, which bears a larger gravitationally downward load due to an object being carried in the right hand, than that for the left leg, which bears a smaller load. The assistance force for extension supports a leg bearing a gravitationally downward load and reduces the burden on the leg. Accordingly, the assistance apparatus 100 assists a user in walking with a burden and fatigue of the left and right legs being made uniform and reduced. This enables the user to walk by moving the left and right legs in a well-balanced manner while feeling uniform loads being imposed on the left and right legs. Further, the assistance apparatus 100 applies a larger assistance force for flexion to the right leg, which bears a smaller load, than that for the left leg, which bears a larger load, and applies a larger assistance force for flexion to the left leg, which bears a smaller load, than that for the right leg, which bears a larger load. Thus, the assistance apparatus 100 facilitates and induces the progress of the user's walking. Further, the assistance apparatus 100 applies a larger assistance force to both the left and right legs, rather than to either leg, to provide well-balanced assistance to the left and right legs.

When a user walking while carrying an object in the left or right hand stops walking, the assistance apparatus 100 may change assistance provided to the user. In this case, the drive control unit 122 detects that the user has stopped walking by using a sensor value of the pressure-sensitive sensor 302 or the inertial measurement unit 303, and further identifies a leg bearing a larger load. Then, the drive control unit 122 changes tension control for the wires 110a1 to 110a4 on the basis of the identified result.

When the pressure-sensitive sensor 302 is used, the drive control unit 122 acquires the sensor value of the pressure-sensitive sensor 302 on the left foot and the sensor value of the pressure-sensitive sensor 302 on the right foot. A voltage value, which is a sensor value of the pressure-sensitive sensor 302, corresponds to a pressure sensor value and represents a foot-to-ground contact load. For example, a smaller voltage value of the pressure-sensitive sensor 302 represents a larger foot-to-ground contact load. The drive control unit 122 detects a left-foot-to-ground contact load and a right-foot-to-ground contact load from the voltage value of the pressure-sensitive sensor 302 on the left foot and the voltage value of the pressure-sensitive sensor 302 on the right foot, respectively, and detects the respective degrees of load on the left and right legs. Further, when voltage values indicating the ground contact of the left foot and the right foot are simultaneously acquired from the pressure-sensitive sensors 302 on the left and right feet, the drive control unit 122 determines that the user has stopped walking.

When the inertial measurement unit 303 is used, the drive control unit 122 acquires a sensor value from the acceleration sensor of the inertial measurement unit 303. The sensor value of the acceleration sensor corresponds to acceleration. The drive control unit 122 detects the acceleration of the user in the left-right direction from the sensor value of the acceleration sensor, and can thus detect the direction in which the center of gravity of the body of the user shifts from the neutral position. Further, the drive control unit 122 acquires a sensor value from the gyro sensor of the inertial measurement unit 303. Since the inertial measurement unit 303 is placed on the upper half of the body of the user, the sensor value of the inertial measurement unit 303 corresponds to the angular velocity of the upper half of the body. The drive control unit 122 can detect the amount by which the upper half of the body of the user is inclined forward, backward, or sideways and the amount by which the upper half of the body of the user is rotated sideways from the sensor value of the gyro sensor. Then, the drive control unit 122 identifies a leg bearing a larger load from the direction in which the center of gravity of the body shifts in the left-right direction, the amount by which the upper half of the body is inclined forward, backward, or sideways, and the amount by which the upper half of the body is rotated sideways. When the sensor value of the acceleration sensor indicates that the acceleration in the anterior-posterior direction is 0, the drive control unit 122 determines that the user has stopped walking.

After identifying a leg bearing a larger load, the drive control unit 122 continuously generates a tension in the wire 110a2 for assisting extension of the left leg, continuously generates a tension in the wire 110a4 for assisting extension of the right leg, generates no tension in the wire 110a1 for assisting flexion of the left leg, and generates no tension in the wire 110a3 for assisting flexion of the right leg. The tension of the wire 110a2 supports the left leg, which gives support to the body when the user is at rest in the upright position, and the tension of the wire 110a4 supports the right leg, which gives support to the body when the user is at rest in the upright position. At this time, if the leg bearing a larger load is the left leg, the drive control unit 122 makes the tension to be generated in the wire 110a2 greater than the tension to be generated in the wire 110a4 of the right leg, which bears a smaller load. If the leg bearing a larger load is the right leg, the drive control unit 122 makes the tension to be generated in the wire 110a4 greater than the tension to be generated in the wire 110a2 of the left leg, which bears a smaller load.

If the leg bearing a larger load is the left leg, the first ratio is applied to (tension to be generated in wire 110a2)/(tension to be generated in wire 110a4). If the leg bearing a larger load is the right leg, the first ratio is applied to (tension to be generated in wire 110a4)/(tension to be generated in wire 110a2).

Further, the tension to be generated in the wire 110a2 of a leg bearing a larger load when the user remains at rest is made less than the tension to be generated in the wire 110a2 of a leg bearing a larger load during walking. The tension to be generated in the wire 110a4 of a leg bearing a larger load when the user remains at rest is made less than the tension to be generated in the wire 110a4 of a leg bearing a larger load during walking.

In addition, when the load applied to the contact sensor 301a or 301b of a hand carrying an object becomes zero, the drive control unit 122 stops the operation of the assistance apparatus 100. That is, when the user releases the object, the drive control unit 122 stops the operation of the assistance apparatus 100.

Figure 31:
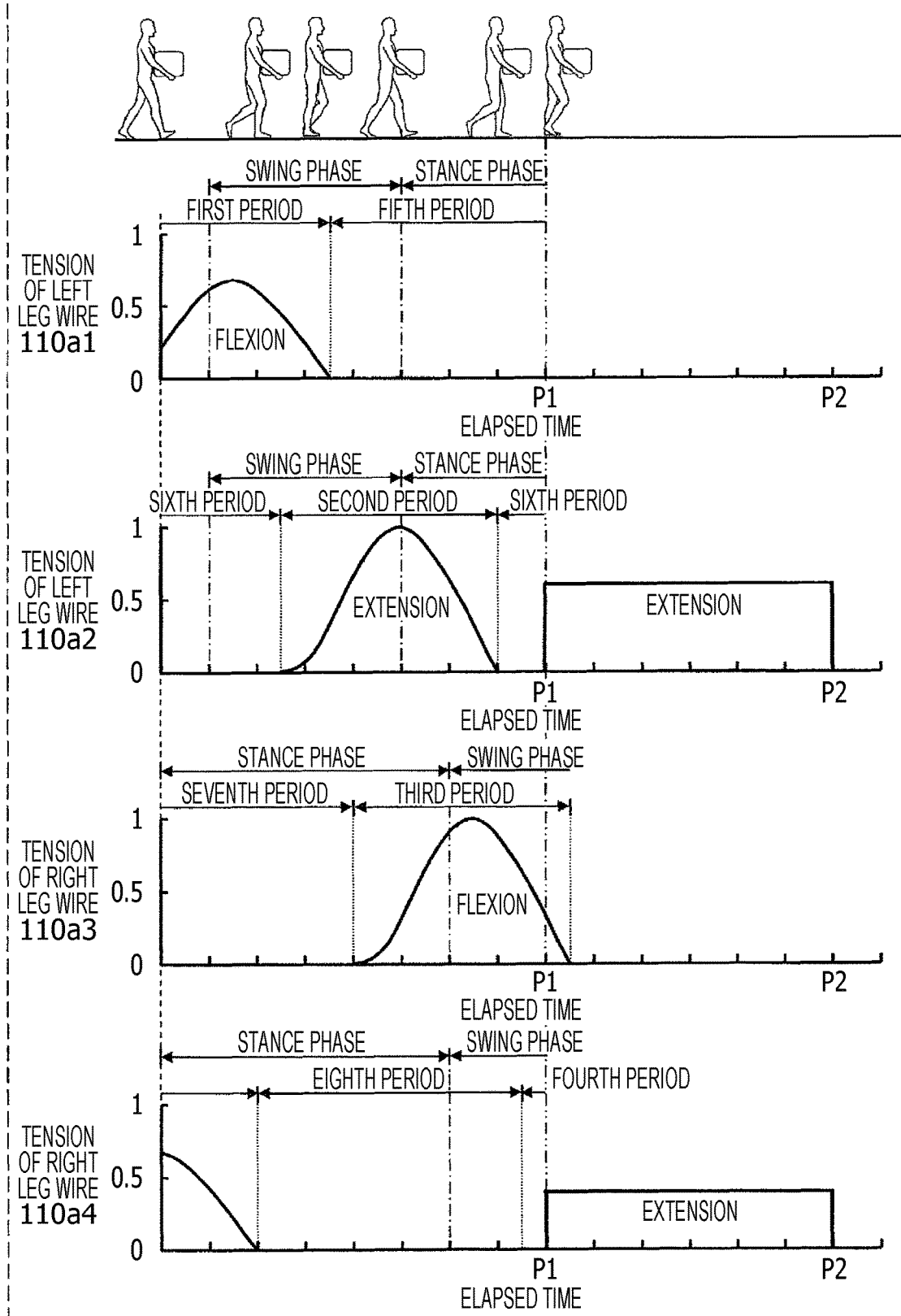
FIG. 31 is a diagram illustrating an example operation of the assistance apparatus according to the embodiment over a period in which a user carrying an object only in the left hand stops walking and releases the object.

For example, FIG. 31 illustrates an example operation of the assistance apparatus 100 over a period in which a user carrying an object only in the left hand stops walking and releases the object. As illustrated in FIG. 31, the user stops walking at time point P1 and releases the object from the left hand at time point P2. The assistance apparatus 100 generates a tension of 60 N in the wire 110a2 and a tension of 40 N in the wire 110a4 during the entirety of a period from the time point P1 to the time point P2. In the illustrated example, the first ratio is "1.5". Then, at the time point P2, the assistance apparatus 100 stops its operation. If there is a wire in which a tension is being generated at the time point P1, but in which no tension needs to be generated after the time point P1, such as the wire 110a3, the assistance apparatus 100 may stop generating a tension in the wire at the time point P1 or may continuously generate a tension in the wire after the time point P1 and stop generating a tension in the wire at a predetermined timing in accordance with the input profile. In the case of the wire 110a3, the predetermined timing is a timing at which the third period in the gait phase of the right leg ends.

As in this modification, when changing the balance between the wire tensions of the left and right legs in accordance with whether the first condition is satisfied and whether the second condition is satisfied, the assistance apparatus 100 may or may not apply a change in the balance between the wire tensions of the left and right legs in the embodiment and/or the first modification. When a change in the balance is applied, the assistance apparatus 100 can assist a user in walking while carrying an object in one hand and in walking while carrying an object in both hands.

3-3-3. Third Modification of Assistance Operation of Assistance Apparatus

A third modification of the assistance operation of the assistance apparatus 100 will be described. In the second modification, the assistance apparatus 100 identifies a hand in which a user carries an object on the basis of the first condition and the second condition. In this modification, a hand in which a user carries an object is designated by the user via input to the input device 140 or the terminal device 150.

Referring to FIG. 3 and FIG. 8, when the input device 140 is used, the user presses the "left-handed" button 145 or the "right-handed" button 146 to determine a hand carrying an object. Upon receipt of a signal generated by the "left-handed" button 145 or the "right-handed" button 146, the drive control unit 122 determines which of the left hand and the right hand as a hand carrying an object. When the determined hand is the left hand, the drive control unit 122 operates in a way similar to that when the first condition is satisfied in the second modification. When the determined hand is the right hand, the drive control unit 122 operates in a way similar to that when the second condition is satisfied in the second modification. Accordingly, the assistance apparatus 100 assists the user in walking while carrying an object in one hand in a way similar to that in the second modification without requiring the detection results of the contact sensors 301a and 301b. When the user stops walking, the drive control unit 122 may operate in a way similar to that in the second modification.

As in this modification, when changing the balance between the wire tensions of the left and right legs on the basis of information designating a hand that carries an object, the assistance apparatus 100 may or may not apply a change in the balance between the wire tensions of the left and right legs in the embodiment, the first modification, and/or the second modification. When a change in the balance is applied, the assistance apparatus 100 can assist a user in walking while carrying an object in one hand and can assist a user in walking while carrying an object in both hands. When a user carries an object in one hand, even if the user shifts the object from one hand to the other, the assistance apparatus 100 can assist the user in walking in accordance with the shift.

3-3-4. Fourth Modification of Assistance Operation of Assistance Apparatus

Figure 32:
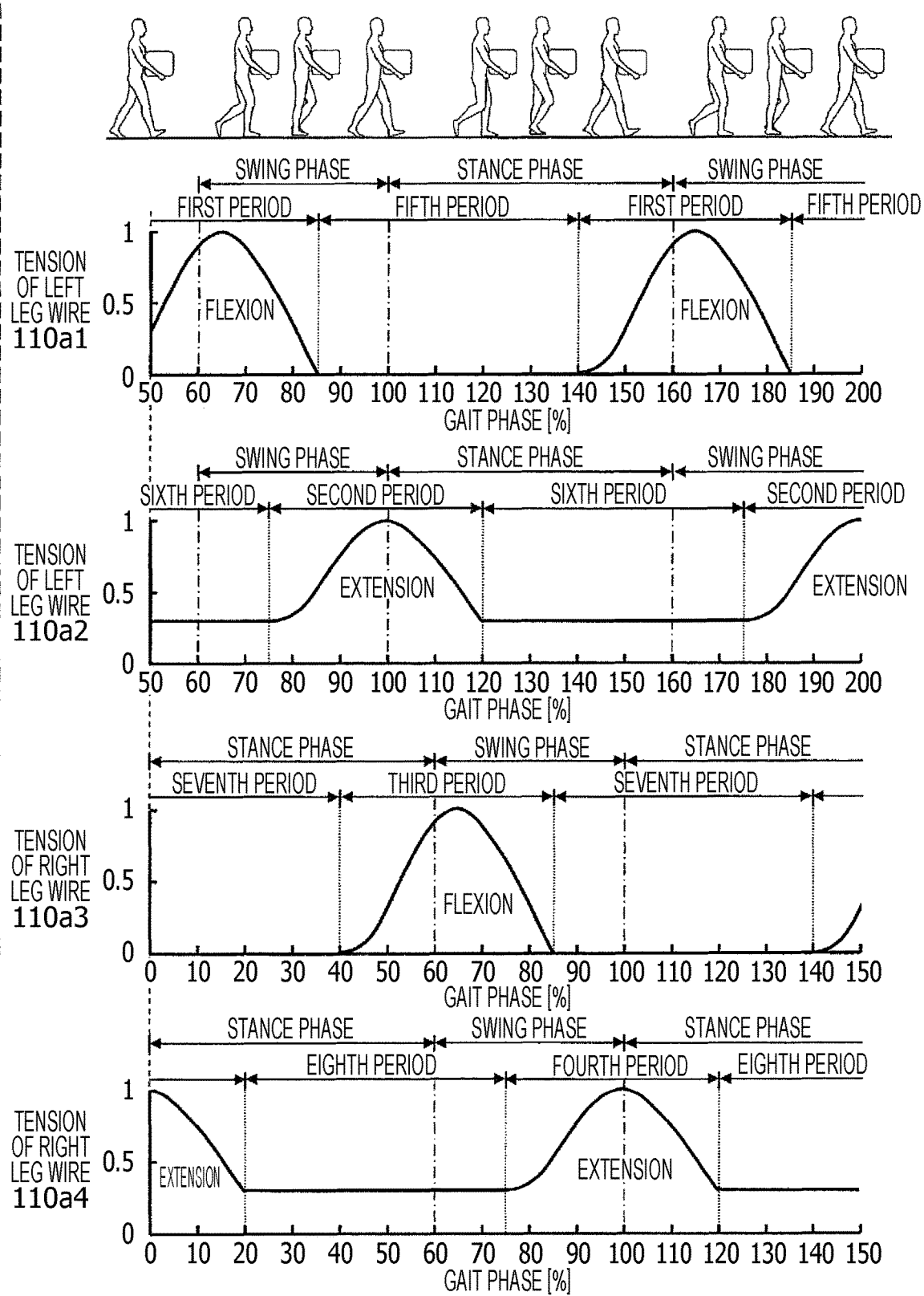
FIG. 32 is a diagram illustrating a modification of the operation of the assistance apparatus according to the embodiment for assisting a user in walking forward while carrying an object.

A fourth modification of the assistance operation of the assistance apparatus 100 will be described. In this modification, when assisting a user in walking while carrying an object, the assistance apparatus 100 operates in the following way. Specifically, the assistance apparatus 100 increases the duration of assistance using the wires 110a2 and 110a4 in the back part of the body of the user, compared with that in the example illustrated in FIG. 25. For example, FIG. 32 illustrates a modification of the operation of the assistance apparatus 100 for assisting a user in walking forward while carrying an object. FIG. 32 illustrates an example in which the assistance apparatus 100 assists both flexion and extension of the left and right legs of the user. The assistance apparatus 100 produces a wire tension while changing the wire tension, with a maximum tension being 100 N.

When assisting flexion of a user during forward walking, the assistance apparatus 100 generates wire tensions in the wire 110a1 of the left leg and the wire 110a3 of the right leg in a way similar to that in the example illustrated in FIG. 25.

When assisting extension of the left leg, for example, the assistance apparatus 100 continuously generates a tension in the wire 110a2 during the entirety of a second period, which is a period of 75% or more and 120% or less of the gait phase of the left leg. Then, the assistance apparatus 100 generates a wire tension greater than or equal to the first threshold value in the wire 110a2 during at least a portion of the second period. Then, the assistance apparatus 100 continuously generates a tension greater than or equal to the fourth threshold value and less than or equal to a fifth threshold value in the wire 110a2 during the entirety of a sixth period, which is a period other than the second period in the gait phase of the left leg. The tension of the wire 110a2 in the sixth period is greater than the tension of the wire 110a1 in the fifth period other than the first period in the gait phase of the left leg and is greater than the tension of the wire 110a2 in the sixth period in the example illustrated in FIG. 25. Further, the assistance apparatus 100 continuously generates a tension, which is greater than the wire tension in the sixth period, in the wire 110a2 during the entirety of the second period. Thus, during an entire period including the second period and the sixth period, the assistance apparatus 100 continuously generates a tension greater than or equal to the fourth threshold value in the wire 110a2. The fifth threshold value is a value less than the maximum wire tension. The fifth threshold value is, for example, a value given by an expression of maximum tension×0.6.

When assisting extension of the right leg, for example, the assistance apparatus 100 continuously generates a tension in the wire 110a4 during the entirety of a fourth period, which is a period of 75% or more and 120% or less of the gait phase of the right leg. Then, the assistance apparatus 100 generates a wire tension greater than or equal to the first threshold value in the wire 110a4 during at least a portion of the fourth period. Then, the assistance apparatus 100 continuously generates a tension greater than or equal to the fourth threshold value and less than or equal to the fifth threshold value in the wire 110a4 during the entirety of an eighth period, which is a period other than the fourth period. The tension of the wire 110a4 in the eighth period is greater than the tension of the wire 110a3 in the seventh period and is greater than the tension of the wire 110a4 in the eighth period in the example illustrated in FIG. 25. Further, the assistance apparatus 100 continuously generates a tension, which is greater than the wire tension in the eighth period, in the wire 110a4 during the entirety of the fourth period. Thus, during an entire period including the fourth period and the eighth period, the assistance apparatus 100 continuously generates a tension greater than or equal to the fourth threshold value in the wire 110a4.

As described above, a tension greater than or equal to the fourth threshold value is generated in the wires 110a2 and 110a4, which are located on or above the back part of the body of the user, during the entirety of a period over which the assistance apparatus 100 provides assistance. Thus, the user is subjected to the action such that the left and right legs are pulled backward all the time during walking. When the user is holding an object in the front part of the body, the center of gravity of the body of the user tends to be moved forward. Thus, the user, who is holding an object in the front part of the body, is subjected to the action such that the tensions of the wires 110a2 and 110a4 cause the user to walk forward with the center of gravity of the body being kept at the center of gravity position in the upright posture. This enables the user to walk with a stable posture. Accordingly, the user is able to transport an object with comfort. In the fifth period, the tension of the wire 110a1 for assisting flexion of the left leg is small, and thus the action exerted by the tension of the wire 110a2 is achieved while being less affected by the tension of the wire 110a1. In the seventh period, the tension of the wire 110a3 for assisting flexion of the right leg is small, and thus the action exerted by the tension of the wire 110a4 is achieved while being less affected by the tension of the wire 110a3.

The assistance apparatus 100 may perform an operation according to this modification so as to prevent a user from stumbling. By preventing a user from stumbling, the assistance apparatus 100 can prevent the user from falling. In this case, for example, the assistance apparatus 100 generates substantially no wire tension, that is, generates a wire tension less than the fourth threshold value, in the wire 110a2 for assisting extension of the left leg during a portion of the sixth period corresponding to the swing phase of the left leg within the gait phase of the left leg. The portion of the sixth period described above is, for example, a period of more than 60% and less than 75% of the gait phase of the left leg. Likewise, the assistance apparatus 100 makes the tension of the wire 110a4 for assisting extension of the right leg less than the fourth threshold value over a portion of the eighth period corresponding to the swing phase of the right leg within the gait phase of the right leg. The portion of the eighth period described above is, for example, a period of more than 60% and less than 75% of the gait phase of the right leg. This enables the user to easily raise a leg off the ground and prevents the user from dragging the toe across the ground, level differences, or the like when raising the leg.

In addition, for example, the assistance apparatus 100 continuously generates a wire tension greater than or equal to the fourth threshold value and less than or equal to the fifth threshold value in the wire 110a1 for assisting flexion of the left leg during the entirety of the fifth period in the gait phase of the left leg. The tension of the wire 110a1 in the fifth period is greater than the tension of the wire 110a1 in the fifth period in the example illustrated in FIG. 25. This enables the user to easily raise the left leg in the shift to flexion in the first period. In addition, the assistance apparatus 100 continuously generates a wire tension greater than or equal to the fourth threshold value and less than or equal to the fifth threshold value in the wire 110a3 for assisting flexion of the right leg during the entirety of the seventh period in the gait phase of the right leg. The tension of the wire 110a3 in the seventh period is greater than the tension of the wire 110a3 in the seventh period in the example illustrated in FIG. 25. This enables the user to easily raise the right leg in the shift to flexion in the third period. Thus, the assistance apparatus 100 enables the user to easily raise a leg during flexion and can prevent the user from dragging the toe and stumbling.

Also in the wire tension control described above, the assistance apparatus 100 may determine the first ratio on the basis of the difference between the loads applied to the left and right hands of the user and change the balance between the wire tensions of the left and right legs on the basis of the first ratio. Further, the assistance apparatus 100 may determine the second ratio on the basis of information on the dominant hand of the user and change the balance between the wire tensions of the left and right legs on the basis of the second ratio. Further, the assistance apparatus 100 may determine the third ratio on the basis of the first condition and the second condition and change the balance between the wire tensions of the left and right legs on the basis of the third ratio. Further, the assistance apparatus 100 may determine the third ratio on the basis of information designating a hand that carries an object and change the balance between the wire tensions of the left and right legs on the basis of the third ratio. In the cases described above, the assistance apparatus 100 may change, for the wires 110a2 and 110a4 in the back part of the body of the user, the wire tension in the entirety of the gait phase of the left leg and the wire tension in the entirety of the gait phase of the right leg to change the balance or may change, for the wires 110a2 and 110a4 in the back part of the body of the user, the wire tension in a portion of the gait phase of the left leg and the wire tension in a portion of the gait phase of the right leg to change the balance. For example, in the latter case, the wire tension in the second period during the gait phase of the left leg and the wire tension in the fourth period during the gait phase of the right leg may be changed, and the wire tension in the sixth period during the gait phase of the left leg and the wire tension in the eighth period during the gait phase of the right leg may be changed.

3-3-5. Other Modifications of Assistance Operation of Assistance Apparatus

The assistance apparatus 100 may not only assist a user in walking forward while carrying an object but also assist a stationary user in lifting an object. In this case, the assistance apparatus 100 does not assist flexion but assists extension of the left and right legs. When lifting an object in front of the user, the user shifts from a stooping or crouching position to an upright position. The user, who receives an assistance force for extension of both legs from the assistance apparatus 100, can more easily achieve the shift from the stooping or crouching position to the upright position.

During assistance, the assistance apparatus 100 generates a tension greater than a sixth threshold value in the wires 110a2 and 110a4 at the same timing. The sixth threshold value is a value larger than the first threshold value and the fourth threshold value. The sixth threshold value is, for example, 60 N. The tensions of the wires 110a2 and 110a4 for assisting the user in lifting an object may be greater than the tensions of the wires 110a2 and 110a4 for assisting a user in walking forward while carrying an object. The tensions of the wires 110a2 and 110a4 may be generated at timings that are shifted with respect to each other. The term "same timing" is used to include not only exactly the same timing but also different timings or timings with a difference. The assistance apparatus 100 having the configuration described above can assist a user in performing a series of motions from lifting an object to transporting the object.

Also when assisting in lifting an object, the assistance apparatus 100 may determine the first ratio on the basis of the difference between the loads applied to the left and right hands of the user and change the balance between the tension of the second wire 110a2 of the left leg and the tension of the fourth wire 110a4 of the right leg on the basis of the first ratio. Further, the assistance apparatus 100 may determine the second ratio on the basis of information on the dominant hand of the user and change the balance between the tensions of the wires 110a2 and 110a4 on the basis of the second ratio. Further, the assistance apparatus 100 may determine the third ratio on the basis of the first condition and the second condition and change the balance between the tensions of the wires 110a2 and 110a4 on the basis of the third ratio. Further, the assistance apparatus 100 may determine the third ratio on the basis of information designating a hand that carries an object and change the balance between the tensions of the wires 110a2 and 110a4 on the basis of the third ratio.

In the operation of the assistance apparatuses 100 and 200 according to the embodiment and modification, the control unit 120 identifies a leg bearing a larger load and a leg having a smaller load on the basis of the difference between the loads applied to the left and right hands of the user, which are detected via the contact sensors 301a and 301b, information on the dominant hand of the user, and/or information designating a hand that carries an object and changes the balance between the tensions of the wires. The method for identifying a leg bearing a larger load among the left and right legs is not limited to that described above. The drive control unit 122 may identify a leg bearing a larger load by using a sensor value of the pressure-sensitive sensor 302 or the inertial measurement unit 303. In this case, the drive control unit 122 may identify a leg bearing a larger load in the way described in the second modification.

In the respective operations of the assistance apparatuses 100 and 200 according to the embodiment and the modification, the same input profile of wire tension and the same maximum wire tension are set for all the wires 110 for assisting flexion and extension. However, the present disclosure is not limited to the embodiment and the modification described above. Since the moment arms of the hip joints and the lengths of the legs differ from one user to another, the assistance torque exerted on the hip joint differs depending on the user even when the same tension is applied to the same wire. The assistance torque is determined by an expression of wire tension×moment arm. Thus, different tensions may be applied to wires in accordance with the user. A fatter user has a larger moment arm of the hip joint than a thinner user. Thus, for example, the maximum wire tension may be set to 60 N for a fat user with a girth of 100 cm or more, whereas the maximum wire tension may be set to 120 N for a thin user with a girth or 70 cm or less. This may make assistance torques exerted on a fat user and a thin user equivalent.

In addition, the wire tension may change in accordance with the lengths of the legs of the user. In assistance for flexion and extension, since a vertical, or upward and downward, force component of wire tension is more largely exerted on a user with longer legs, the wire tension for a user with longer legs may be reduced. Adjusting the wire tension for each user in accordance with the body type and the leg length enables a comfortable assistance torque to be applied to each user.

In addition, the wire tensions on the front and back sides of the legs of the user are set to the same value. However, the present disclosure is not limited to the embodiment and the modification described above. For example, the tensions of the wires located on the front side of the legs may be greater than the tensions of the wires located on the back side of the legs. Since the wires on the back side pass through the buttocks of the user, the moment arm on the back side of the body of the user is greater than that on the front side of the body of the user. Accordingly, the assistance torque exerted on the hip joints on the back side of the body of the user is greater than that on the front side of the body of the user. Thus, by increasing the tension of the wires on the front side, the assistance apparatuses 100 and 200 can assist flexion and extension of the user on the front and back sides in a well-balanced manner.

The periods during which wire tensions are generated in the wires 110 for assistance for flexion and extension are equal to each other. However, the present disclosure is not limited to the embodiment and the modification described above. For example, in the example illustrated in FIG. 25, the period during which a wire tension for assisting flexion is generated and the period during which a wire tension for assisting extension of the same leg is generated overlap. To reduce the overlap period, the length of either of the periods may be reduced. In particular, the periods may be adjusted such that the period in which a wire tension greater than or equal to the first threshold value is generated during assistance for flexion does not overlap the period in which a wire tension greater than or equal to the first threshold value is generated during assistance for extension. This also applies to the examples illustrated in FIG. 27 to FIG. 32. This prevents the user from being confused by the simultaneous feeling of assistance for flexion and assistance for extension. The relationship between the period during which a wire tension for assisting flexion is generated and the period during which a wire tension for assisting extension is generated may be determined in accordance with the flexion and extension ability of the user.

In FIG. 25 and FIG. 27 to FIG. 32, the waveforms of the input profiles of wire tensions are convex curve. However, the present disclosure is not limited to the illustrated examples. The waveforms of the input profiles illustrated in FIG. 25 and FIG. 27 to FIG. 32 are waveforms obtained through experiments, which are waveforms that allow users to feel effective and comfortable when enjoying the benefits of assistance provided by the assistance apparatus 100. The input profiles of the wire tensions may be each created using, for example, a rectangular waveform, a trapezoidal waveform, a triangular waveform, a Gaussian waveform, or the like. When a rectangular waveform is used, the assistance apparatus 100 continuously generates a maximum tension during an entire period over which a wire tension is generated. When a trapezoidal waveform is used, the assistance apparatus 100 continuously generates a maximum tension during an entire period over which a wire tension is generated, except the initial and terminal periods. When each input profile is created using a waveform that is quadrangle such as a rectangular waveform and a trapezoidal waveform, a steep rise or a steep fall of the wire tension may occur. Such a change in tension may cause a user to feel uncomfortable during assistance. Thus, for example, when the waveform of each input profile is triangular, a rise of the wire tension to the maximum tension may be changed to a gentler one, with the wire tension changing gradually. Accordingly, the assistance apparatus 100 can carefully assist movements of the legs of the user, resulting in a reduction in the risk of falling of the user due to a steep change in wire tension.

In actual human walking, flexion and extension torques produced by the legs smoothly and continuously change. Thus, the waveform of each input profile may be implemented as a Gaussian waveform. The Gaussian waveform may be a waveform created by, for example, adding together, or superposing, Gaussian functions by using a Gaussian function given by Equation (1) below. In this case, among superposition methods of Gaussian functions, a superposition method that is closest to the waveform of a torque of the legs in actual human walking is found and applied to the generation of a waveform of an input profile. Finding such a method is also referred to as Gaussian fitting. Accordingly, assistance torques can be applied to realize walking similar to actual human walking, and more natural assistance can be achieved.

$$f(x) = \frac{1}{\sqrt{2\pi}\,\sigma} \exp\left\{-\frac{(x-\mu)^2}{2\sigma^2}\right\} \quad (1)$$

Specifically, a Gaussian function has a pair of variables $\mu$ and $\sigma$ (also referred to as parameters), and the waveform of the Gaussian function depends on the two parameters. The time indicating a peak of a wave of the Gaussian function depends on the variable $\mu$, and the width of the wave of the Gaussian function depends on the variable $\sigma$. Thus, various Gaussian functions may be generated by using various combinations of values of the two parameters.

A function obtained by multiplying an amplitude of a torque generated in a leg during human walking by a Gaussian function forms a waveform that shows time (in seconds) on the horizontal axis and torque (in Nm) on the vertical axis. Examples of the amplitude include a maximum torque of a leg during human walking, and the amplitude is, for example, 20 Nm. Gaussian functions are superposed to find a superposition method that is closest to the torque-time waveform of the leg during actual human walking. At this time, Gaussian fitting is performed on actual human gait data by using n Gaussian functions $f_1(x), f_2(x), \ldots,$ and $f_n(x)$ having various values of the two parameters $\mu$ and $\sigma$ to obtain Gaussian functions. The obtained Gaussian functions are further superposed to obtain a new Gaussian function. By adjusting the two parameters $\mu$ and $\sigma$ of the new Gaussian function, an input profile of a wire tension can be created.

Further, the assistance apparatus 100 may change the maximum tensions to be generated in the wires 110 in accordance with the time of year when the user wears the assistance apparatus 100. For example, in summer when the user wears light clothes, the user's moment arm is shorter than that in winter when the user wears thick clothes. Accordingly, even when the assistance apparatus 100 applies the same tension to the wires 110, the torques exerted on the legs of the user in summer are smaller than those in winter. Thus, for example, the assistance apparatus 100 may increase the tension to be applied to each of the wires 110 in summer to, for example, 1.2 times that in winter.

The operation of the assistance apparatus 200 according to the modification illustrated in FIG. 13 to FIG. 21 is also similar to that of the assistance apparatus 100 according to the embodiment. For the operations described above, the wire tension control for the first wire 110$a$1 and the wire tension control for the fifth wire 110$a$5 of the assistance apparatus 200 are similar to the wire tension control for the wire 110$a$1 of the assistance apparatus 100. The wire tension control for the second wire 110$a$2 and the wire tension control for the sixth wire 110$a$6 of the assistance apparatus 200 are similar to the wire tension control for the wire 110$a$2 of the assistance apparatus 100. The wire tension control for the third wire 110$a$3 and the wire tension control for the seventh wire 110$a$7 of the assistance apparatus 200 are similar to the wire tension control for the wire 110$a$3 of the assistance apparatus 100. The wire tension control for the fourth wire 110$a$4 and the wire tension control for the eighth wire 110$a$8 of the assistance apparatus 200 are similar to the wire tension control for the wire 110$a$4 of the assistance apparatus 100.

When assisting flexion or extension, the assistance apparatus 200 generates tensions in two wires of the same leg at the same timing. Thus, the maximum tension to be generated in the first wire 110$a$1 and the maximum tension to be generated in the fifth wire 110$a$5 of the assistance apparatus 200 may be different from the maximum tension to be generated in the wire 110$a$1 of the assistance apparatus 100 and may be smaller than the maximum tension to be generated in the wire 110$a$1 of the assistance apparatus 100, for example. The maximum tension to be generated in the second wire 110$a$2 and the maximum tension to be generated in the sixth wire 110$a$6 of the assistance apparatus 200 may be different from the maximum tension to be generated in the wire 110$a$2 of the assistance apparatus 100 and may be smaller than the maximum tension to be generated in the wire 110$a$2 of the assistance apparatus 100, for example. The maximum tension to be generated in the third wire 110$a$3 and the maximum tension to be generated in the seventh wire 110$a$7 of the assistance apparatus 200 may be different from the maximum tension to be generated in the wire 110$a$3 of the assistance apparatus 100 and may be smaller than the maximum tension to be generated in the wire 110$a$3 of the assistance apparatus 100, for example. The maximum tension to be generated in the fourth wire 110$a$4 and the maximum tension to be generated in the eighth wire 110$a$8 of the assistance apparatus 200 may be different from the maximum tension to be generated in the wire 110$a$4 of the assistance apparatus 100 and may be smaller than the maximum tension to be generated in the wire 110a4 of the assistance apparatus 100, for example.

The relationship between the maximum tension to be generated in the first wire 110a1 and the maximum tension to be generated in the fifth wire 110a5 of the assistance apparatus 200 and the maximum tension to be generated in the wire 110a1 of the assistance apparatus 100 changes in accordance with the angle between the direction in which the wire 110a1 of the assistance apparatus 100 extends and the direction in which the first wire 110a1 of the assistance apparatus 200 extends and in accordance with the angle between the direction in which the wire 110a1 of the assistance apparatus 100 extends and the direction in which the fifth wire 110a5 of the assistance apparatus 200 extends, and can be determined in accordance with the angles. The relationship between the maximum tension to be generated in the second wire 110a2 and the maximum tension to be generated in the sixth wire 110a6 of the assistance apparatus 200 and the maximum tension to be generated in the wire 110a2 of the assistance apparatus 100 changes in accordance with the angle between the direction in which the wire 110a2 of the assistance apparatus 100 extends and the direction in which the second wire 110a2 of the assistance apparatus 200 extends and in accordance with the angle between the direction in which the wire 110a2 of the assistance apparatus 100 extends and the direction in which the sixth wire 110a6 of the assistance apparatus 200 extends, and can be determined in accordance with the angles. The relationship between the maximum tension to be generated in the third wire 110a3 and the maximum tension to be generated in the seventh wire 110a7 of the assistance apparatus 200 and the maximum tension to be generated in the wire 110a3 of the assistance apparatus 100 changes in accordance with the angle between the direction in which the wire 110a3 of the assistance apparatus 100 extends and the direction in which the third wire 110a3 of the assistance apparatus 200 extends and in accordance with the angle between the direction in which the wire 110a3 of the assistance apparatus 100 extends and the direction in which the seventh wire 110a7 of the assistance apparatus 200 extends, and can be determined in accordance with the angles. The relationship between the maximum tension to be generated in the fourth wire 110a4 and the maximum tension to be generated in the eighth wire 110a8 of the assistance apparatus 200 and the maximum tension to be generated in the wire 110a4 of the assistance apparatus 100 changes in accordance with the angle between the direction in which the wire 110a4 of the assistance apparatus 100 extends and the direction in which the fourth wire 110a4 of the assistance apparatus 200 extends and in accordance with the angle between the direction in which the wire 110a4 of the assistance apparatus 100 extends and the direction in which the eighth wire 110a8 of the assistance apparatus 200 extends, and can be determined in accordance with the angles.

The term "same timing" is used to include not only exactly the same timing but also different timings or timings with a difference. The difference may be less than 10% or may be 5% or less in terms of the value of the gait phase. For example, when the difference is 5% or less, the values at all timings in the gait phase are included in a range of values of the gait phase, which is within ±5% from an average value of values at the timings in the gait phase.

4. Examples

An experiment was made for the assistance operation using the assistance apparatus 100 according to the embodiment to compare and verify the relationships between ways in which a user carries an object and the balance between the wire tensions of the left and right legs. Specifically, a method for carrying an object in Case 1 and a method for carrying an object in Case 2 were verified. In Case 1, as illustrated in FIG. 26B, a user carried an object in the left and right hands at different height positions. In Case 2, as illustrated in FIG. 26C, a user carried an object in one hand.

In Case 1, the operations of the assistance apparatus 100 in Example 1, Comparative Example 1, and Comparative Example 2 were verified. In Example 1, as in the embodiment, the assistance apparatus 100 operated in such a manner that the wire tension of the leg on the same side as the hand carrying the object at the lower position was set to be twice the wire tension of the leg on the same side as the hand carrying the object at the higher position. For example, in FIG. 26B, the wire tension of the left leg is set to be twice the wire tension of the right leg. In Example 1, the assistance apparatus 100 controlled the tensions of the wires 110 in accordance with input profiles similar to those illustrated in FIG. 28.

In Comparative Example 1, the assistance apparatus 100 operated with the balance between the wire tensions of the left and right legs opposite to that in Example 1. Specifically, the assistance apparatus 100 operated in such a manner that the wire tension of the leg on the same side as the hand carrying the object at the higher position was set to be twice the wire tension of the leg on the same side as the hand carrying the object at the lower position. In this case, the assistance apparatus 100 controlled the tensions of the wires 110 in accordance with input profiles in which the ratio of the wire tensions of the left and right legs in the input profiles of wire tensions used in Example 1 was reversed.

In Comparative Example 2, the assistance apparatus 100 operated in such a manner that the wire tension of the leg on the same side as the hand carrying the object at the lower position and the wire tension of the leg on the same side as the hand carrying the object at the higher position were equal. In this case, the assistance apparatus 100 controlled the tensions of the wires 110 in accordance with the input profiles illustrated in FIG. 25.

In Case 2, the operations of the assistance apparatus 100 in Example 2, Comparative Example 3, and Comparative Example 4 were verified. In Example 2, as in the second modification, the assistance apparatus 100 operated in such a manner that the wire tension for assisting extension of the leg on the same side as a hand carrying an object was set to be twice the wire tension for assisting extension of the leg on the same side as a hand not carrying the object and the wire tension for assisting flexion of the leg on the same side as the hand not carrying the object was set to be twice the wire tension for assisting flexion of the leg on the same side as the hand carrying the object. For example, in FIG. 26C, the wire tension for assisting extension of the left leg and flexion of the right leg is set to be twice the wire tension for assisting extension of the right leg and flexion of the left leg. In Example 2, the assistance apparatus 100 controlled the tensions of the wires 110 in accordance with input profiles similar to those illustrated in FIG. 29.

In Comparative Example 3, the assistance apparatus 100 operated with the balance between the wire tensions of the left and right legs opposite to that in Example 2. Specifically, the assistance apparatus 100 operated in such a manner that the wire tension for assisting extension of the leg on the same side as a hand not carrying an object was set to be twice the wire tension for assisting extension of the leg on the same side as a hand carrying the object and the wire tension for assisting flexion of the leg on the same side as the hand carrying the object was set to be twice the wire tension for assisting flexion of the leg on the same side as the hand not carrying the object. In this case, the assistance apparatus 100 controlled the tensions of the wires 110 in accordance with input profiles in which the wire tensions for assisting extension and flexion of the same leg in the input profiles of wire tensions used in Example 2 were reversed.

In Comparative Example 4, the assistance apparatus 100 operated in such a manner that the wire tension of the leg on the same side as a hand carrying an object and the wire tension of the leg on the same side as a hand not carrying the object were equal. In this case, the assistance apparatus 100 controlled the tensions of the wires 110 in accordance with the input profiles illustrated in FIG. 25.

In Examples 1 and 2 and Comparative Examples 1 to 4, the maximum tensions that could be generated in the wires 110$a$1 to 110$a$4 were each set to 100 N.

The experiment was conducted on four subjects, namely A to D. The subjects A, C, and D were males, and the subject B was female. All the subjects A to D wearing the assistance apparatus 100 received three types of assistance in Example 1, Comparative Example 1, and Comparative Example 2 when walking forward in Case 1, and received three types of assistance in Example 2, Comparative Example 3, and Comparative Example 4 when walking forward in Case 2. Then, the subjects A to D selected one optimum operation, which was the most comfortable walking operation, in each of Cases 1 and 2. The selection results are given in Table 1 below. Table 1 indicates that Examples 1 and 2 provide effective assistance for walking of a subject. Table 1 also indicates that Comparative Examples 2 and 4 also allow a subject to feel the effect of assistance.

TABLE 1

Evaluation results of assistance based on operations in patterns

| Subject | Case 1 | | | Case 2 | | |
|---|---|---|---|---|---|---|
| | Example 1 | Comparative Example 1 | Comparative Example 2 | Example 2 | Comparative Example 3 | Comparative Example 4 |
| A | Optimum | | | Optimum | | |
| B | Optimum | | | Optimum | | |
| C | Optimum | | | Optimum | | |
| D | | | Optimum | | | Optimum |

5. Other Embodiments

While an assistance apparatus and so on according to one or more aspects have been described in conjunction with an embodiment and a modification, the present disclosure is not limited to the embodiment and modification. Applications of various modifications conceived of by persons skilled in the art to this embodiment and modification and embodiments based on combinations of constituent elements in different embodiments and modifications may also be encompassed in the scope of one or more aspects as long as such applications or embodiments do not depart from the gist of the present disclosure.

For example, in the assistance apparatuses 100 and 200 according to the embodiment and modification, the timings at which the control unit 120 activates the motors 114 to generate tensions in the wires 110 and values of the gait phase regarding the input profiles of the tensions are not limited to the values described in the embodiment and modification. The timings and the values of the gait phase regarding the input profiles of the tensions may be different from those described in the embodiment and modification. For example, an error of several percent in terms of gait phase may occur.

In the assistance apparatuses 100 and 200 according to the embodiment and modification, each of the wires 110 is provided with a motor. However, the present disclosure is not limited to the embodiment and modification. One motor may be coupled to wires. For example, in the assistance apparatus 200, one motor may pull the wires 110$a$1 and 110$a$5. That is, the assistance apparatus 200 may include, for example, four motors so that one motor is provided for two wires.

In the assistance apparatuses 100 and 200 according to the embodiment and the modification, four wires or eight wires are used to couple the upper-body belt 111 to the knee belts 112$a$ and 112$b$. That is, two wires or four wires are coupled to each knee belt. However, the number of wires to be coupled to each knee belt is not limited to that described above. Any number of wires more than one may be coupled to each knee belt. For example, the numbers of wires to be coupled to the front part and the back part of each knee belt may be different. Flexion of the left leg may mean flexion of the hip joint of the left leg. Flexion of the right leg may mean flexion of the hip joint of the right leg. Extension of the left leg may mean extension of the hip joint of the left leg. Extension of the right leg may mean extension of the hip joint of the right leg.

The present disclosure is applicable to an apparatus for assisting a user in changing direction.

What is claimed is:

1. An assistance apparatus comprising:
an upper-body belt adapted to be worn on an upper half of a body of a user;
a left knee belt adapted to be worn on a left knee of the user;
a right knee belt adapted to be worn on a right knee of the user;
a first wire that couples the upper-body belt and the left knee belt to each other on or above a front part of the body of the user;
a second wire that couples the upper-body belt and the left knee belt to each other on or above a back part of the body of the user;
a third wire that couples the upper-body belt and the right knee belt to each other on or above the front part of the body of the user;
a fourth wire that couples the upper-body belt and the right knee belt to each other on or above the back part of the body of the user;
motors;
a left sensor attachable to a left hand of the user;
a right sensor attachable to a right hand of the user; and
a control circuit, wherein when the assistance apparatus assists the user in walking while carrying an object, the motors generate
- (i) a tension greater than or equal to a first threshold value in the first wire during a first period, the first period being a period of 35% or more and 90% or less of a gait phase of a left leg of the user,
- (ii) a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg,
- (iii) a tension greater than or equal to the first threshold value in the third wire during a third period, the third period being a period of 35% or more and 90% or less of a gait phase of a right leg of the user, and
- (iv) a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg, the control circuit acquires a left sensor value from the left sensor and a right sensor value from the right sensor, the control circuit detects a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value, when the first condition is detected, the motors make the tension of the second wire in the second period and the tension of the third wire in the third period greater than the tension of the first wire in the first period and the tension of the fourth wire in the fourth period, when the second condition is detected, the motors make the tension of the first wire in the first period and the tension of the fourth wire in the fourth period greater than the tension of the second wire in the second period and the tension of the third wire in the third period, and a walk timing detecting unit determines each percentage of the gait phase of the left leg and each percentage of the gait phase of the right leg based on information obtained using a sensor.

2. The assistance apparatus according to claim 1, wherein the left leg shifts from a stance phase to a swing phase during the first period, the left leg shifts from the swing phase to the stance phase during the second period, the right leg shifts from the stance phase to the swing phase during the third period, and the right leg shifts from the swing phase to the stance phase during the fourth period.

3. The assistance apparatus according to claim 1, wherein the motors include a first motor, a second motor, a third motor, and a fourth motor, the first wire has a first end fixed to the left knee belt,
the first wire has a second end fixed to the first motor,
the second wire has a first end fixed to the left knee belt,
the second wire has a second end fixed to the second motor,
the third wire has a first end fixed to the right knee belt,
the third wire has a second end fixed to the third motor,
the fourth wire has a first end fixed to the right knee belt, and
the fourth wire has a second end fixed to the fourth motor.

4. The assistance apparatus according to claim 1, further comprising:

a fifth wire that couples the upper-body belt and the left knee belt to each other and that extends on or above the front part of the body of the user in a direction crossing a direction in which the first wire extends;

a sixth wire that couples the upper-body belt and the left knee belt to each other and that extends on or above the back part of the body of the user in a direction crossing a direction in which the second wire extends;

a seventh wire that couples the upper-body belt and the right knee belt to each other and that extends on or above the front part of the body of the user in a direction crossing a direction in which the third wire extends; and an eighth wire that couples the upper-body belt and the right knee belt to each other and that extends on or above the back part of the body of the user in a direction crossing a direction in which the fourth wire extends, wherein when the assistance apparatus assists the user in walking while carrying the object, the motors generate
- (i) a tension greater than or equal to the first threshold value in the first wire and the fifth wire during the first period,
- (ii) a tension greater than or equal to the first threshold value in the second wire and the sixth wire during the second period,
- (iii) a tension greater than or equal to the first threshold value in the third wire and the seventh wire during the third period, and
- (iv) a tension greater than or equal to the first threshold value in the fourth wire and the eighth wire during the fourth period.

5. The assistance apparatus according to claim 1, wherein a time point of 50% of the gait phase of the left leg determined by the walk timing detecting unit based on the information obtained using the sensor corresponds to a time point of 0% of the gait phase of the right leg determined by the walk timing detecting unit, and a time point of 50% of the gait phase of the right leg determined by the walk timing detecting unit based on the information obtained using the sensor corresponds to a time point of 0% of the gait phase of the left leg determined by the walk timing detecting unit.

6. The assistance apparatus according to claim 1, further comprising a memory, wherein the memory stores a program for controlling the motors, and the control circuit controls the motors in accordance with the program.

7. The assistance apparatus according to claim 1, wherein the sensor is a gait sensor that detects a gait cycle of the user, and wherein the control circuit calculates the gait phase of the left leg and the gait phase of the right leg based on a sensor value of the gait sensor.

8. An assistance apparatus comprising:

an upper-body belt adapted to be worn on an upper half of a body of a user;

a left knee belt adapted to be worn on a left knee of the user;

a right knee belt adapted to be worn on a right knee of the user;
a first wire that couples the upper-body belt and the left knee belt to each other on or above a front part of the body of the user;
a second wire that couples the upper-body belt and the left knee belt to each other on or above a back part of the body of the user;
a third wire that couples the upper-body belt and the right knee belt to each other on or above the front part of the body of the user;
a fourth wire that couples the upper-body belt and the right knee belt to each other on or above the back part of the body of the user;
motors; and
a control circuit, wherein
when the assistance apparatus assists the user in walking while carrying an object,
the motors generate
 (i) a tension greater than or equal to a first threshold value in the first wire during a first period, the first period being a period of 35% or more and 90% or less of a gait phase of a left leg of the user,
 (ii) a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg,
 (iii) a tension greater than or equal to the first threshold value in the third wire during a third period, the third period being a period of 35% or more and 90% or less of a gait phase of a right leg of the user, and
 (iv) a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg,
the control circuit acquires information specifying a hand that carries the object from a memory or an interface device,
when the information indicates a left hand of the user, the motors make the tension of the second wire in the second period and the tension of the third wire in the third period greater than the tension of the first wire in the first period and the tension of the fourth wire in the fourth period, and
when the information indicates a right hand of the user, the motors make the tension of the first wire in the first period and the tension of the fourth wire in the fourth period greater than the tension of the second wire in the second period and the tension of the third wire in the third period, and
a walk timing detecting unit determines each percentage of the gait phase of the left leg and each percentage of the gait phase of the right leg based on information obtained using a sensor.

9. An assistance method for assisting a movement of a user by using wires attached to a body of the user, the assistance method comprising:
coupling, using a first wire among the wires, an upper-body belt and a left knee belt to each other on or above a front part of the body of the user, the upper-body belt being a belt adapted to be worn on an upper half of the body of the user, the left knee belt being a belt adapted to be worn on a left knee of the user;
coupling, using a second wire among the wires, the upper-body belt and the left knee belt to each other on or above a back part of the body of the user;
coupling, using a third wire among the wires, the upper-body belt and a right knee belt to each other on or above the front part of the body of the user, the right knee belt being a belt adapted to be worn on a right knee of the user;
coupling, using a fourth wire among the wires, the upper-body belt and the right knee belt to each other on or above the back part of the body of the user;
when assisting the user in walking while carrying an object,
generating a tension greater than or equal to a first threshold value in the first wire during a first period, the first period being a period of 35% or more and 90% or less of a gait phase of a left leg of the user;
generating a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg;
generating a tension greater than or equal to the first threshold value in the third wire during a third period, the third period being a period of 35% or more and 90% or less of a gait phase of a right leg of the user;
generating a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg;
acquiring a left sensor value from a left sensor adapted to be attached to a left hand of the user;
acquiring a right sensor value from a right sensor adapted to be attached to a right hand of the user;
detecting a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value;
when the first condition is detected, making the tension of the second wire in the second period and the tension of the third wire in the third period greater than the tension of the first wire in the first period and the tension of the fourth wire in the fourth period; and
when the second condition is detected, making the tension of the first wire in the first period and the tension of the fourth wire in the fourth period greater than the tension of the second wire in the second period and the tension of the third wire in the third period, wherein
the tension of the first wire, the tension of the second wire, the tension of the third wire, and the tension of the fourth wire are generated and adjusted by motors controlled by a control circuit, and
each percentage of the gait phase of the left leg and each percentage of the gait phase of the right leg are determined by a walk timing detecting unit based on information obtained using a sensor.

10. The assistance method according to claim 9, wherein the left leg shifts from a stance phase to a swing phase during the first period, the left leg shifts from the swing phase to the stance phase during the second period,
the right leg shifts from the stance phase to the swing phase during the third period, and
the right leg shifts from the swing phase to the stance phase during the fourth period.

11. The assistance method according to claim 9, wherein
a first end of the first wire is fixed to the left knee belt,
a second end of the first wire is fixed to a first motor among the motors,
a first end of the second wire is fixed to the left knee belt,
a second end of the second wire is fixed to a second motor among the motors,
a first end of the third wire is fixed to the right knee belt,
a second end of the third wire is fixed to a third motor among the motors,
a first end of the fourth wire is fixed to the right knee belt, and
a second end of the fourth wire is fixed to a fourth motor among the motors.

12. The assistance method according to claim 9, further comprising:
coupling, using a fifth wire among the wires, the upper-body belt and the left knee belt to each other, the fifth wire extending on or above the front part of the body of the user in a direction crossing a direction in which the first wire extends;
coupling, using a sixth wire among the wires, the upper-body belt and the left knee belt to each other, the sixth wire extending on or above the back part of the body of the user in a direction crossing a direction in which the second wire extends;
coupling, using a seventh wire among the wires, the upper-body belt and the right knee belt to each other, the seventh wire extending on or above the front part of the body of the user in a direction crossing a direction in which the third wire extends;
coupling, using an eighth wire among the wires, the upper-body belt and the right knee belt to each other, the eighth wire extending on or above the back part of the body of the user in a direction crossing a direction in which the fourth wire extends;
when assisting the user in walking while carrying the object,
generating a tension greater than or equal to the first threshold value in the first wire and the fifth wire during the first period;
generating a tension greater than or equal to the first threshold value in the second wire and the sixth wire during the second period;
generating a tension greater than or equal to the first threshold value in the third wire and the seventh wire during the third period; and
generating a tension greater than or equal to the first threshold value in the fourth wire and the eighth wire during the fourth period, wherein
the tension of the fifth wire, the tension of the sixth wire, the tension of the seventh wire, and the tension of the eighth wire are generated and adjusted by the motors controlled by the control circuit.

13. The assistance method according to claim 9, wherein
a time point of 50% of the gait phase of the left leg determined by the walk timing detecting unit based on the information obtained using the sensor corresponds to a time point of 0% of the gait phase of the right leg determined by the walk timing detecting unit, and
a time point of 50% of the gait phase of the right leg determined by the walk timing detecting unit based on the information obtained using the sensor corresponds to a time point of 0% of the gait phase of the left leg determined by the walk timing detecting unit.

14. The assistance method according to claim 9, wherein the sensor is a gait sensor, the method further comprising:
acquiring a sensor value of the gait sensor that detects a gait cycle of the user; and
calculating the gait phase of the left leg and the gait phase of the right leg based on the sensor value.

15. An assistance method for assisting a movement of a user by using wires attached to a body of the user, the assistance method comprising:
coupling, using a first wire among the wires, an upper-body belt and a left knee belt to each other on or above a front part of the body of the user, the upper-body belt being a belt adapted to be worn on an upper half of the body of the user, the left knee belt being a belt adapted to be worn on a left knee of the user;
coupling, using a second wire among the wires, the upper-body belt and the left knee belt to each other on or above a back part of the body of the user;
coupling, using a third wire among the wires, the upper-body belt and a right knee belt to each other on or above the front part of the body of the user, the right knee belt being a belt adapted to be worn on a right knee of the user;
coupling, using a fourth wire among the wires, the upper-body belt and the right knee belt to each other on or above the back part of the body of the user;
when assisting the user in walking while carrying an object,
generating a tension greater than or equal to a first threshold value in the first wire during a first period, the first period being a period of 35% or more and 90% or less of a gait phase of a left leg of the user;
generating a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg;
generating a tension greater than or equal to the first threshold value in the third wire during a third period, the third period being a period of 35% or more and 90% or less of a gait phase of a right leg of the user;
generating a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg;
acquiring information specifying a hand that carries the object from a memory or an interface device;
when the information indicates a left hand of the user, making the tension of the second wire in the second period and the tension of the third wire in the third period greater than the tension of the first wire in the first period and the tension of the fourth wire in the fourth period; and
when the information indicates a right hand of the user, making the tension of the first wire in the first period and the tension of the fourth wire in the fourth period greater than the tension of the second wire in the second period and the tension of the third wire in the third period, wherein the tension of the first wire, the tension of the second wire, the tension of the third wire, and the tension of the fourth wire are generated and adjusted by motors controlled by a control circuit, and each percentage of the gait phase of the left leg and each percentage of the gait phase of the right leg are determined by a walk timing detecting unit based on information obtained using a sensor.

16. A non-transitory computer-readable recording medium storing a control program for causing an assist device including a processor to execute a process, the control program being used in the assist device including
    a first wire coupling an upper-body belt and a left knee belt to each other on or above a front part of a body of a user, the upper-body belt being a belt adapted to be worn on an upper half of the body of the user, the left knee belt being a belt adapted to be worn on a left knee of the user,
    a second wire coupling the upper-body belt and the left knee belt to each other on or above a back part of the body of the user,
    a third wire coupling the upper-body belt and a right knee belt to each other on or above the front part of the body of the user, the right knee belt being a belt adapted to be worn on a right knee of the user, and
    a fourth wire coupling the upper-body belt and the right knee belt to each other on or above the back part of the body of the user,
    the process comprising:
    when assisting the user in walking while carrying an object,
    causing motors to generate a tension greater than or equal to a first threshold value in the first wire during a first period, the first period being a period of 35% or more and 90% or less of a gait phase of a left leg of the user;
    causing the motors to generate a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg;
    causing the motors to generate a tension greater than or equal to the first threshold value in the third wire during a third period, the third period being a period of 35% or more and 90% or less of a gait phase of a right leg of the user;
    causing the motors to generate a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg;
    acquiring a left sensor value from a left sensor adapted to be attached to a left hand of the user;
    acquiring a right sensor value from a right sensor adapted to be attached to a right hand of the user;
    detecting a first condition or a second condition, the first condition being a condition in which the left sensor value is greater than or equal to a second threshold value and in which the right sensor value is smaller than the second threshold value, the second condition being a condition in which the right sensor value is greater than or equal to the second threshold value and in which the left sensor value is smaller than the second threshold value;
    when the first condition is detected, making the tension of the second wire in the second period and the tension of the third wire in the third period greater than the tension of the first wire in the first period and the tension of the fourth wire in the fourth period;
    when the second condition is detected, making the tension of the first wire in the first period and the tension of the fourth wire in the fourth period greater than the tension of the second wire in the second period and the tension of the third wire in the third period; and
    determining each percentage of the gait phase of the left leg and each percentage of the gait phase of the right leg by a walk timing detecting unit based on information obtained using a sensor.

17. A non-transitory computer-readable recording medium storing a control program for causing an assist device including a processor to execute a process, the control program being used in the assist device including
    a first wire coupling an upper-body belt and a left knee belt to each other on or above a front part of a body of a user, the upper-body belt being a belt adapted to be worn on an upper half of the body of the user, the left knee belt being a belt adapted to be worn on a left knee of the user,
    a second wire coupling the upper-body belt and the left knee belt to each other on or above a back part of the body of the user,
    a third wire coupling the upper-body belt and a right knee belt to each other on or above the front part of the body of the user, the right knee belt being a belt adapted to be worn on a right knee of the user, and
    a fourth wire coupling the upper-body belt and the right knee belt to each other on or above the back part of the body of the user,
    the process comprising:
    when assisting the user in walking while carrying an object,
    causing motors to generate a tension greater than or equal to a first threshold value in the first wire during a first period, the first period being a period of 35% or more and 90% or less of a gait phase of a left leg of the user;
    causing the motors to generate a tension greater than or equal to the first threshold value in the second wire during a second period, the second period being from a point in a range of 65% or more and less than 100% of the gait phase of the left leg to a point in a range of 0% or more and 25% or less of a subsequent gait phase of the left leg;
    causing the motors to generate a tension greater than or equal to the first threshold value in the third wire during a third period, the third period being a period of 35% or more and 90% or less of a gait phase of a right leg of the user;
    causing the motors to generate a tension greater than or equal to the first threshold value in the fourth wire during a fourth period, the fourth period being from a point in a range of 65% or more and less than 100% of the gait phase of the right leg to a point in a range of 0% or more and 25% or less of a subsequent gait phase of the right leg;
    acquiring information specifying a hand that carries the object from a memory or an interface device;
    when the information indicates a left hand of the user, making the tension of the second wire in the second period and the tension of the third wire in the third period greater than the tension of the first wire in the first period and the tension of the fourth wire in the fourth period;

when the information indicates a right hand of the user, making the tension of the first wire in the first period and the tension of the fourth wire in the fourth period greater than the tension of the second wire in the second period and the tension of the third wire in the third period; and determining each percentage of the gait phase of the left leg and each percentage of the gait phase of the right leg by a walk timing detecting unit based on information obtained using a sensor.

18. An assistance apparatus, comprising:

a first belt adapted to be worn on an upper half of a body of a user;

a left knee belt adapted to be worn above a left knee of the user;

a right knee belt adapted to be worn above a right knee of the user;

a first wire coupling the first belt with the left knee belt on or above a front part of the body;

a second wire coupling the first belt with the left knee belt on or above a back part of the body;

a third wire coupling the first belt with the right knee belt on or above the front part;

a fourth wire coupling the first belt with the right knee belt on or above the back part;

a first motor;

a second motor;

a third motor;

a fourth motor;

a left sensor adapted to be worn on a left hand of the user;

a right sensor adapted to be worn on a right hand of the user; and a controller, wherein when the assistance apparatus assistances the user in walking, (a) the first motor generates a first tension on the first wire during a first period, the first period being from a point in a first percentage range of a TL(i) to a point in a second percentage range of the TL(i), the first percentage range being 35 percent or more and 55 percent or less, the second percentage range being 80 percent or more and 90 percent or less, a magnitude of the first tension being a first threshold value or more, the TL(i) being an ith gait cycle of a left leg of the user, (b) the second motor generates a second tension on the second wire during a second period, the second period being from a point in a third percentage range of one gait phase of the TL(i) to a point in a fourth percentage range of a subsequent gait phase of the TL(i), the third percentage range being 65 percent or more and 90 percent or less, the fourth percentage range being 10 percent or more and 25 percent or less, (c) the third motor generates a third tension on the third wire during a third period, the third period being from a point in a fifth percentage range of a TR(i) to a point in a sixth percentage range of the TR(i), the fifth percentage range being 35 percent or more and 55 percent or less, the sixth percentage range being 80 percent or more and 90 percent or less, a magnitude of the third tension being the first threshold value or more, the TR(i) being an ith gait cycle of a right leg of the user, and (d) the fourth motor generates a fourth tension on the fourth wire during a fourth period, the fourth period being from a point in a seventh percentage range of one gait phase of the TR(i) to a point in an eighth percentage range of a subsequent gait phase of the TR(i), the seventh percentage range being 65 percent or more and 90 percent or less, the eighth percentage range being 10 percent or more and 25 percent or less, wherein the controller obtains a left weight value from the left sensor and a right weight value from the right sensor, wherein the controller obtains a left weight value from the left sensor and a right weight value from the right sensor, wherein when the controller detects a first condition that the left sensor detects a weight equal to or more than a second threshold value based on the left weight value and the right sensor detects no weight based on the right weight value, a maximum value of the second tension and a maximum value of the third tension are bigger than a maximum value of the first tension and a maximum value of the fourth tension, and wherein when the controller detects a second condition that the left sensor detects no weight based on the left weight value and the right sensor detects a weight equal to or more than the second threshold value based on the right weight value, a maximum value of the first tension and a maximum value of the fourth tension are bigger than a maximum value of the second tension and a maximum value of the third tension, and the first percentage range, the second percentage range, the third percentage range, and the fourth percentage range of the TL(i), and the fifth percentage range, the sixth percentage range, the seventh percentage range, and the eighth percentage range of the TR(i) are determined by a walk timing detecting unit based on information obtained using a sensor.

* * * * *